United States Patent
Mahfouz et al.

(10) Patent No.: US 9,642,572 B2
(45) Date of Patent: May 9, 2017

(54) MOTION TRACKING SYSTEM WITH INERTIAL-BASED SENSING UNITS

(71) Applicant: JointVue, LLC, Columbus, OH (US)

(72) Inventors: Mohamed R. Mahfouz, Knoxville, TN (US); Gary To, Knoxville, TN (US)

(73) Assignee: Joint Vue, LLC, Knoxville, TN (US)

( * ) Notice: Subject to any disclaimer, the term of this patent is extended or adjusted under 35 U.S.C. 154(b) by 489 days.

(21) Appl. No.: 13/841,402

(22) Filed: Mar. 15, 2013

(65) Prior Publication Data

US 2013/0217998 A1 Aug. 22, 2013

Related U.S. Application Data

(63) Continuation-in-part of application No. 13/196,701, filed on Aug. 2, 2011, now abandoned, and a
(Continued)

(30) Foreign Application Priority Data

Feb. 2, 2010 (WO) .......................... US2010022939

(51) Int. Cl.
*A61B 5/11* (2006.01)
*A61B 8/08* (2006.01)
(Continued)

(52) U.S. Cl.
CPC ............ *A61B 5/4528* (2013.01); *A61B 5/002* (2013.01); *A61B 5/0004* (2013.01);
(Continued)

(58) Field of Classification Search
CPC combination set(s) only.
See application file for complete search history.

(56) References Cited

U.S. PATENT DOCUMENTS 3,881,164 A 4/1975 Kossoff
4,016,750 A * 4/1977 Green .......................... 73/629
(Continued)

FOREIGN PATENT DOCUMENTS

WO 0063719 A1 10/2000
WO 2010088696 A1 8/2010

OTHER PUBLICATIONS

Baillot et al., "Automatic modeling of knee joint motion for the Virtual Reality Dynamic Anatomy (VRDA) tool", Virtual Reality, J.D. Westwood et al. (Eds.), IOS Press 1999, pp. 30-35 Medicine Meets.*
(Continued)

*Primary Examiner* — Katherine Fernandez
*Assistant Examiner* — Farshad Negarestan
(74) *Attorney, Agent, or Firm* — Willis IP, LLC; Ryan Willis

(57) ABSTRACT

Systems, apparatus, and method of monitoring a position of a joint. An inertial monitoring unit is configured to be coupled to a portion of a patient, such as a thigh. Another inertial monitoring unit is configured to be attached to another portion of the patient, such as a shank, that is connected to the other portion by a joint, such as a knee. The inertial monitoring units detect motion of their respective portions of the patient and transmit data indicative of this motion. These transmissions may be received by a computer and used to determine an orientation of the joint. The inertial monitoring units may also be coupled to vibration detection units and/or ultrasound modules that provide additional data regarding a condition of the joint.

22 Claims, 34 Drawing Sheets

Related U.S. Application Data continuation-in-part of application No. 12/364,267, filed on Feb. 2, 2009, now Pat. No. 8,444,564.

(51) Int. Cl.

| | |
|---|---|
| *A61B 5/00* | (2006.01) |
| *A61B 5/103* | (2006.01) |
| *G06F 19/00* | (2011.01) |
| *A61B 8/00* | (2006.01) |
| *A61B 5/0488* | (2006.01) |
| *A61B 34/20* | (2016.01) |
| *A61B 34/10* | (2016.01) |

(52) U.S. Cl.
CPC .......... *A61B 5/0059* (2013.01); *A61B 5/1036* (2013.01); *A61B 5/11* (2013.01); *A61B 5/1114* (2013.01); *A61B 5/1121* (2013.01); *A61B 5/1127* (2013.01); *A61B 5/4533* (2013.01); *A61B 5/6807* (2013.01); *A61B 5/6828* (2013.01); *A61B 5/6831* (2013.01); *A61B 5/6833* (2013.01); *A61B 5/72* (2013.01); *A61B 8/0858* (2013.01); *A61B 8/0875* (2013.01); *A61B 8/4227* (2013.01); *A61B 8/4263* (2013.01); *A61B 8/5223* (2013.01); *G06F 19/3481* (2013.01); *A61B 5/0488* (2013.01); *A61B 8/4472* (2013.01); *A61B 8/466* (2013.01); *A61B 34/20* (2016.02); *A61B 2034/105* (2016.02); *A61B 2562/02* (2013.01); *A61B 2562/0204* (2013.01); *A61B 2562/0219* (2013.01); *A61B 2562/0247* (2013.01); *A61B 2562/046* (2013.01)

(56) References Cited

U.S. PATENT DOCUMENTS

| | | | |
|---|---|---|---|
| 4,476,873 A | 10/1984 | Sorenson et al. | |
| 5,394,875 A | 3/1995 | Lewis et al. | |
| 5,413,116 A | 5/1995 | Radke et al. | |
| 5,447,154 A | 9/1995 | Cinquin et al. | |
| 5,488,952 A | 2/1996 | Schoolman | |
| 5,771,310 A | 6/1998 | Vannah | |
| 5,806,521 A | 9/1998 | Morimoto et al. | |
| 6,106,464 A | 8/2000 | Bass et al. | |
| 6,120,453 A | 9/2000 | Sharp | |
| 6,190,320 B1 | 2/2001 | Lelong | |
| 6,280,387 B1 | 8/2001 | Deforge et al. | |
| 6,537,233 B1 | 3/2003 | Rangayyan et al. | |
| 6,569,098 B2 | 5/2003 | Kawchuk | |
| 6,585,651 B2 | 7/2003 | Nolte et al. | |
| 7,454,242 B2 | 11/2008 | Fear et al. | |
| 7,660,623 B2 | 2/2010 | Hunter et al. | |
| 7,676,023 B2 | 3/2010 | Lang | |
| 7,678,052 B2 | 3/2010 | Torp et al. | |
| 7,684,846 B2 | 3/2010 | Johnson et al. | |
| 7,769,422 B2 | 8/2010 | DiSilvestro et al. | |
| 7,949,386 B2 | 5/2011 | Buly et al. | |
| 8,089,417 B2 | 1/2012 | Popovic et al. | |
| 8,265,728 B2 | 9/2012 | MacMahon et al. | |
| 8,444,564 B2 | 5/2013 | Mahfouz et al. | |
| 2005/0043660 A1* | 2/2005 | Stark ................. A61F 5/0106 602/19 |
| 2005/0093859 A1 | 5/2005 | Sumanaweera et al. | |
| 2006/0161363 A1* | 7/2006 | Shibasaki et al. ............... 702/94 |
| 2007/0287900 A1 | 12/2007 | Breen et al. | |
| 2008/0009722 A1 | 1/2008 | Simopoulos et al. | |
| 2008/0094396 A1 | 4/2008 | Sabczynsdi et al. | |
| 2008/0194997 A1* | 8/2008 | Zhang ........................ 600/595 |
| 2009/0018445 A1 | 1/2009 | Schers et al. | |
| 2009/0137907 A1 | 5/2009 | Takimoto et al. | |
| 2010/0100011 A1 | 4/2010 | Roche | |
| 2010/0125229 A1* | 5/2010 | Rudolph et al. ................. 602/16 |
| 2012/0029345 A1* | 2/2012 | Mahfouz ............. A61B 5/1036 600/427 |

OTHER PUBLICATIONS

United States Patent and Trademark Office, "International Preliminary Report on Patentability", in corresponding International Application No. PCT/US2010/022939, mailed Aug. 2, 2011, 7 pp.

European Patent Office, "International Search Report and Written Opinion", in corresponding International Application No. PCT/US2011/046318, mailed Nov. 11, 2011, 13 pp.

United States Patent and Trademark Office, International Search Report and Written Opinion, in corresponding International Application No. PCT/US2011/054952, mailed Jan. 26, 2012, 9 pp.

United States Patent and Trademark Office, "International Search Report and Written Opinion", in corresponding International Application No. PCT/US2010/022939, mailed Mar. 19, 2010, 4 pp.

United States Patent and Trademark Office, "Written Opinion of the International Preliminary Examining Authority", in corresponding International Application No. PCT/US2011/046318, mailed Jul. 8, 2012, 6 pp.

United States Patent and Trademark Office, "International Search Report and Written Opinion", in corresponding International Application No. PCT/US2012/060261, mailed Jan. 9, 2013, 10 pp.

United States Patent and Trademark Office, "Non-Final Office Action", in related U.S. Appl. No. 13/196,701, mailed Apr. 10, 2013, 18 pp.

United States Patent and Trademark Office, "Final Office Action", in related U.S. Appl. No. 13/196,701, mailed Dec. 19, 2013, 11 pp.

United States Patent and Trademark Office, "Non-Final Office Action", in related U.S. Appl. No. 12/364,267, mailed Nov. 9, 2011, 15 pp.

United States Patent and Trademark Office, Final Office Action, in related U.S. Appl. No. 12/364,267, mailed May 23, 2012, 18 pp.

European Patent Office, Written Opinion of the International Searching Authority, in corresponding International Application No. PCT/US2011/046318, 6 pp.

Mahfouz, Mohamed R. "Operating Room of the Future Orthopedic Perspective", Proceedings of the 2008 IEEE, CIBEC 2008, 9 pp.

United States Patent and Trademark Office, "International Search Report and Written Opinion", in corresponding International Application No. PCT/US2013/025131, mailed Apr. 26, 2013, 8 pp.

\* cited by examiner

MOTION TRACKING SYSTEM WITH INERTIAL-BASED SENSING UNITS

This application is a continuation-in-part of U.S. patent application Ser. No. 13/196,701, filed Aug. 2, 2011, which claims the filing benefit of PCT Patent Application No. PCT/US2010/022939, filed on Feb. 2, 2010, and is a continuation-in-part of U.S. patent application Ser. No. 12/364,267, filed on Feb. 2, 2009, the disclosures of which are all incorporated by reference herein in their entireties.

FIELD OF THE INVENTION

The present invention relates generally to in vivo imaging modalities and, more specifically, to real-time in vivo movement tracking and imaging modalities for human and non-human patients.

BACKGROUND

Body motion tracking has a wide range of applications extending from medicine to entertainment. For example, body motion tracking has become a popular method for interfacing with virtual reality systems. Personal communication devices, such as smart phones, may use motion tracking system to detect user interaction with the device. Within the field of biomedical engineering, data analysis of body motion is one component used for understanding kinematics and the kinetics of the human body. Once the kinematics of a patient are understood, this knowledge may be used to design prosthetics, implants, and diagnostic instruments. Known body motion tracking methodologies include capturing body motion by collecting data from bio-imaging units that use ionizing radiation to image the patient, and from motion tracking devices attached to the patient that capture motion directly. This data may then be analyzed to determine design parameters for the device in question.

Although normal human body motion is well studied, there remain gaps within this knowledge base with respect to correlating abnormal motions to clinical diagnosis. One of the obstacles to more extensive use of motion tracking using known methodologies is that conventional systems are bulky and not always available in hospital. These systems typically require specially-trained technicians, making day-to-day diagnostic use impractical. Systems that use ionizing radiation may also be undesirable due to potential adverse health effects resulting from exposure the radiation used to image the patient.

One type of motion tracking device is an Inertial Measurement Unit (IMU). IMUS are configured to detect motion based on the effects of acceleration on a sensor. Generally, an IMU includes multiple inertial measuring sensors, such as accelerometers and/or gyroscopes that allow the position of the IMU to be determined without an external reference. Conventional types of IMU systems vary in accuracy and size. For example, micro-machined micro-electro-mechanical system ("MEMS") based sensors coupled with integrated circuit technology have allowed IMUS to be miniaturized. However, the static accuracy of MEMS-based IMUS is limited to about 0.4 degrees in orientation and about 4 degrees under cyclic motion.

Thus, while conventional MEMS-based IMUS may have potential for biomedical implementations, the resolution/accuracy of MEMS-based IMUS remains relatively low. More specifically, currently, commercially-available IMU systems have pre-determined and limited operational dynamic range that is not tailored and optimized for human body motion tracking. Conventional IMU systems are thus not suitable for determining patient motion because they do not meet the resolution and dynamic range requirements, which vary depending on the activities being monitored.

As a result, there remains a need for improved motion tracking systems, apparatuses, and methods that are easy to use, highly accurate, and low in cost, with high mobility, and that avoid using radiation-based imaging technologies.

SUMMARY OF THE INVENTION

The present invention overcomes the foregoing problems and other shortcomings, drawbacks, and challenges of known, conventional motion tracking systems. While the invention will be described in connection with certain embodiments, it will be understood that the invention is not limited to these embodiments. To the contrary, this invention includes all alternatives, modifications, and equivalents as may be included within the spirit and scope of the present invention.

In an embodiment of the invention, a joint monitoring apparatus is provided. The apparatus includes a first inertial monitoring unit configured to be coupled to and detect motion of a first portion of a patient, and to collect and transmit data indicative of the detected motion. The apparatus also includes a second inertial monitoring unit configured to be attached to and detect motion of a second portion of the patient, and to collect and transmit data indicative of the detected motion. The first and second portions of the patient are coupled by a joint, so that the motion of the first and second portions of the patient may be used to determine movement of the joint.

In another embodiment of the invention, a method of monitoring a joint is presented. The method includes detecting motion of a first portion of a patient with a first inertial monitoring unit and collecting data indicative of the detected motion in the first inertial monitoring unit. The method also includes detecting motion of a second portion of a patient with a second inertial monitoring unit, and collecting data indicative of the detected motion in the second inertial monitoring unit. The collected data is then transmitted from the first and second inertial monitoring units.

BRIEF DESCRIPTION OF THE FIGURES

The accompanying drawings, which are incorporated in and constitute a part of this specification, illustrate embodiments of the present invention and, together with a general description of the invention given above, and the detailed description of the embodiments given below, serve to explain the principles of the present invention.

DETAILED DESCRIPTION

Figure 1:
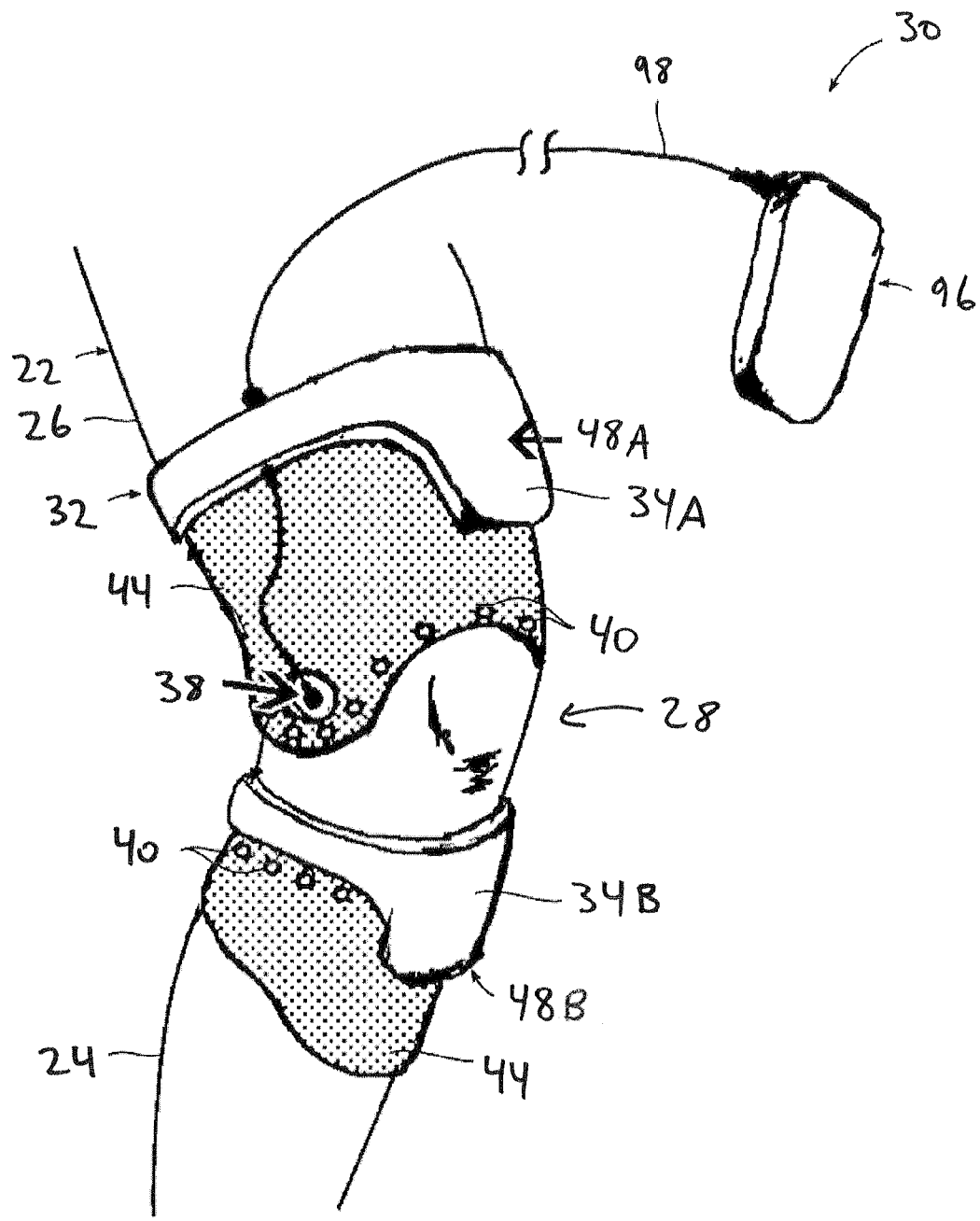
FIG. 1 is a side elevational view of a joint monitoring apparatus for used in monitoring motion of a knee joint, including the individual components of the knee joint.
Figure 2:
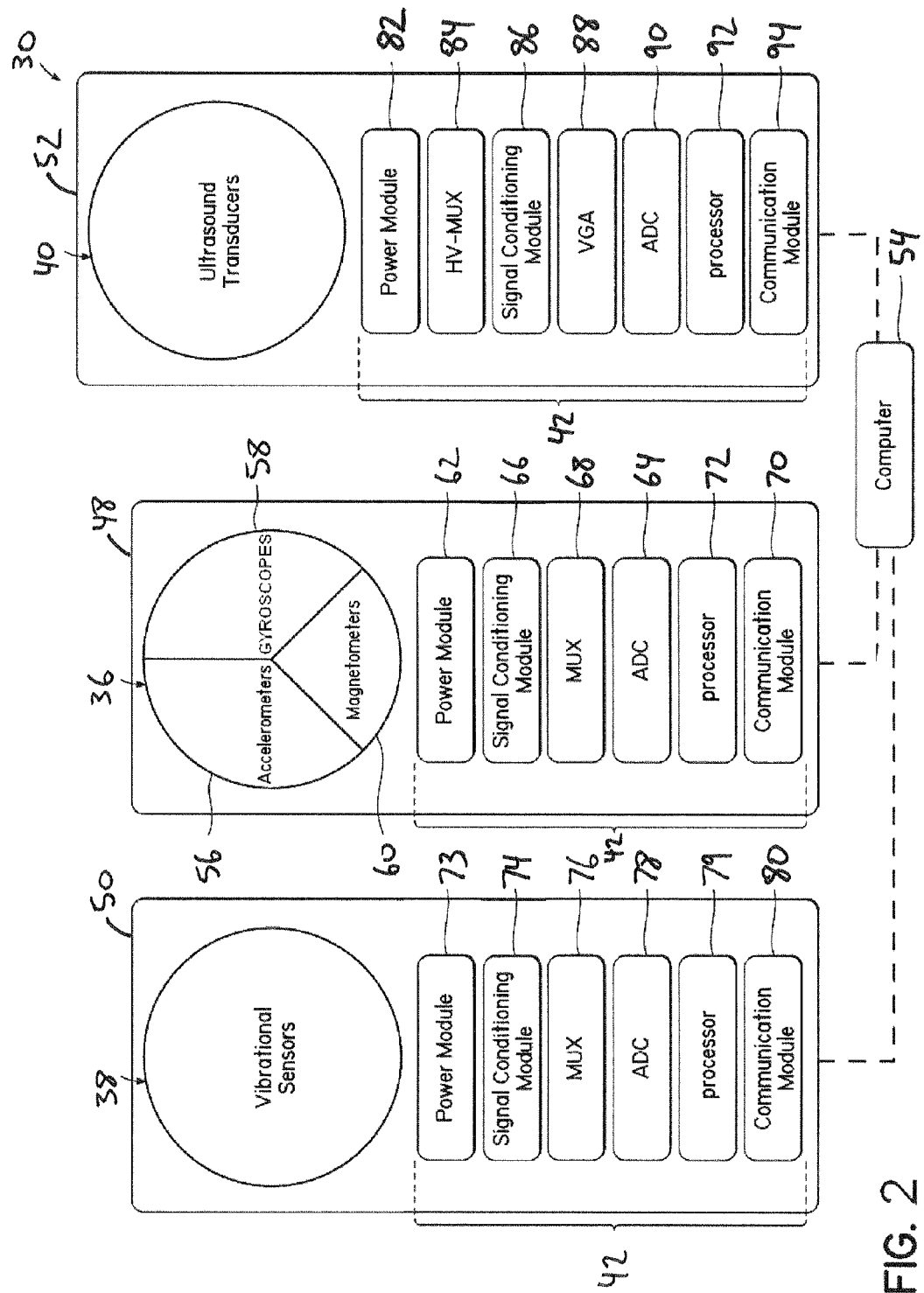
FIG. 2 is a schematic view of an inertial monitoring unit, vibration detection module, and a pulse echo ultrasound module for use with the joint monitoring apparatus of FIG. 1.

Embodiments of the invention are directed to a joint monitoring apparatus that is divided into an external navigation module that utilizes an inertial monitoring unit (IMU) to track motion, and an internal bone tracking module that utilizes ultrasound to track the location of bones in the patient relative to the IMU. To this end, the inertial monitoring unit monitors the external orientation between the body segments. The ultrasound system is used to monitor the relative motion of IMU to the bone. By combining the two systems, the joint monitoring apparatus allows performance of in-vivo tracking with complete wireless connectivity in a standalone system Referring now to FIG. 1, and in accordance with an exemplary embodiment of the invention, a patient leg 22 is shown including a shank 24 and thigh 26 joined by a knee joint 28. A joint monitoring apparatus 30 is depicted in the form of a knee brace 32 for use in monitoring and tracking motion of the knee joint 28. The knee brace 32 may include a housing that supports the joint monitoring apparatus 30. The housing may include an upper section 34A having an inertial monitoring unit 48A, and a lower section 34B having an inertial monitoring unit 48B. The knee brace 32 may also include one or more vibration sensors 38, one or more ultrasound transducers 40, and signal processing circuitry 42 (FIG. 2). The signal processing circuitry 42 may be configured to process signals generated by a plurality of inertia monitoring sensors 36 in the inertial monitoring units 48A, 48B, the vibration sensors 38, and the ultrasound transducers 40. The housing may also include at least one flexible segment 44 configured to secure the knee brace 32 to the leg 22, and that locates the upper section 34A relative to the lower section 34B of the housing 34. The flexible segment 44 may include one or more layers of elastic material having an intermediate layer (not shown) that is proximate to the patent's skin and that serves as an acoustic impedance matching layer. The one or more layers of elastic material may thereby facilitate transmission of an ultrasound pulse into the knee joint 28 from the ultrasound transducers 40. In an alternative embodiment, the upper and lower sections 34A, 34B may be located by a rigid segment (not shown), such as a hinge or other rigid member configured to allow pivoting motion between the upper and lower sections 34A, 34B.

One exemplary material suitable for use in the flexible segment 44 is Alpha® Liner, available from the Ohio Willow Wood Company of Mt. Sterling, Ohio. The Alpha® Liner includes a proprietary blend of silicone, Vitamin E, and skin conditioners, and yields a pleasing surface that is non-greasy, non-tacky, and comfortable against the skin. The Alpha® Liner material is described in more detail in U.S. Pat. No. 8,317,873, entitled "POLYMERIC PROSTHETIC LINER WITH CONTROLLED STRETCH CHARACTER- ISTICS", filed on Feb. 23, 2010, the disclosure of which is incorporated herein by reference in its entirety. Because this material eliminates any air gaps, ultrasound signals pass readily through it and into the patient. The knee brace 32 may also include elastic straps (not shown) with facing materials having hook and loop fasteners (commonly known as VELCRO®) for securing the brace 32 to the patient. Referring now to FIG. 2, a schematic of the joint monitoring apparatus 30 is illustrated showing an inertial monitoring unit 48, a vibration detection module 50, and an ultrasound module 52 operatively coupled to a computer 54. The inertial monitoring unit 48 may detect motion using the inertial monitoring sensors 36. As compared with position tracking systems that rely on optical or electromagnetic localization, the inertial monitoring sensors 36 do not require external observation units. Rather, the inertial monitoring sensors 36 include a plurality of sensors that detect motion unilaterally, thereby allowing the inertial monitoring unit 48 to operate without the need for external reference signals. The inertial monitoring sensors 36 in the exemplary embodiment include, but are not limited to, one or more accelerometers 56, gyroscopes 58, and magnetometers 60.

In an exemplary embodiment of the invention, the inertial monitoring sensors 36 may include an accelerometer 56 that is sensitive to static forces, i.e., an accelerometer configured to output a DC voltage in response to being subjected to a constant acceleration. Thus, the accelerometer 56 may be sensitive to the constant force of gravity. The accelerometer 56 may also include a sensing axis so that the accelerometer 56 generates an output indicating a force of 1 G when the accelerometer sensing axis is perpendicular to the force of gravity. As the accelerometer sensing axis is tilted, the force of gravity acts at an angle to the axis. In response to tilting the sensing axis, the output signal may decrease, indicating a lower sensed level of acceleration. This decrease may continue until the accelerometer sensing axis is positioned parallel to the force of gravity, at which point the signal may reach an output level indicative of a force of 0 G. Accordingly, the relationship between gravity and the accelerometer sensing axis may be used to determine a tilt angle of the accelerometer 56 with respect to the local gravitational field. In an alternative embodiment of the invention, the accelerometer 56 may be a three axis accelerometer having three orthogonal accelerometer sensing axes. In this embodiment, the accelerometer 56 may be configured to monitor the tilt angle for each of the three accelerometer sensing axes relative to the local gravitational field.

The gyroscope 58 may be configured to monitor an angular motion of a gyroscopic sensing axis relative to a local IMU frame. To this end, the gyroscope 58 may generate an output indicative of an angular velocity being experienced by the gyroscopic sensing axis. Thus, a change in the angle of the gyroscopic sensing axis relative to an initial orientation of the inertial monitoring unit 48 may be determined based on the output signal. This change in the angle of the gyroscopic sensing axis may, in turn, be used to determine the angular orientation of the inertial monitoring unit 48 and the orientation of the brace 32 in a known manner. That is, the gyroscope 58 generates an output relative to the angular velocity experienced by the gyroscopic sensing axis. Thus, repositioning the gyroscopic sensing axis relative to an initial orientation may be calculated in accordance with the Newton's equations of angular motion:

$$\angle = \int \omega \Delta t = \angle_i + \omega \Delta t$$

where $\angle$ is the angle of orientation, and $\angle_i$ is the orientation from previous state.)

The magnetometer 60 may generate one or more output signals indicative of the strength and/or orientation of a magnetic field relative to the magnetometer 60. The magnetometer 60 may thus be configured to serve as a compass and/or magnetic field monitor that detects relative motion between a magnetic sensing axis of the magnetometer 60 and a local magnetic field. The outputs generated by the magnetometer 60 may thereby represent changes in a magnetic field experienced on each magnetic sensing axis. In use, at least two magnetic sensing axes may be used to determine an angle between the inertial monitoring unit 48 and the axis of the magnetic field lines passing through the magnetometer 60. If one of the two magnetic sensing axes becomes insensitive to the local magnetic field (e.g., one of the two magnetic sensing axes is rotated to a position that is orthogonal to the magnetic field), then a third magnetic sensing axis may be used to determine the angle. In an alternative embodiment, tilt angles may be determined from one or more output signals of the accelerometers 56. These tilt angles may in turn be used to compensate for the effects of tilting the magnetic sensing axis.

The inertial monitoring unit 48 may further include a power module 62, an analog-to-digital converter (ADC) 64, a signal conditioning module 66, a multiplexer 68, a communication module 70, and a processor 72. The power module 62 may include circuitry configured to provide power to the components of the inertial monitoring unit 48, e.g., a +3.3 V and/or a +5 V direct current (DC) power source. The power module 62 may also provide a reference voltage to the ADC 64.

The signal conditioning module 66 may couple the output of the inertial monitoring sensors 56 to the ADC 64, and may be configured to reduce noise in the signals provided to the processor 72 from the ADC 64 by amplifying the signals provided to the ADC 64. The level of the signals provided to the ADC 64 may thereby be adjusted so that their amplitudes are within a desired operating range of the ADC 64 input. To this end, the signal conditioning module 66 may provide optimal input signals to the ADC 64 using one or more analog circuits. For example, the signal conditioning module 66 may include a low pass filter, such as a passive low pass filter for reducing high frequency noise from the IMU sensor outputs and to prevent aliasing, and/or an amplifier to amplify the sensor signal to be within a desired input range of the ADC 64.

The multiplexer 68 may include a plurality of inputs, with one input operatively coupled to each of the outputs of the inertial monitoring sensors 36. The multiplexer may also include a single output operatively coupled to an input of the ADC 64. The multiplexer 68 may operate as a high frequency analog switch that sequentially couples the signals at each of the plurality of multiplexer inputs to the multiplexer output. The multiplexer 68 may thereby serialize signals received on multiple inputs into a single time-division multiplexed output that is provided to the input of the ADC 64. In an exemplary embodiment of the invention, the multiplexer 68 may multiplex 16 output signals from the inertial monitoring sensors 36 into one input that is coupled to the ADC 64. The output generated by the multiplexer 68 may be converted into a corresponding digital signal by the ADC 64. In an exemplary embodiment of the invention, the ADC 64 may include a high resolution converter that converts the analog input into a digital signal having a resolution of 24 bits per sample. Alternatively, a lower resolution ADC 64 (e.g., a 16 bit converter) may be used to achieve a higher processing speed and/or a greater sampling rate.

The communication module 70 may include a wireless communication circuit that transmits the digital data generated by the ADC 64 to the computer 54 over a wireless link. The communication module 70 may operate, for example, on one of three frequency bands (e.g., 400 MHz, 916 MHz, and 2.4 GHz) approved by the Federal Communications Commission for unlicensed medical and scientific applications. The communication module 70 may use any suitable wireless or wired communication protocol, such as IEEE 802.15.1 (Bluetooth®), X.25, IEEE 802.11 (WiFI), or a custom protocol such as ultra-wideband (UWB) communication as appropriate depending on the application, to encode the digital data for transmission to the computer 54. Protocols may include signaling, authentication, communication with multiple inertial monitoring units 48, and error detection and correction capabilities.

The processor 72 may be configured to operatively couple and control the ADC 64, the multiplexer 68, and the communication module 70. The processor 72 may acquire digital data from the output of the ADC 64, package the data into data packets, and send the data packets to the communication module 70 for transmission to the computer 54. In an embodiment of the invention, the processor 72 may be a low power processor in order to minimize power consumption of the joint monitoring apparatus 30. In an alternative embodiment, the processor 72 may be a higher powered processor, such as a digital signal processor (DSP) or application specific integrated circuit (ASIC) so that the processor 72 may be used to perform digital signal processing, such as data compression, prior to transmitting the data to the computer 54. Multiple core or multiple processor architectures, and or a field programmable gate array (FPGA) may also be used.

Similarly as described above with respect to the inertial monitoring unit 48, the vibration detection module 50 may include one or more vibration sensors 38, and signal processing circuitry 42 comprising a power module 73, a signal conditioning module 74, which may include a charge amplifier (not shown), a multiplexer 76, an ADC 78, a processor 79, and a communication module 80. The signal processing circuitry 42 of vibration detection module 50 may operate to provide signals generated by the vibration sensors 38 to the computer 54. The vibrations detected by the vibration sensors 38 may thereby be used to provide insight into the condition of a patient's joint, such as the knee joint 28 in FIG. 1. To this end, the one or more vibration sensors 38 may be used to collect a vibration "signature" of femur and tibia interaction (or other bones forming a joint, as the case may be) during patient activities. The vibration pattern generated during knee motion may thereby be used to help differentiate a healthy patient from an osteoarthritic patient. The observed vibration may thus provide a useful indicator for diagnosing a condition of the joint.

One exemplary vibration sensor 38 is a dynamic accelerometer, which is a type of accelerometer configured to detect rapid changes in acceleration, such as may be associated with vibrations generated by a moving joint. In an embodiment of the invention, the joint monitoring apparatus 30 may be configured so that the vibration sensor 38 is detachable to allow positioning of the sensor 38 in proximity to a desired portion of the joint. As best shown in FIG. 1, the detachable vibration sensor 38 may be placed near the knee joint 28 and secured with adhesives to monitor vibration while the knee joint 28 is in motion. As compared to static accelerometers, dynamic accelerometers are not necessarily sensitive to a static accelerative force, such as gravity. However, in an alternative embodiment of the invention, accelerometers having a wide frequency range may be used to detect both patient motion and joint vibration, so that both these signals are provided to the computer 54 from a single accelerometer. The power module 73 may include, for example, a +3.3 V DC source, a +5 V DC source, and power source having an output voltage between +18 V and +30 V (e.g., +24 V) DC. The power module may also provide a precision voltage reference to the ADC 78

The signal generated by the vibration sensors 38 may be processed by the signal conditioning module 74 before entering the multiplexer 76 and ADC 78, similarly as described above with reference to the inertial monitoring sensors 36. As compared to the ADC 64 of the inertial monitoring unit 48, the ADC 78 of vibration detection module 50 may have a higher sample rate to capture the higher frequency signals generated by the vibration sensors 38 (e.g., a sample rate above the Nyquist rate for the desired bandwidth of the vibration sensor output signals). To this end, the ADC 78 of vibration detection module 50 may be selected to trade resolution for a higher sample rate. The digital data output by the ADC 78 may be coupled to the communication module 80 for processing and transmission to the computer 54 similarly as described above with respect to the inertial monitoring unit 48.

The processor 79 may be configured to control the components of the vibration detection module 50, as well as receive the digitized output signal from the ADC 78, package the received data into data packets, and send the data packets to the communication module 80 for transmission to the computer 54. Similarly as discussed with respect to inertial monitoring unit 48, the processor 79 may be any suitable processor, such as a low power processor in order to minimize power consumption of the joint monitoring apparatus 30. In an alternative embodiment, the processor 79 may be a higher powered processor, such as a digital signal processor (DSP) or application specific integrated circuit (ASIC) so that the processor 72 may be used to perform digital signal processing, such as data compression, prior to transmitting the data to the computer 54. Multiple core or multiple processor architectures, and or a field programmable gate array (FPGA) may also be used.

The communication module 80 may include a wireless communication circuit that transmits the digital data generated by the ADC 78 to the computer 54 over a wireless link. The communication module 80 may operate, for example, any of the frequency bands (e.g., 400 MHz, 916 MHz, and 2.4 GHz) approved by the Federal Communications Commission for unlicensed medical and scientific applications. The communication module 80 may use any suitable wireless or wired communication protocol, such as Bluetooth®, X.25, WiFI, or a custom protocol such UWB communication as appropriate depending on the application, to encode the digital data for transmission to the computer 54. Protocols may include signaling, authentication, communication with multiple vibration detection modules, and error detection and correction capabilities.

The ultrasound module 52 may include one or more ultrasound transducers 40, a power module 82, a high voltage multiplexer 84, a signal conditioning module 86, a multi-channel variable gain amplifier (VGA) 88, an ADC 90, a processor 92, and a communication module 94. The ultrasound transducers 40 may include a plurality of pulse echo mode ultrasound transducers arranged in the flexible segment 44 of knee brace 32. Each ultrasound transducer 40 may be comprised of a piezoelectric crystal configured to emit an ultrasound pulse in response to an electrical signal. The ultrasound pulse may be transmitted from the ultrasound transducer 40 through the skin and soft tissues of the patient. When the ultrasound pulse reaches a boundary between tissues having different acoustic impedance properties, such as an interface between bone and a soft-tissue, an echo is generated and reflected back to the ultrasound transducer 40. The time delay between an initial echo (i.e., the echo generated by the interface between the flexible segment 44 of knee brace 32 and the skin) and an echo generated by the bone-tissue interface may be used to determine a distance between the ultrasound transducer 40 and the bone. By including one or more ultrasound transducers 40 in the brace 32, the relative motions between the knee brace 32 and the patient's bones may be determined as is described in greater detail in U.S. Application Pub. No. 2012/0029345, filed on Aug. 2, 2011 and entitled "NON-INVASIVE DIAGNOSTIC SYSTEM", the disclosure of which is incorporated herein by reference in its entirety.

In addition to providing power to the ultrasound module 52, the power module 82 may include a high voltage pulse generator configured to excite the ultrasound transducers 40 with ultrasound bursts via the high voltage multiplexer 84. To this end, the high voltage multiplexer 84 may include an analog switch configured to selectively couple the high voltage output of the high voltage pulse generator to one or more of the plurality of ultrasound transducers 40.

The signal conditioning module 86 may be coupled to (or include) the multi-channel VGA 88, which may provide a time-based variable gain control over the received echo signals generated by the ultrasound transducers. Normally the transmitted ultrasound pulse and the returning echo are attenuated by soft tissue as each signal propagates through the human body. Accordingly, after the ultrasound transducer 40 emits the ultrasound pulse, the amplitude of the pulse is attenuated as the signal passes through the patient. Thus, echo signals originating from deep within the patient tend to have a lower amplitude than those originating from close to the surface due to their longer propagation path. A received echo signal that initially has a sufficient amplitude to be encoded by the ADC 90 may therefore fade into the background noise by the end of the ultrasound scanning or receiving period. To address this issue, the VGA 88 may be configured to dynamically increase the gain applied to the received echo signal over the receiving period to compensate for this varying attenuation. The gain may also be varied across the inputs to the VGA 88 so that the gain may be adjusted independently for each ultrasound transducer 40 coupled to the VGA 88. The VGA 88 may thereby improve the reliability and quality of the echo signal conversion by the ADC 90 as compared to systems lacking this dynamic gain feature.

The ADC 90 of ultrasound module 52 may be similar to the ADCs 64, 78 of inertial monitoring unit 48 and vibration detection module 50. However, because the ADC 90 is responsible for converting the echo signal of an ultrasound pulse into to a digital signal, the ADC 90 may require a higher sampling frequency than either the ADC 64 of inertial monitoring unit 48 or the ADC 78 of vibration detection module 50. This higher conversion rate may be required because the bandwidth of the ultrasound pulse is significantly higher than signals generated by either the inertial monitoring sensors 36 or vibration sensors 38. In any case, the output signal generated by the ADC 90 may include an array of digital data points, or samples representing the analog echo signal similarly as described above with respect to the other ADCs 64, 78.

The processor 92 may be configured to control the components of the ultrasound module 52, as well as receive the digitized output signal from the ADC 90, package the received data into data packets, and send the data packets to the communication module 94 for transmission to the computer 54. Similarly as discussed with respect to inertial monitoring unit 48, the processor 92 of ultrasound module 52 may be any suitable processor. In an embodiment of the invention, the processor 92 may be a DSP, ASIC, multiple core processor, and/or may include multiple processors configured to process the digital signal generated from the ultrasound transducers 40 into physical units indicative of the distance between the ultrasound transducer 40 and the bone surface. Signal processing may thereby be performed in the ultrasound module 52 prior to transmission of the processed data to the computer 54. This processing may reduce the amount of data that must be transmitted to, and the processing load on, the computer 54. In any case, and similarly as described above with respect to the inertial monitoring unit 48, the communication module 94 may include a wireless communication circuit that transmits the digital data generated by the ADC 90 and/or processor 92 to the computer 54 over a wireless link.

The modules 48, 50, 52 may receive power from batteries incorporated into the housing of the knee brace 32. In an alternative embodiment, the modules 48, 50, 52 may receive power from an external power source 96 coupled to the brace 32 via a power line 98. Using an external power source 96 may reduce the size and weight of the joint monitoring apparatus 30 as well as allow the use of higher performance circuitry.

One or more of the communication modules 70, 80, 94 may be incorporated into the housing of the knee brace 32. In an alternative embodiment, to reduce the size and weight of the joint monitoring apparatus 30, one or more of the communication modules 70, 80, 94 may also be external to the knee brace 32, and may communicate with the electronic components of the modules 48, 50, 52 wirelessly or via one or more wires tethering the one or more communication modules 70, 80, 94 to the knee brace 32. In embodiments having external communication modules, the communication modules may be integrated into the external power source 96. In embodiments including communications modules 70, 80, 94 employing wireless communication links, the communications modules 70, 80, 94 may operate, for example, on any bandwidths (e.g., 400 MHz, 916 MHz, and 2.4 GHz) that are approved by the Federal Communications Commission for medical and scientific applications. As discussed with respect to the communication module 70 of inertial monitoring unit 48, the communication modules 70, 80, 94 may use any suitable wireless or wired communication protocol, such as IEEE 802.15.1 (Bluetooth®), X.25, IEEE 802.11 (WiFI), or a proprietary protocol as appropriate depending on the application, to encode the digital data for transmission to the computer 54. Protocols may include signaling, authentication, communication with multiple inertial monitoring units 48, and error detection and correction capabilities. In an embodiment of the invention, the accelerometer 56, the gyroscope 58, and the magnetometer 60 may be separated into distinct sensor circuit layouts to increase the modularity and customizability of the inertial monitoring unit 48. Furthermore, the sensitivities of the inertial monitoring sensors 36 in the inertial monitoring unit 48 may be designed to perform within a finite sensitivity range and boundary conditions. For example, the gyroscope 58 may have a sensitivity rating selected to accommodate an expected maximum measurable angular motion for a particular application. Because each motion performed by the joint under study has a different kinematic characteristic (for example, the shank 24 has far less motion during a rising motion from a chair as compared with walking), selecting the components of the inertial monitoring unit 48 in accordance with a selected capability for a particular motion may optimize the performance of the joint monitoring apparatus 30. Moreover, segmenting the circuit layouts allows for greater adaptability of the inertial monitoring unit 48 for use in analyzing the motion of another portion of the patient's body. That is, while the illustrative embodiment is specifically drawn to the knee joint, other joints (such as the hip, the shoulder, and the spine) may exhibit significantly different kinematics as compared with the knee. The modular design of the inertial monitoring unit 48 and the inertial monitoring sensors 36 provides for a quick and easy adjustment of the motion tracking apparatus 30 by enabling the switching or exchange of one component for another having a different selected sensitivity range that is better suited for evaluating the joint or movement in question. Additionally, while the illustrative embodiment of the present invention is specifically described as including one accelerometer 56, one gyroscope 58, and one magnetometer 60, those having ordinary skill in the art will understand that the inertial monitoring unit 48 may have other combinations and numbers of inertial monitoring sensors 36. Thus, inertial monitoring units 48 in accordance various embodiments of the present invention may include any combination of components, including, for example, two accelerometers 56, two gyroscopes 58 each with a different operational dynamic range, and one magnetometer 60. The selection of components may be based, in part, on the particular need or preference of the evaluating physician, the joint to be evaluated, the range of motion of the patient, the expected rate of motion (slow versus fast movement or rotation), and/or the range of motion permitted in the evaluation setting (examination room versus surgical table).

Figure 3:
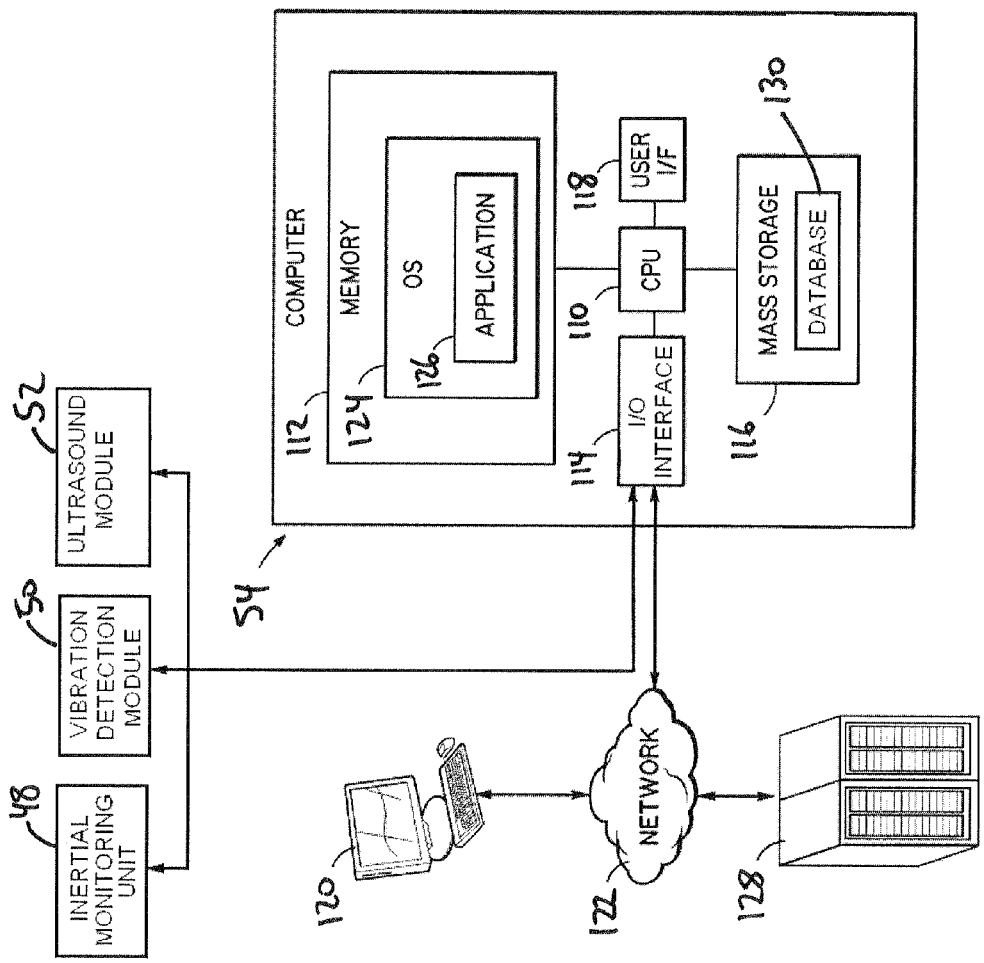
FIG. 3 is a schematic view of an exemplary computing environment for use with the joint monitoring apparatus of FIG. 1.

Referring now to FIG. 3, the computer 54 may include a processor 110, memory 112, an input/output (I/O) interface 114, a mass storage device 116, and a user interface 118. The computer 54 may represent any suitable type of computer, computing system, server, disk array, or programmable devices such as a handheld device, a networked device, or an embedded device, etc. The computer 54 may be in communication with one or more networked computers 120 via one or more networks 122, such as a cluster or other distributed computing system, through the I/O interface 114.

The processor 110 may include one or more devices selected from processors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions that are stored in the memory 112. Memory 112 may be a single memory device or a plurality of memory devices including but not limited to read-only memory (ROM), random access memory (RAM), volatile memory, non-volatile memory, static random access memory (SRAM), dynamic random access memory (DRAM), flash memory, or cache memory. Memory 112 may also include a mass storage device such as a hard drive, optical drive, tape drive, non-volatile solid state device, or any other device capable of storing digital information.

The processor 110 may operate under the control of an operating system 124 that resides in memory 112. The operating system 124 may manage computer resources so that computer program code embodied as one or more computer software applications, such as an application 126 residing in memory 112 may have instructions executed by the processor 110. In an alternative embodiment, the processor 110 may execute the applications 126 directly, in which case the operating system 124 may be omitted.

The mass storage device 116 typically includes at least one hard disk drive and may be located externally to the computer 54, such as in a separate enclosure or in one or more networked computers 126, one or more networked storage devices 128 (including, for example, a tape or optical drive), and/or one or more other networked devices (including, for example, a server). The mass storage device 116 may also host one or more databases 130.

The user interface 118 may be operatively coupled to the processor 110 of computer 54 in a known manner to allow a system operator to interact directly with the computer 54. The user interface 118 may include output devices such as video and/or alphanumeric displays, a touch screen, a speaker, and any other suitable audio and visual indicators capable of providing information to the system operator. The user interface 118 may also include input devices and controls such as an alphanumeric keyboard, a pointing device, keypads, pushbuttons, control knobs, microphones, etc., capable of accepting commands or input from the operator and transmitting the entered input to the processor 110.

Those skilled in the art will recognize that the computing environment illustrated in FIG. 3 is not intended to limit the present invention. In addition, various program code described herein may be identified based upon the application or software component within which it is implemented in a specific embodiment of the invention. However, it should be appreciated that any particular program or hardware nomenclature that follows is used merely for convenience, and thus the invention should not be limited to use solely in any specific application identified and/or implied by such nomenclature. It should be further appreciated that the various features, applications, and devices disclosed herein may also be used alone or in any combination. Moreover, given the typically endless number of ways in which computer programs may be organized into routines, procedures, methods, modules, objects, and the like, as well as the various ways in which program functionality may be allocated among various software layers that are resident within a typical computing system (e.g., operating systems, libraries, APIs, applications, applets, etc.), and/or across one or more hardware platforms, it should be appreciated that the invention is not limited to the specific organization and allocation of program or hardware functionality described herein.

Figure 4:
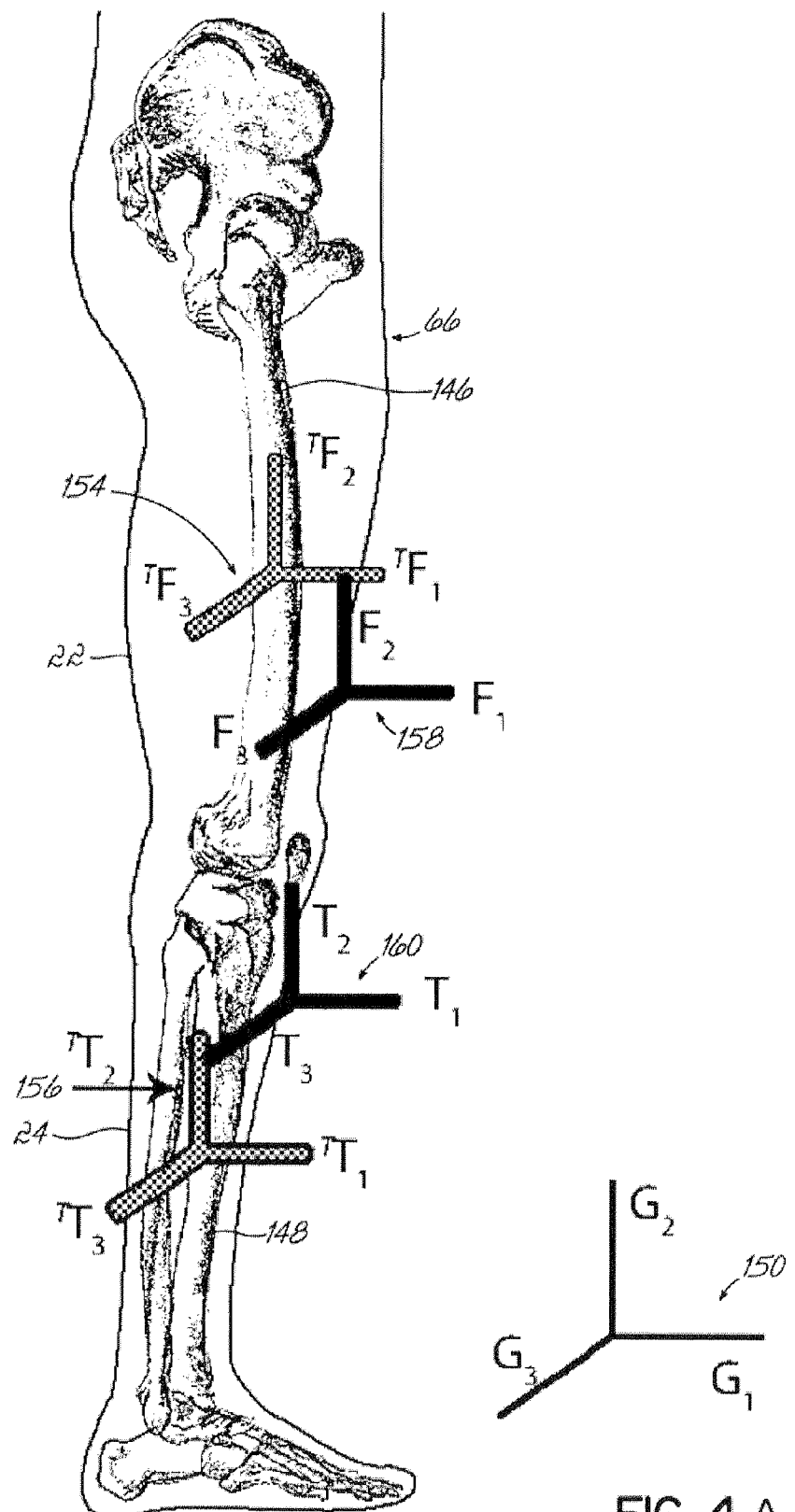
FIGS. 4A and 4B are diagrammatic views of a frame of reference and coordinate system, respectively, for use with the joint monitoring apparatus of FIG. 1.
Figure 4B:
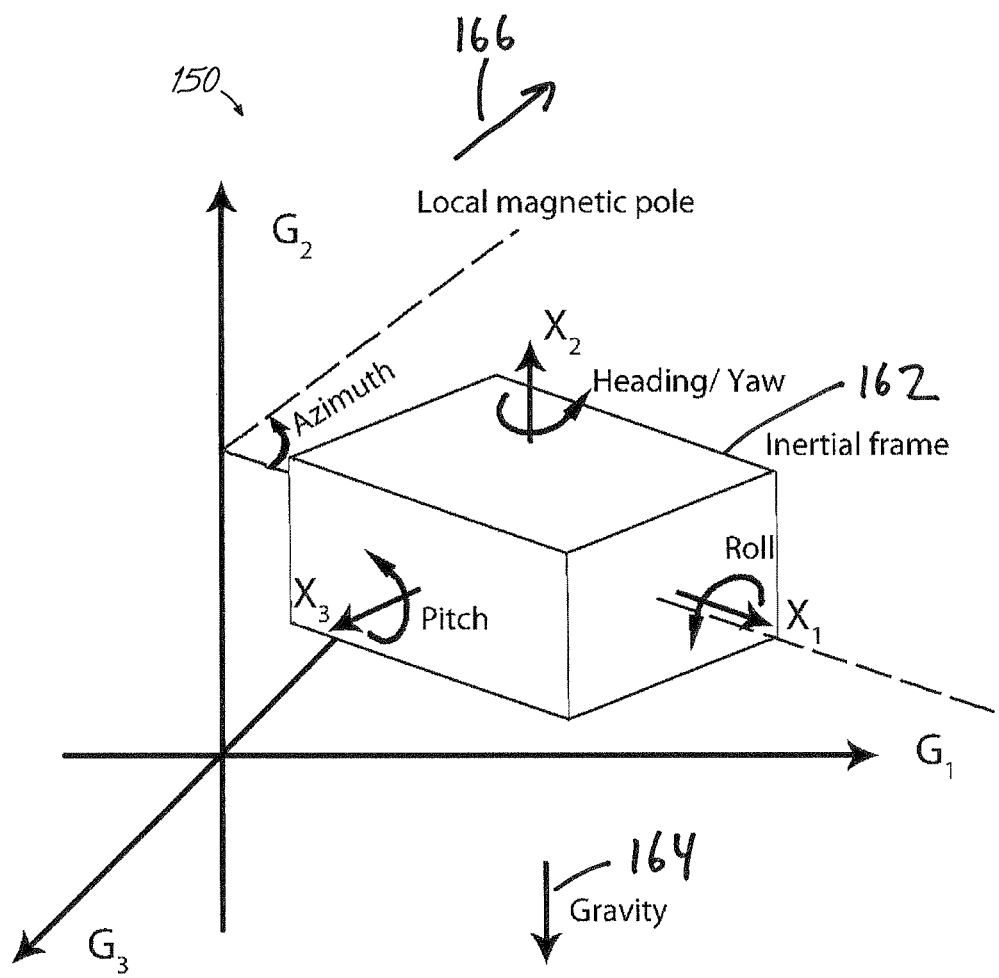

With reference now to FIGS. 4A and 4B, the fundamental principles of retrieving in vivo bone motion via the inertial monitoring unit 48 and the ultrasound transducers 40 of FIG. 2 are described in accordance with an embodiment of the invention. FIG. 4A illustrates an exemplary arrangement of the various coordinate systems of the joint monitoring apparatus 30 as used with the knee brace 32. However, persons having ordinary skill in the art will understand that other arrangements may be used, and embodiments of the invention are thus not limited to the particular arrangement shown.

A global coordinate system 150 having three axes G1, G2, G3 provides a common reference frame for the motion trackers. In an embodiment of the invention and as discussed in greater detail below, this global reference frame may be provide by gravity. As best depicted by FIGS. 1 and 4A, the two inertial monitoring units 48A, 48B of brace 32 are configured so that the femoral inertial monitoring unit 48A is secured to the patient's thigh 22 proximate the femur 146 and the tibial inertial monitoring unit 48B is secured on the shank 24 proximate the tibia 148. The inertial monitoring units 48A, 48B each have a three axis inertial coordinate system 158, 160, with the femoral IMU coordinate system 158 having three axis F1, F2, F3, and the tibial IMU coordinate system 160 having axes T1, T2, T3. The inertial monitoring units 48A, 48B are thereby configured to monitor knee joint motion of the patient 66. To this end, the output signals generated by the inertial monitoring units 48A, 48B may be referenced to the global coordinate system 150 to determine absolute motion of the femur and tibia, and/or referenced with respect to each other to determine relative motion between the femur and tibia.

Because the inertial monitoring units 48A, 48B are secured to the knee brace 32 and reside outside the patient's body, the outputs of each inertial monitoring unit 48A, 48B represents the motions of the thigh 22 and shank 24, respectively. That is, the inertial monitoring units 48A, 48B are coupled to the femur 146 and tibia 148 by regions of soft tissue forming the thigh 22 and shank 24. Thus, there may be relative motion and/or displacement between the inertial monitoring units 48A, 48B and the bones during some activities. To account for this relative motion, the positions of the bones may be monitored using the one or ultrasound transducers 40. To this end, at least one ultrasound transducer 40 may be positioned proximate to each of the patient's femur 146 and tibia 148. Similarly as described with respect to the inertial monitoring units 48A, 48B, a coordinate system 154 of the femoral ultrasound transducer 40 has three axes $^T$F1, $^T$F2, $^T$F3, and a coordinate system 156 for the tibial ultrasound transducer has three axes $^T$T1, $^T$T2, $^T$T3.

FIG. 4B illustrates the relationship between the femoral and tibial IMU coordinate systems 158, 160, which are represented by an IMU reference frame 162, and the global coordinate system 150. The global coordinate system 150 includes two reference vectors that are used to determine the orientations of the inertial monitoring units 48A, 48B. The IMU reference frame 162 has three axes X1, X2, and X3. In an embodiment of the invention, a reference vector 164 may be provided by gravity, which may be used to determine tilt angles of the static accelerometers 56. Each accelerometer 56 may have three sensing axes that are aligned with the axes X1, X2, X3 of the IMU reference frame 162. Each of these accelerometer axes X1, X2, X3 may generate an output signal indicative of the effect of the gravity vector 164 on the inertial monitoring units 48A, 48B. The tilt angles of the inertial monitoring units 48A, 48B relative to the gravity vector 164 may then be determined based on the output signal for each axis of the inertial monitoring units 48A, 48B. A second reference vector in the global coordinate system 150 may be provided by a magnetic field vector 166, which may be generated by a local magnetic pole. The azimuth of each inertial monitoring unit 48A, 48B may then be defined by an angle formed between the magnetic field vector 166 on a plane perpendicular to the gravity vector 164 and one of the axes in the IMU reference frame 162 (e.g., X1 and X3 in the illustrated embodiment).

The IMU reference frame 162 is fixed relative to the corresponding inertial monitoring unit 48A, 48B. Thus, the orientation of the IMU reference frame 162 changes relative to the global coordinate system 150 in accordance with local motion of the respective inertial monitoring unit 48A, 48B. The gyroscope 58 of the inertial monitoring unit 48A, 48B operates within the IMU reference frame 162, and responds to rotation of the inertial monitoring unit 48A, 48B. The gyroscope 58 thereby provides the joint monitoring apparatus 30 with the ability to sense and monitor rotation of each inertial monitoring unit 48A, 48B with respect to each axis of the corresponding IMU reference frame 162. As depicted in FIGS. 4A and 4B, rotation about the sensing axis X1 of the IMU reference frame 162 may be referred to as roll. Roll may correspond to abduction and adduction around axis F1 of femoral IMU coordinate system 158, and axis T1 of tibial IMU coordinate system 160, respectively. Rotation around axis X2 of the IMU reference frame 162 may be referred to as heading, or yaw. Yaw may correspond to axial rotation of the leg around femoral axis F2 of inertial monitoring unit inertial coordinate system 158 and axis T2 of tibial IMU coordinate system 160. Rotation around axis X3 of the inertial monitoring unit reference frame 162 may be referred to as pitch. Pitch may correspond to flexion and extension around axis F3 of femoral inertial monitoring unit coordinate system 158 and axis T3 of tibial inertial monitoring unit coordinate system 160, respectively.

Figure 5A:
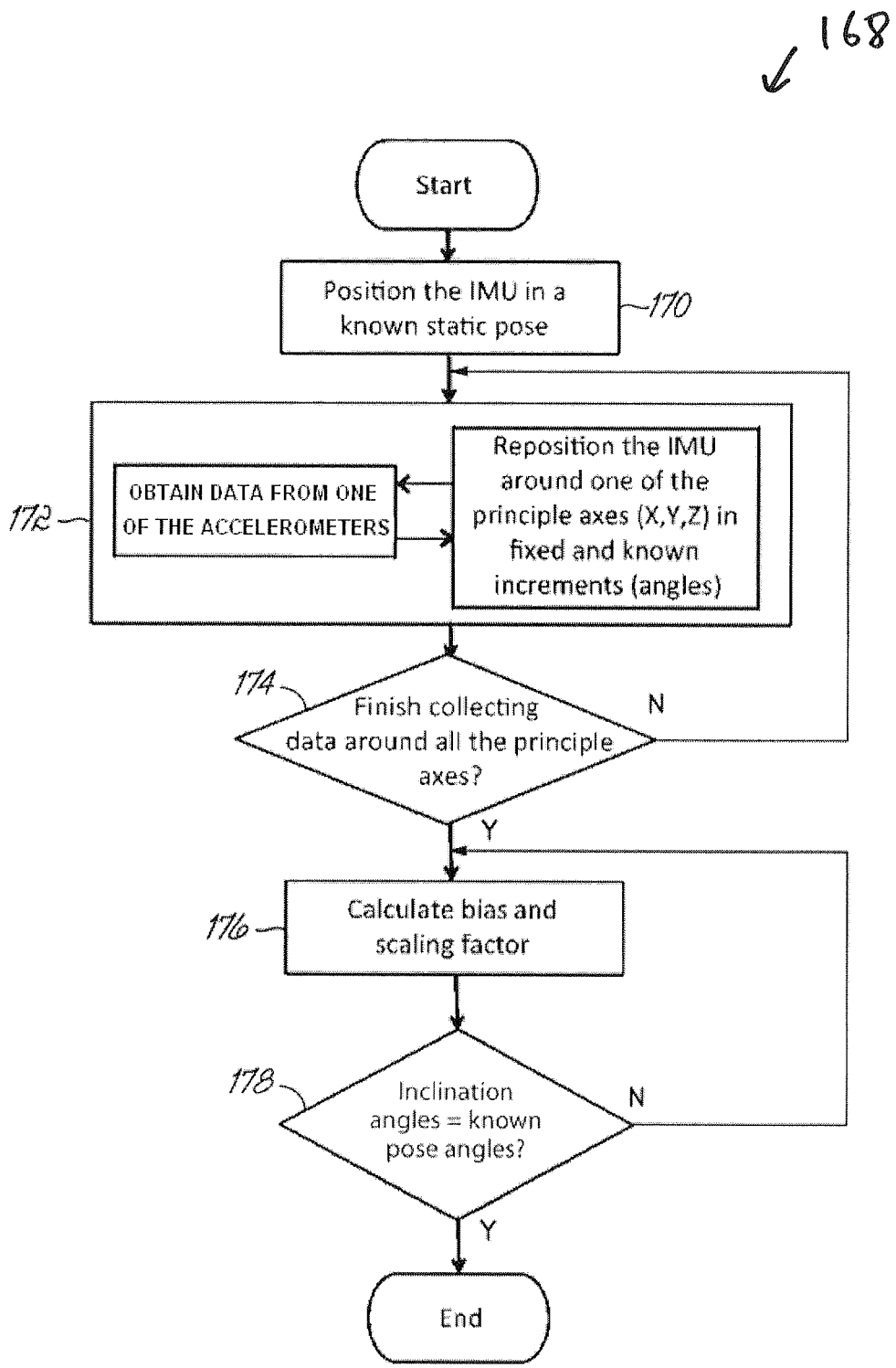
FIGS. 5A-5C are flowcharts illustrating a sequence of operations for calibrating an accelerometer, a gyroscope, and a magnetometer of the inertial monitoring unit of FIG. 2.

Referring now to FIG. 5A, a flowchart 168 illustrates an exemplary process of calibrating the accelerometer 56 of inertial monitoring unit 48A, 48B in accordance with an embodiment of the invention. Generally, the method includes positioning the inertial monitoring unit 48A, 48B in multiple fixed and known orientations around one of the axes X1, X2, X3 of the inertial monitoring unit reference frame 162. In block 170 of flowchart 168, the inertial monitoring unit 48A, 48B is placed on a rotating rate table (not shown) in an initial known static orientation, or pose. The rotating rate table is configured to rotate freely in each of the three axes X1, X2, X3 of inertial monitoring unit reference frame at known angular velocities. In block 172, data is obtained from the accelerometer 56 while the table is rotating in one or more of the three axes X1, X2, X3. Once data has been obtained with the inertial monitoring unit 48A, 48B in the initial pose, the inertial monitoring unit 48A, 48B may be repositioned around one of the axes X1, X2, X3 at fixed and known increments (e.g., degrees or radians). Data is then obtained from the accelerometer 56 with the inertial monitoring unit 48A, 48B in the new position as previously described.

In block 174, if insufficient data has been collected around each of the axis X1, X2, X3, ("No" branch of decision block 174), the process of incrementally repositioning the inertial monitoring unit 48A, 48B and collecting data is repeated. If sufficient data has been collected around each axis X1, X2, X3 ("Yes" branch of decision block 174), the method proceeds to block 176. In block 176, bias and scaling factors are calculated for, and applied to the data obtained from the accelerometer 56. In block 178, the inclination angles of the inertial monitoring unit 48A, 48B are determined with the applied bias and scaling factors. These inclination angles are then compared to the known pose angles. If the determined inclination angles correspond sufficiently with the known pose angles ("Yes" branch of block 178), the applied bias and scaling factors are set and the process ends. If the determined inclination angles differ significantly from the known pose angles ("No" branch of decision block 178), the method returns to block 176, and the bias and scaling factors for the inertial monitoring unit 48A, 48B are recalculated.

Thus, the process may be repeated until the measured inclination angles correspond sufficiently with the known pose angles.

Figure 5B:
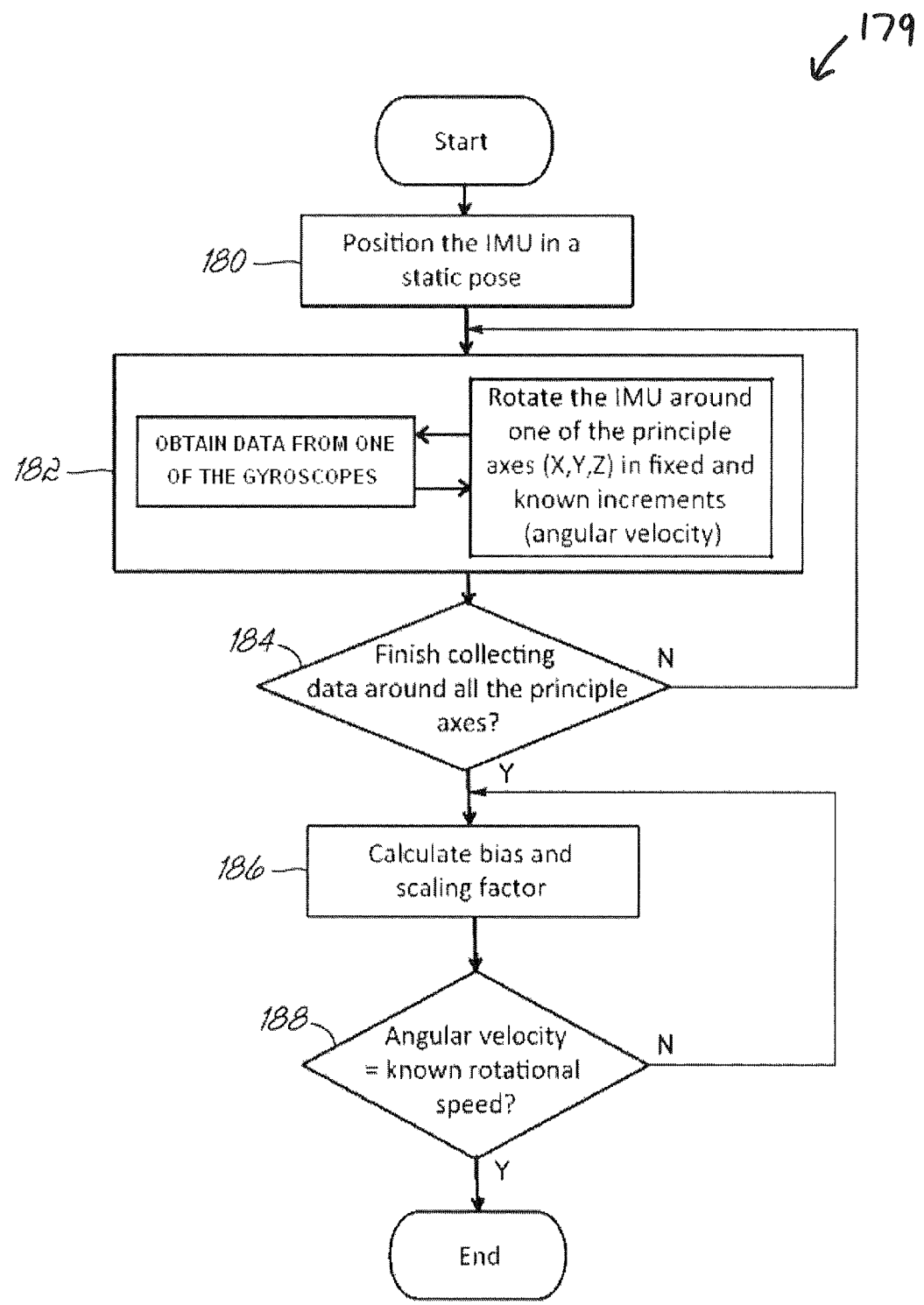

Referring now to FIG. 5B, a flow chart 179 illustrates an exemplary calibration process for the gyroscope 58 of inertial monitoring unit 48A, 48B in accordance with an embodiment of the invention. Similarly as described above, in block 180 of flowchart 179 the inertial monitoring unit 48A, 48B is placed on the rotating rate table in a known static pose. In block 182, data is obtained from the gyroscope 58 while the rate table is rotating in one or more of the three axes X1, X2, X3 at a known angular velocity. Data is thereby obtained from the gyroscope 58 with the inertial monitoring unit 48A, 48B moving at a plurality of angular velocities and in each of the axes X1, X2, X3.

In block 184, if insufficient data has been collected ("No" branch of decision block 184), the angular velocity is incremented and the process of rotating the inertial monitoring unit 48A, 48B and collecting data is repeated. If sufficient data has been collected ("Yes" branch of decision block 184), the method proceeds to block 186. In block 186, bias and scaling factors are calculated for, and applied to the data obtained from the gyroscope 58. In block 188, the angular velocity of the inertial monitoring unit 48A, 48B is determined with the applied bias and scaling factors. The determined angular velocity is then compared to the known angular velocity. If the determined angular velocities correspond sufficiently with the known angular velocities ("Yes" branch of block 188), the applied bias and scaling factors are set and the process ends. If the determined angular velocities differ significantly from the known angular velocities ("No" branch of decision block 188), the method returns to block 186, and the bias and scaling factors for the inertial monitoring unit 48A, 48B are recalculated. Thus, the process may be repeated until the determined angular velocities correspond sufficiently with the known angular velocities.

Figure 5C:
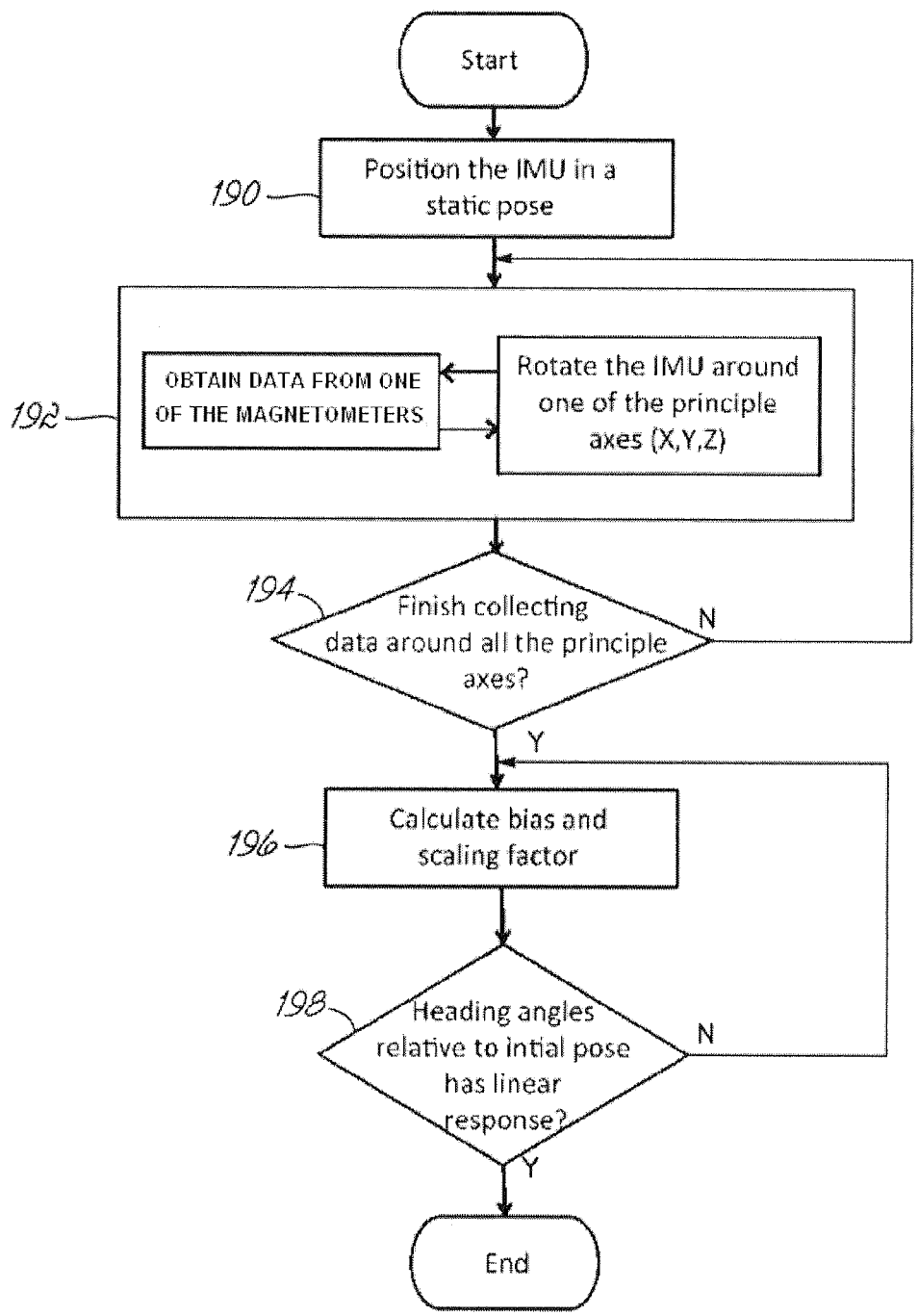

Referring now to FIG. 5C, flow chart 189 illustrates an exemplary process for calibrating the magnetometer 60 of inertial monitoring unit 48A, 48B. In block 190 of flowchart 189 the inertial monitoring unit 48A, 48B is placed on the rotating rate table in a known static pose. In block 192, data is obtained from the magnetometer 60 while the rate table is rotating in one of the three axes X1, X2, X3 at a known fixed angular velocity in the presence of the magnetic vector 166. Data is then obtained from the magnetometer 60 with the inertial monitoring unit 48A, 48B moving at a known angular velocity in the axis X1, X2, X3 in question.

In block 194, if data has not been collected for each of the axes X1, X2, X3 ("No" branch of decision block 194), the process of rotating the inertial monitoring unit 48A, 48B and collecting data is repeated for another axis X1, X2, X3 of the IMU reference frame 162. If data has been collected for each axis X1, X2, X3 ("Yes" branch of decision block 194), the method proceeds to block 196. In block 196, bias and scaling factors are calculated for and applied to the data obtained from the magnetometer 60. In block 198, heading angles of the inertial monitoring unit 48A, 48B are determined with respect to the initial pose using the applied bias and scaling factors. If the heading angles have a linear response, ("Yes" branch of block 198), the applied bias and scaling factors are set and the process ends. If the heading angles do not have a linear response ("No" branch of decision block 188), the calibration process returns to block 196, and the bias and scaling factors for the magnetometer 60 are recalculated. Thus, the process may be repeated until the heading angles have a sufficiently linear response to rotation.

Figure 6A:
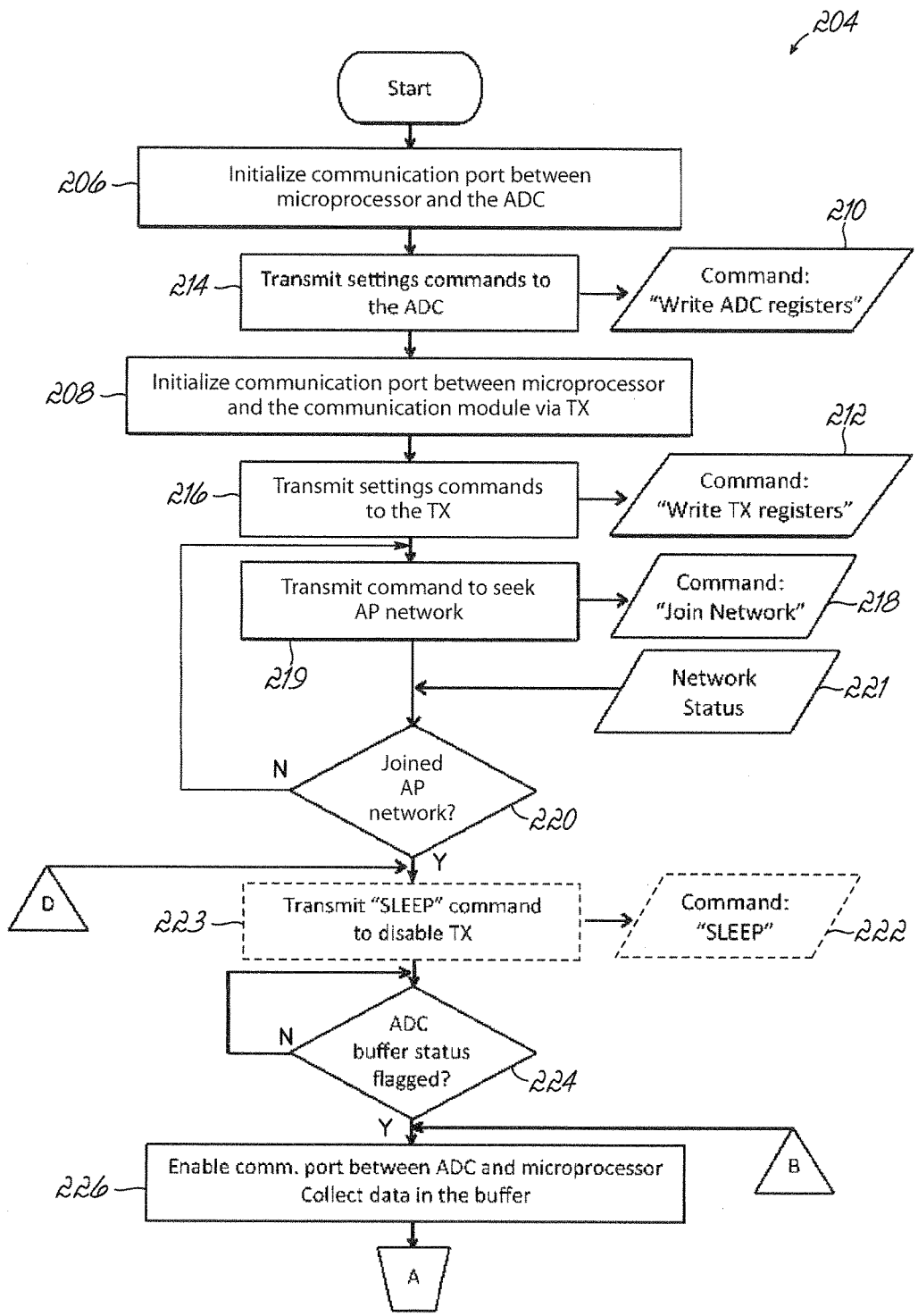
FIGS. 6A and 6B are flowcharts illustrating a sequence of instructions for operation of the inertial monitoring unit in FIG. 2.
Figure 6B:
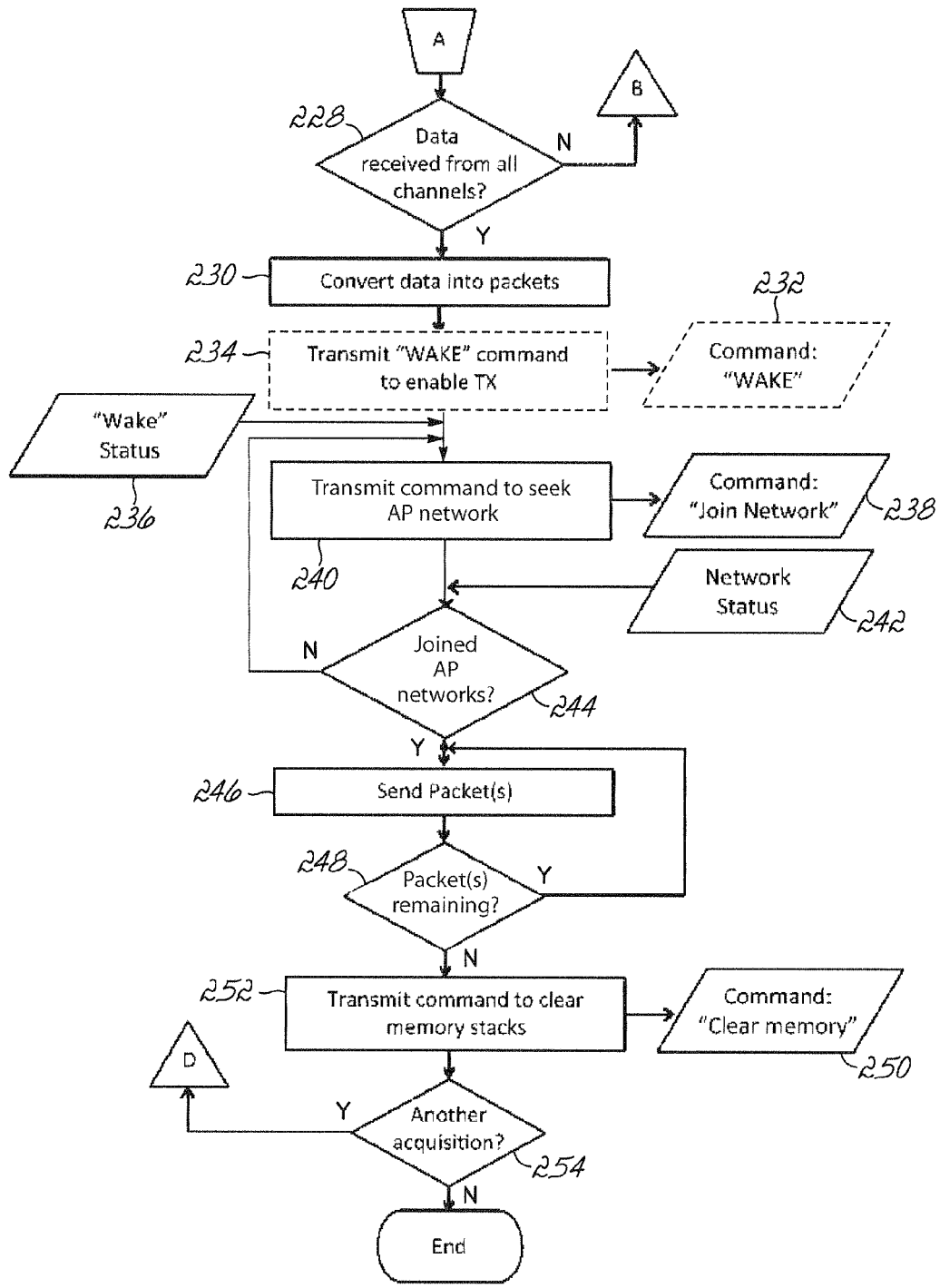

Referring now to FIGS. 6A and 6B, a flowchart 204 illustrates a firmware instruction flow of the processor 72 of inertial monitoring unit 48 in accordance with an embodiment of the invention. The calibrated joint monitoring apparatus 30 may be used to monitor, for example, movement of the patient's knee. To this end, in response to the joint monitoring apparatus 30 being powered up, the processor 72 may proceed to block 206 and initialize a communication port coupled to the ADC 64. The processor 72 may then proceed to block 214 and transmit commands to the ADC 64. These commands may include proceeding to block 210 and transmitting a "write ADC registers" command to configure the settings of the ADC 64.

The processor 72 may then proceed to block 208 and initialize a communication port between the processor 72 and the communication module 70 by proceeding to block 216 and transmitting a "write TX registers" command to configure the settings of the communication module 70 in block 212. A verification command may also be sent to both the ADC 64 and communication module 70 to verify that the ports, the ADC 64, and the communication module 70 are functioning properly.

The processor 72 may then proceed to block 219. In block 219, the processor 72 may transmit a command seeking an access point (AP), such as for connecting to the network 122 or computer 54. The command (Block 218) is then sent to seek the AP that includes a receiver ("RX") operating at the same bandwidth as the TX associated with the inertial monitoring units 48A, 48B band of the computer 54 (Block 219). If an AP is found ("Yes" branch of block 220) as determined by the network status (Block 221), then the process continues; otherwise ("No" branch of block 220), the process returns to identify an available AP.

In response to the AP being found within the range of inertial monitoring units 48A, 48B, an optional sleep command (Block 222) may be sent to disable the TX and to conserve power when the ADC 64 operates (Block 223). When the ADC 64 has converted the analog sensor signal from one of its channels to a digital signal ("Yes" branch of block 224), then a notification signal may be sent to the processor 72 to indicate that data is ready at the ADC buffer. In response to receiving the notification signal, the processor 72 may enable the communication port between the ADC 64 and the processor 72. The processor 72 may then collect data from the ADC 64 (Block 226). In block 230, after all data has been read from the ADC 64 into the processor 72 ("Yes" branch of block 228), the processor 72 may place the data into a message array and convert the message array into a plurality of packets. The packets may then be transmitted to the communication module 70 for transmission to the computer through the AP.

If necessary, the processor 72 may proceed to Block 232 and transmit a "wake" command to wake and enable the communication module 70. Once a wake status (Block 236) is received, a command (Block 238) is transmitted to join the AP network (Block 240). When the network status (Block 242) indicates that the AP network has been joined ("Yes" branch of block 244), then the packets are sent (Block 246). In response to determining that packets remain to be transmitted ("No" branch of block 248), the processor 72 may continue transmitting packets. Thus, the processor 72 may continue transmitting packets until no packets remain. A "clear memory" command (Block 250) may then be sent to clear the memory stacks (Block 252) of the processor 72. Optionally, the processor 72 may then be disabled while waiting for notification of another acquisition ("Yes" branch of block 254), otherwise ("No" branch of block 254), the process ends.

Figure 7:
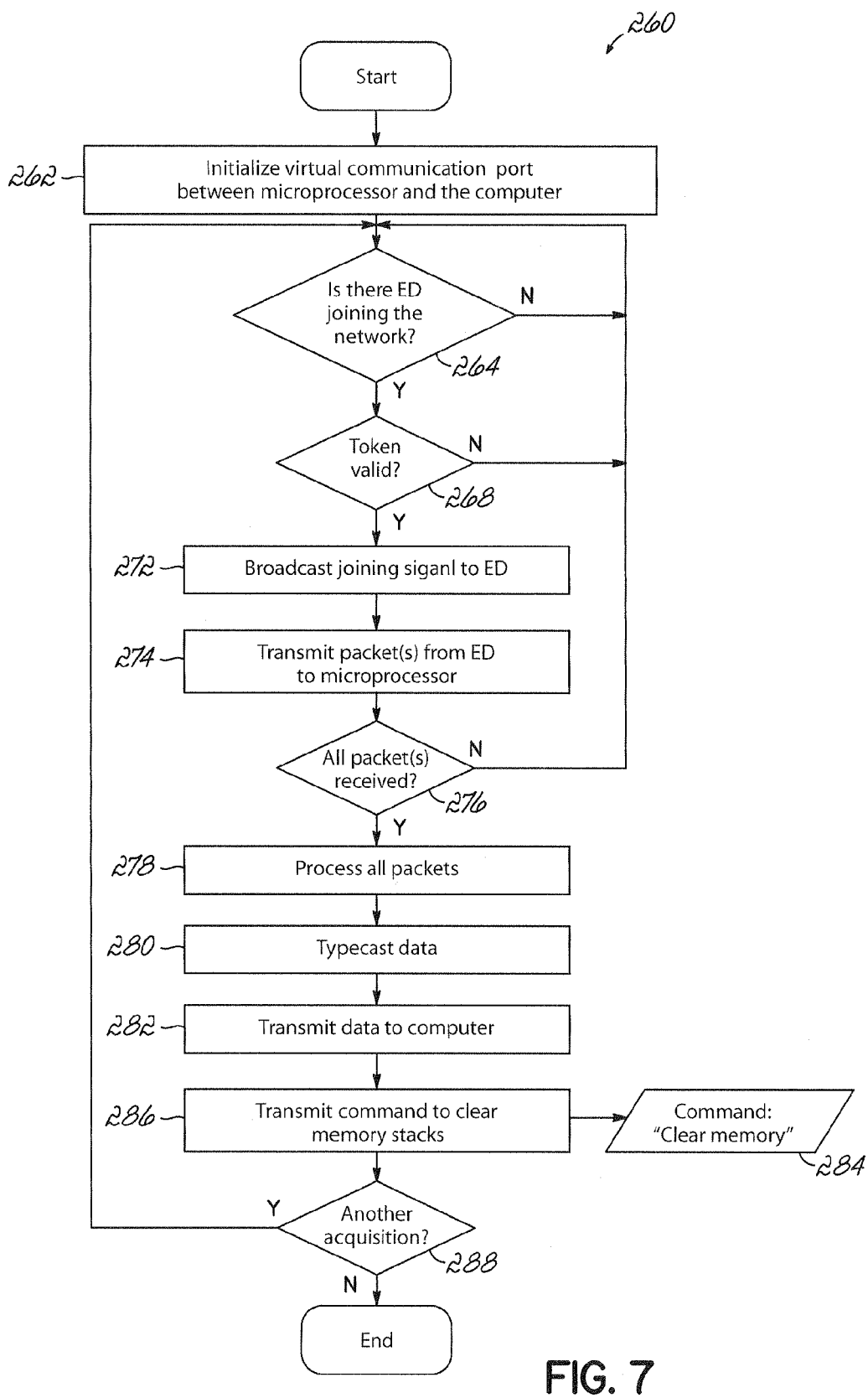
FIG. 7 is a flowchart illustrating a sequence of instructions for operating a wireless receiving unit that receives data from the inertial monitoring unit in FIG. 2 and transmits the data to the computer in FIG. 3.

FIG. 7 presents a flowchart 260 illustrating a set of instructions that may be executed by the processor 72 for connecting to the access point. The access point receiver may be connected directly into the computer 54, connect to the computer 54 via a cable and be powered by the computer connection, or be coupled to the computer through the network 122. After power up, the processor 72 initiates a communication port between the processor and the computer 54 via the access point (Block 262). The receiver listens for end devices ("ED") to join the network (Block 264), wherein the EDs may be the wireless enabled inertial monitoring units 48A, 48B, the vibration module 50, and/or ultrasound module 52. When an ED seeking the AP comes within the range of the RX network ("Yes" branch of decision block 264), the processor 72 will query as to the validity of a token received from the ED seeking signal (Block 268). If the token is valid ("Yes" branch of decision block 268), then a joining signal is broadcast to the ED (Block 272). If the token is invalid ("No" branch of decision block 268), and/or no ED seeks joinder ("No" branch of decision block 264), then the process may repeat.

The AP listens for a first frame of an incoming data packet (Block 274). After the first frame of the data packet has been received, the processor 72 will continue to receive and to store all the data packets in memory ("Yes" branch of decision block 276) or the AP will continue awaiting for an incoming data packet ("No" branch of decision block 276). The received packets are processed (Block 278), typecast (Block 280) and transmitted (Block 282) to the computer 54. A command (Block 284) is sent to clear the memory stacks (Block 286) of the processor 72. The processor 72 then waits for a notification that another ED has joined the network ("Yes" branch of block 288), otherwise ("No" branch of block 288), the process ends.

Figure 8:
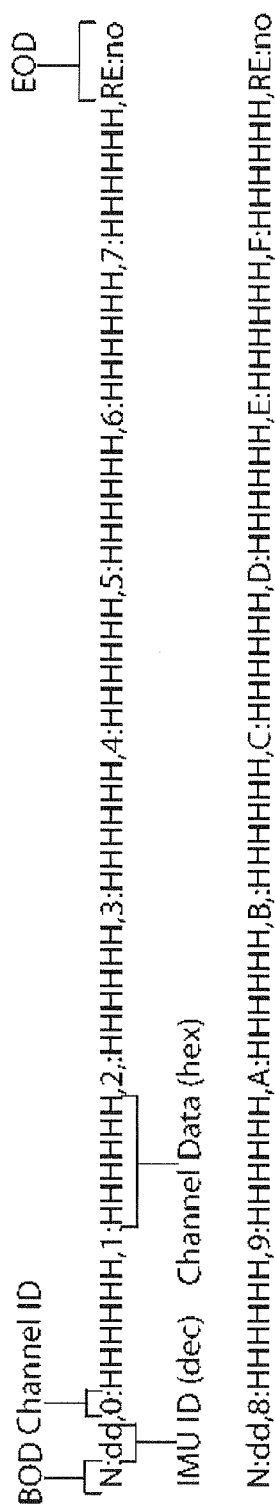
FIG. 8 is a diagrammatic view of a data transmission protocol for use with the sequence of operating instructions of FIG. 7.

FIG. 8 demonstrates an exemplary data format, which includes a beginning of data ("BOD") tag, including "N:" followed by a two digit decimal inertial monitoring unit tag ID. The data from each channel consists of a single digit number channel tag in hexadecimal format, and the channel data in a six digit hexadecimal number. The end of data ("EOD") tag indicates the end of the transmission of one set of data received from the packet.

Figure 9:
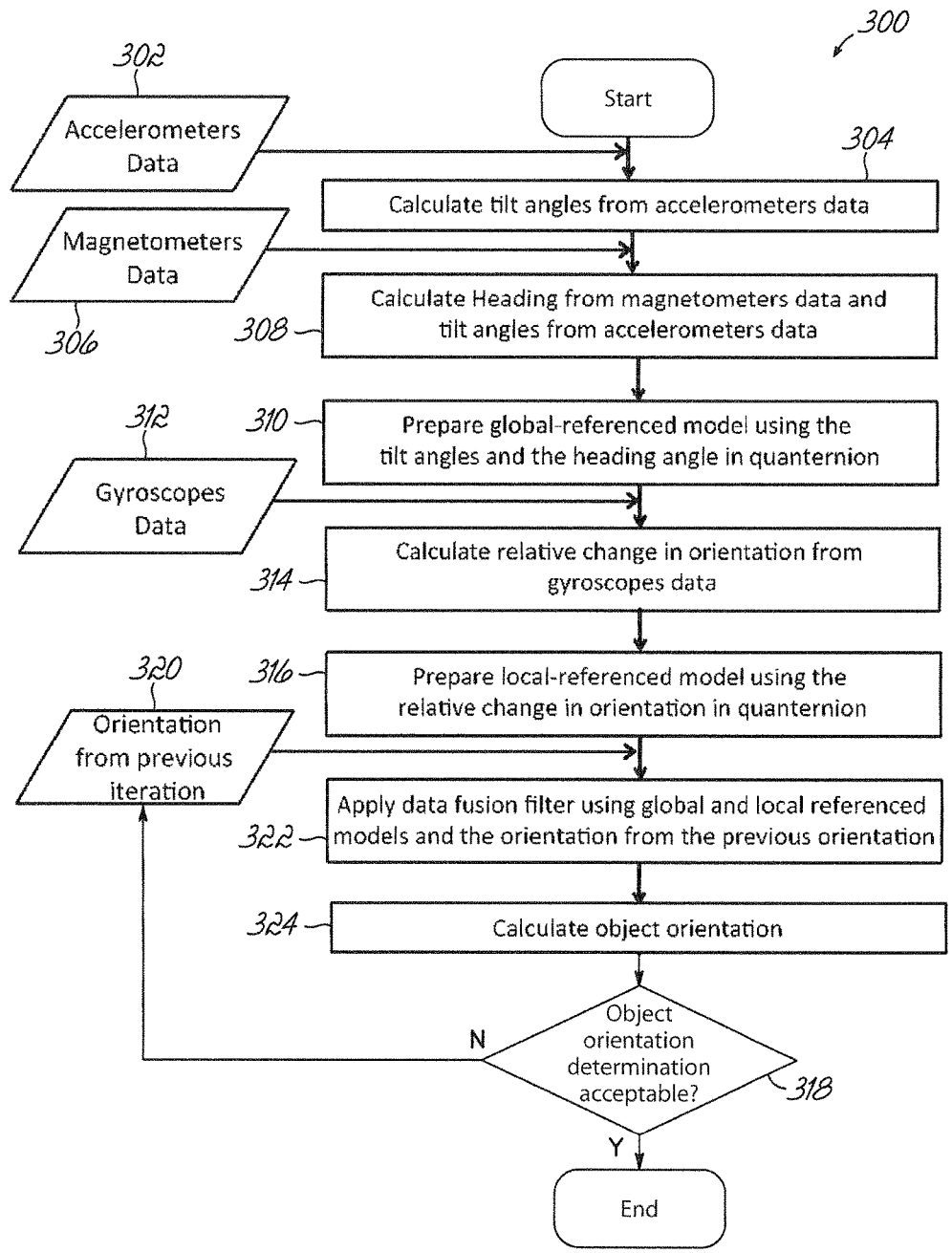
FIG. 9 is a flowchart illustrating a sequence of instructions for calculating an object orientation from the data received from the inertial monitoring unit of FIG. 2.

Turning now to FIG. 9, a flowchart 300 illustrating a software based motion tracking algorithm for the inertial monitoring unit 48A, 48B is provided in accordance with an embodiment of the invention. Generally, an object's orientation may be determined using a discrete linear dynamic model, wherein the transition between a current state at a current time, k, and a previous state at a previous time, k−1, is described by:

$$x_k = Ax_{k-1} + Bu_{k-1} + W_{k-1} \quad (1)$$

where $x_k$ is the state vector of the current state, $x_{k-1}$ is the state vector from the previous state, A is the transitional matrix model to transform the previous state into the current state, B is the matrix model for controlled input $u_{k-1}$ from the previous state, and $w_{k-1}$ is the process noise, which is independent with zero means normal probability with process noise covariance matrix Q.

$$p(w) = N(0,Q) \quad (2)$$

The model that relates the measurement to the state vector $x_k$ of the system at time k is:

$$z_k = H x_k + h_k \quad (3)$$

where $z_k$ is the measurements vector at time k, H is the matrix of measurement equations that relates the state $x_k$ to $z_k$, and $v_k$ is the measurement noise at time k, which is independent with zero means normal probability with measurement noise covariance matrix R.

$$p(v) = N(0,R) \quad (4)$$

As the same vector at different instances is needed for the calculation, the following parameters are defined: $\hat{x}_k^-$ is the a priori estimation of the state at the current time k, with the knowledge resultant from the process that occurs prior to the current time k; $\hat{x}_k$ is the a posteriori estimation of the state at the current time k, given the measurement of $z_k$. The errors for the a priori and the a posteriori estimations are:

$$e_k^- = x_k - \hat{x}_k^- \quad (5)$$

$$e_k = x_k - \hat{x}_k \quad (6)$$

The error covariance matrixes for the a priori and the a posteriori estimations may then be determined as:

$$P_k^- = E[e_k^- e_k^{-T}] \quad (7)$$

$$P_k = E[e_k e_k^T] \quad (8)$$

The essence of the Kalman filter is to determine the differences between the calculated estimations and the actual measurements, and to responsively adjust the filter accordingly. In use, the difference between the a priori estimation $H\hat{x}_k^-$, and the measurement $z_k$, may be determined with the innovation matrix:

$$\tilde{y}_k = z_k - H\hat{x}_k^- \quad (9)$$

where $\tilde{y}_k$ is the innovation matrix.

The innovation error covariance matrix $S_k$, determines residual error between $H\hat{x}_k^-$ and $z_k$:

$$S_k = H P_k^- H^T + R \quad (10)$$

The a posteriori state estimate $\hat{x}_k$, is then a linear combination of the a priori estimate $\hat{x}_k^-$, and a weighted innovation adjustment.

$$\hat{x}_k = \hat{x}_k^- + K_k \tilde{y}_k \quad (11)$$

where $K_k$ is the optimal Kalman gain, the latter of which may be determined by minimizing the a posteriori estimate covariance matrix. The a posteriori error covariance $P_k$ is given as:

$$P_k = cov(x_k - \hat{x}_k) \quad (12)$$

Expanding the a posteriori estimate covariance matrix with the equations from the measurement model, innovation, and the posteriori state estimate yields:

$$P_k = cov(x_k - (\hat{x}_k^- + K_k(Hx_k + v_k - H\hat{x}_k^-))) \quad (13)$$

Because the a priori estimate is an invariant, its process noise cannot be correlated with the other parameters, and has zero means normal probability with process noise covariance matrix R. The equation thus becomes:

$$P_k = (I - K_k H_k) P_k^- (I - K_k H_k)^T + K_k R_k K_k^T = P_k^- - K_k H_k P_k^- - P_k^- H_k^T K_k^T + K_k S_k K_k^T \quad (14)$$

The optimal Kalman gain minimizes the a posteriori error covariance estimate to zero. By setting the derivative of the posteriori estimate $P_k$ with respect to the optimal Kalman gain $K_k$ equal to zero, the optimal Kalman gain $K_k$, may be determined by:

$$\frac{\partial P_k}{K_k} = 0 = 2(-(H_k P_k^-)^T + K_k S_k) \quad (15)$$

$$K_k = P_k^- H_k^T S_k^{-1} \quad (16)$$

The Kalman filter may be separated into 2 major sets of equations: (1) the time update equations; and (2) the measurements update equations. The time update equations predict the a priori estimate at the current time k, with the knowledge of the current state and the error covariance at the previous time k−1.

$$\hat{x}_k^- = A\hat{x}_{k-1} + Bu_{k-1} \quad (17)$$

$$P_k^- = AP_{k-1}A^T + Q \quad (18)$$

The measurements update equations use the measurements acquired with the a priori estimates to calculate the a posteriori estimates:

$$S_k = HP_k^- H^T + R \qquad (19)$$

$$K_k = P_k^- H_k^T S_k^{-1} \qquad (20)$$

$$\hat{x}_k = \hat{x}_k^- + K_k \tilde{y}_k, \tilde{y}_k = z_k - H\hat{x}_k^- \qquad (21)$$

$$P_k = (I - K_k H_k) P_k^- \qquad (22)$$

The a posteriori estimate is then used to predict the a priori estimate at the next time state and next time interval. As displayed from the equations above, no further information, other than the current state and the error covariance in the current state with respect to the previous state, is required.

By assuming the inertial monitoring unit 48A, 48B is a linear dynamic system, the position and the orientation of the inertial monitoring unit 48A, 48B may be determined. That is, the positioning of inertial monitoring unit 48A, 48B may be calculated via summing the displacement on each axis during each time interval iteration. The relative translation of the inertial monitoring unit 48A, 48B from its initial position may be obtained using transition model $x_k = Ax_{k-1} + Bu_{k-1} + W_{k-1}$, which becomes:

$$\begin{bmatrix} vx_k \\ vy_k \\ vz_k \\ sx_k \\ sy_k \\ sz_k \end{bmatrix} = \begin{bmatrix} 1 & 0 & 0 & 0 & 0 & 0 \\ 0 & 1 & 0 & 0 & 0 & 0 \\ 0 & 0 & 1 & 0 & 0 & 0 \\ \Delta t & 0 & 0 & 1 & 0 & 0 \\ 0 & \Delta t & 0 & 0 & 1 & 0 \\ 0 & 0 & \Delta t & 0 & 0 & 1 \end{bmatrix} \begin{bmatrix} vx_{k-1} \\ vy_{k-1} \\ vz_{k-1} \\ sx_{k-1} \\ sy_{k-1} \\ sz_{k-1} \end{bmatrix} + \begin{bmatrix} \Delta t & 0 & 0 \\ 0 & \Delta t & 0 \\ 0 & 0 & \Delta t \\ \Delta t^2/2 & 0 & 0 \\ 0 & \Delta t^2/2 & 0 \\ 0 & 0 & \Delta t^2/2 \end{bmatrix} \begin{bmatrix} ax_{k-1} \\ ay_{k-1} \\ az_{k-1} \end{bmatrix} \qquad (23)$$

The measurement model $z_k = Hx_k + h_k$ becomes:

$$\begin{bmatrix} vx_{k+1} \\ vy_{k+1} \\ vz_{k+1} \\ sx_{k+1} \\ sy_{k+1} \\ sz_{k+1} \end{bmatrix} = \begin{bmatrix} 1 & 0 & 0 & 0 & 0 & 0 \\ 0 & 1 & 0 & 0 & 0 & 0 \\ 0 & 0 & 1 & 0 & 0 & 0 \\ 0 & 0 & 0 & 1 & 0 & 0 \\ 0 & 0 & 0 & 0 & 1 & 0 \\ 0 & 0 & 0 & 0 & 0 & 1 \end{bmatrix} \begin{bmatrix} vx_k \\ vy_k \\ vz_k \\ sx_k \\ sy_k \\ sz_k \end{bmatrix} + h_k \qquad (24)$$

Orientation tracking, similar to positional tracking, may be determined by summing the angle of rotation on each axis for each incremental time interval. The transformation from one orientation to another may be expressed in terms of a rotation matrix RM:

$$RM = \begin{bmatrix} 1 & 0 & 0 \\ 0 & \cos(\rho) & \sin(\rho) \\ 0 & -\sin(\rho) & \cos(\rho) \end{bmatrix} \begin{bmatrix} \cos(\varphi) & 0 & -\sin(\varphi) \\ 0 & 1 & 0 \\ \sin(\varphi) & 0 & \cos(\varphi) \end{bmatrix} \begin{bmatrix} \cos(\theta) & \sin(\theta) & 0 \\ -\sin(\theta) & \cos(\theta) & 0 \\ 0 & 0 & 1 \end{bmatrix}$$

$$= \begin{bmatrix} \cos(\varphi)\cos(\theta) & -\cos(\rho)\sin(\theta) + \sin(\rho)\sin(\varphi)\cos(\theta) & \sin(\rho)\sin(\theta) + \cos(\rho)\sin(\varphi)\cos(\theta) \\ \cos(\varphi)\sin(\theta) & \cos(\rho)\cos(\theta) + \sin(\rho)\sin(\varphi)\sin(\theta) & -\sin(\rho)\cos(\theta) + \cos(\rho)\sin(\varphi)\sin(\theta) \\ -\sin(\varphi) & \sin(\rho)\cos(\varphi) & \cos(\rho)\cos(\theta) \end{bmatrix} \qquad (25)$$

where $\rho$, $\phi$, and $\theta$ are the Euler angles for pitch, roll, and yaw, respectively. The rotational matrix RM may be considered to be the time update within the measurement model of the Kalman filter as it transforms the orientation of the inertial monitoring unit 48A, 48B from the previous orientation to the current orientation. The transitional matrix in the prediction step of the Kalman filter may be the attitude dynamic model:

$$\begin{bmatrix} \rho_{k+1} \\ \varphi_{k+1} \\ \theta_{k+1} \end{bmatrix} = \left( \begin{bmatrix} 1 & 0 & 0 \\ 0 & 1 & 0 \\ 0 & 0 & 1 \end{bmatrix} + \begin{bmatrix} w_x & 0 & 0 \\ 0 & w_y & 0 \\ 0 & 0 & w_z \end{bmatrix} \cdot \Delta t \right) \begin{bmatrix} \rho_k \\ \varphi_k \\ \theta_k \end{bmatrix} \qquad (26)$$

Orientation tracking requires the use of multiple sensors, i.e., one or more of the accelerometer 56, the gyroscope 58, and the magnetometer 60. Depending on the strengths and weaknesses of each sensor, the data from that respective sensor may be used in a different portion of the model. For example, data collected from the gyroscope 58 may be used in the prediction model as it provides rotational information within the inertial frame and because quadrant transitions do not affect the measurement generated by the gyroscope 58. On the other hand, each of the accelerometer 56 and the magnetometer 60 use an external reference for generating orientation measurements, which may create a more stable signal that is not as susceptible to arithmetic drift as compared with the gyroscope 58. Therefore, the data generated by the accelerometer 56 and the magnetometer 60 may be used to verify the measurement model and to act as a control for gyroscopic drift.

Angular velocities may be obtained by calculating the time derivative of the Euler angles:

$$\begin{bmatrix} w_x \\ w_y \\ w_z \end{bmatrix} = \begin{bmatrix} 1 & 0 & -\sin(\varphi) \\ 0 & \cos(\rho) & \cos(\varphi)\sin(\rho) \\ 0 & -\sin(\rho) & \cos(\varphi)\cos(\rho) \end{bmatrix} \begin{bmatrix} \dot{\rho} \\ \dot{\varphi} \\ \dot{\theta} \end{bmatrix} \qquad (27)$$

Therefore, the relationship between the change in the Euler angles and the angular velocities becomes:

$$\begin{bmatrix} \dot{p} \\ \dot{\varphi} \\ \dot{\theta} \end{bmatrix} = \begin{bmatrix} 1 & \dfrac{\sin(\varphi)\sin(\rho)}{\cos(\varphi)} & \dfrac{\sin(\varphi)\cos(\rho)}{\cos(\varphi)} \\ 0 & \cos(\rho) & -\sin(\rho) \\ 0 & \sin\dfrac{(\rho)}{\cos(\varphi)} & \dfrac{\cos(\rho)}{\cos(\varphi)} \end{bmatrix} \begin{bmatrix} w_x \\ w_y \\ w_z \end{bmatrix} \quad (28)$$

The above relationship suggested that singularity occurs at angles equal to π or 3π/2, such as when two of sensing axes are positioned parallel to one another, which creates a mathematical Gimbal lock from the calculation. To overcome the disadvantage of the trigonometry Gimbal lock, another representation of orientation may be used. According to Euler's theorem of rotation, any spatial rotation of a rigid body in three-dimensional space may be written as a rotation around an axis. A quaternion is a 4 dimensional vector that consists of one scalar part and three orthogonal imaginary components, and is defined as:

$$q = q_0 + q_1 i + q_2 j + q_3 k \quad (29)$$

Rotation of a rigid body in 3D space may be expressed in quaternion form as:

$$q = \cos\frac{\beta}{2} + \gamma_1 \sin\frac{\beta}{2} i + \gamma_2 \sin\frac{\beta}{2} j + \gamma_3 \sin\frac{\beta}{2} k \quad (30)$$

where rotation occurs at an angle, β, around a vector, $\gamma(\gamma_1, \gamma_2, \gamma_3)$. Rotation of the rigid body between 2 reference frames may be evaluated as:

$$\tau' = q\tau\bar{q} \quad (31)$$

Where τ and τ' are the initial and final positions expressed in quaternion form with a zero scalar component between the two frames:

$$\bar{q} = q_0 - q_1 i - q_2 j - q_3 k \quad (32)$$

where $\bar{q}$ is the conjugate of q.

The quaternion form has a unique property in that the length of the quaternion should be equal to 1.

$$q \cdot q = \sqrt{(q_0)^2 + (q_1)^2 + (q_2)^2 + (q_3)^2} = 1 \quad (33)$$

The quaternion is a third order, hypercomplex number to which traditional algebra does not apply. Thus, multiplication of two quaternions is non-commutative, as shown:

$$q + p \to p \otimes q = \begin{bmatrix} p_0 q_0 & -p_1 q_1 & -p_2 q_2 & -p_3 q_3 \\ p_1 q_0 & p_0 q_2 & p_2 q_3 & -p_3 q_2 \\ p_2 q_0 & p_0 q_2 & p_3 q_1 & -p_1 q_3 \\ p_3 q_0 & p_0 q_3 & p_1 q_2 & -p_2 q_1 \end{bmatrix} \quad (34)$$

$$q - p \to p^{-1} \otimes q,\ p^{-1} = \frac{conj(p)}{|p|^2} \quad (35)$$

$$e = \sum W_i(s_i - m_{k-1}) \quad (36)$$

$$m_k = m_{k-1} - e \quad (37)$$

$$e = \sum W_i \log(m_{k-1}^{-1} \otimes s_i) \quad (38)$$

$$m_k = m_{k-1} \exp(e) \quad (39)$$

In use, data is received from the accelerometer 56 in block 302 of flowchart 300, and the received data is processed to compensate the scale and bias in accordance with the calibration, for example, as was determined according to the process shown in FIG. 5A. Accordingly, the tilt angles of the inertial monitoring unit 48A, 48B may be calculated (Block 304). Data from the magnetometer 60 may then be received (Block 306) and processed to compensate the scale and bias in accordance with the calibration, for example, as determined according to the process shown in FIG. 5B. The heading from the magnetometer data is calculated (Block 308) and used with the tilt angles, determined from the accelerometer data, to calculate the azimuth (FIG. 4B).

Using the heading from the magnetometer data and the tilt angles from the accelerometer data, in quaternion, along with the determined azimuth, a global orientation reference model may be prepared. (Block 310). Determination of the global orientation may be related to the global constraints, including, for example, gravity and the local magnetic field.

Data from the gyroscope 58 is then received (Block 312) and may be processed to compensate the scale and bias in accordance with the calibration, for example, as determined according to the process shown in FIG. 5C. The relative change in orientation is calculated based on the angular velocities from the gyroscope 58 (Block 314) and a local referenced model prepared using the relative change in orientation in the quanternion (Block 316). A feedback loop (Block 318) containing data (Block 320), such as error estimates from a previous iteration, may be used in applying a data fusion filter along with the global and local orientation models to minimize the system noise, and eliminate orientation ambiguity of the sensors (Block 322). The object orientation (here, the knee as indicated with the knee brace 32) is determined by the associated orientation of the inertial monitoring unit 48A, 48B (Block 324).

Figure 10A:
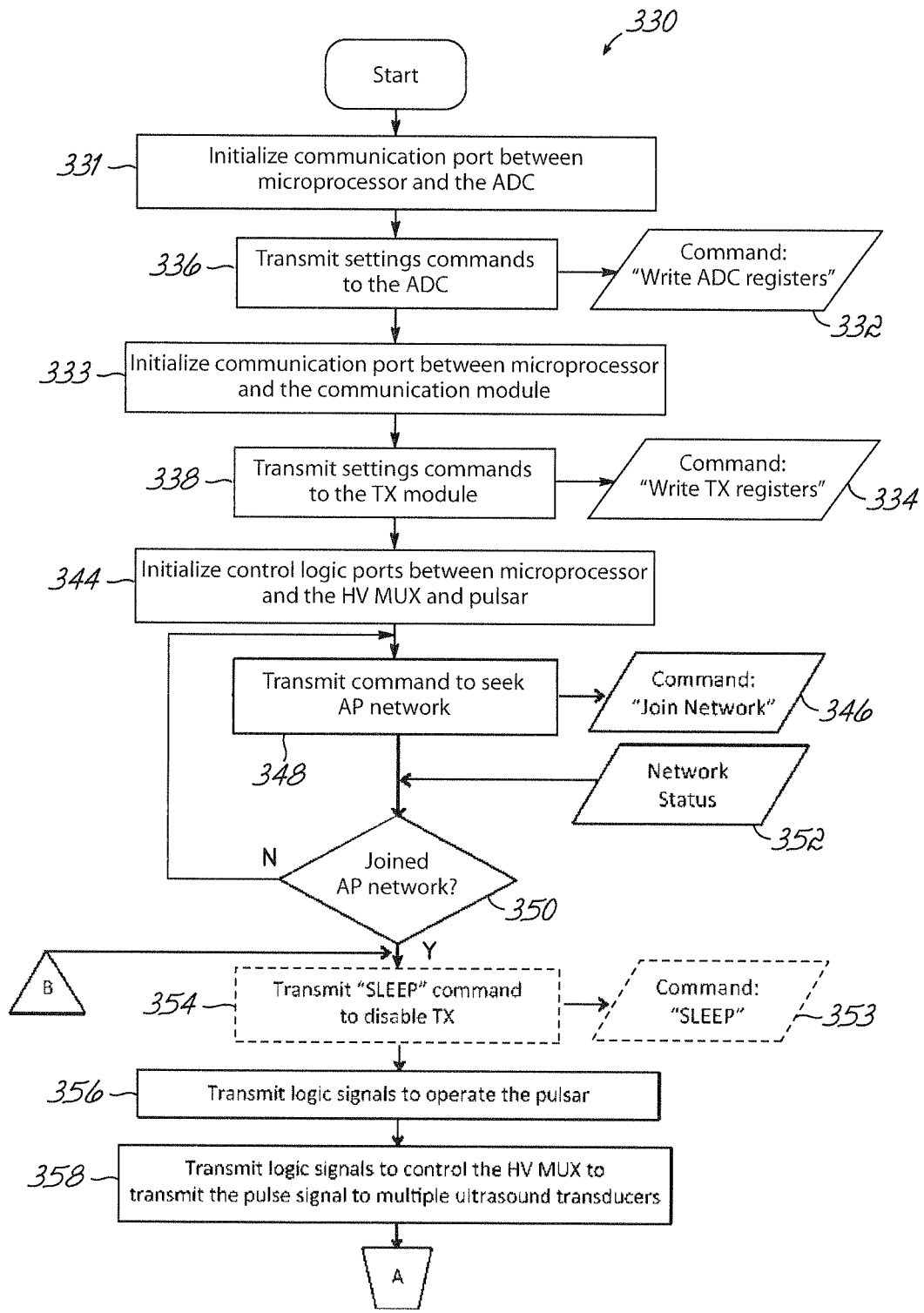
FIGS. 10A-10B are flowcharts illustrating a sequence of instructions for acquiring ultrasound data in the ultrasound module of FIG. 2.
Figure 10B:
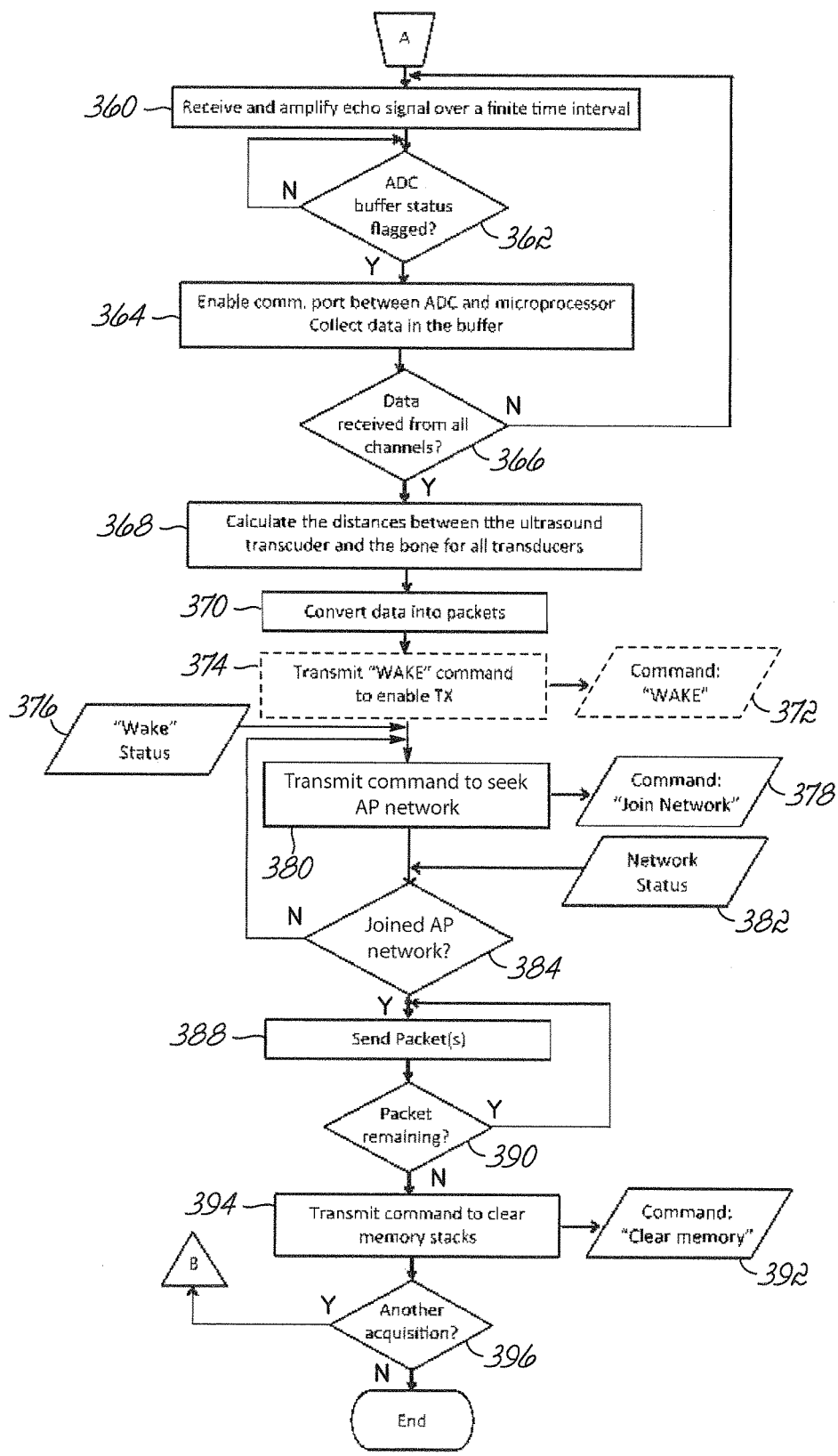

FIGS. 10A and 10B present a flowchart 330 demonstrating the firmware instruction flow of the processor 92 for the ultrasound module 52 in accordance with an embodiment of the invention. The processor 92 may initiate two communication ports: one port with the ADC 90 (Block 331) and the other port with the communication module 94 (Block 333). A command (Block 332 as to the ADC 90 and block 334 as to the communication module 94) is sent to verify that the ports are functioning properly (Block 336 and Block 338, respectively). An instruction set may then be sent to the registers of the ADC 90 and communication module 94 to configure the settings of the ADC 90 and communication module 94, respectively.

A one-way instruction port may then be initiated with the pulse generator (not shown) and the high voltage multiplexer 84 (Block 344). Operation of the pulse generator and the high voltage multiplexer 84 may be controlled by a logic control unit on the processor 92. The processor 92 may then send a command (Block 346) to seek an AP, including an RX operating at the same bandwidth as the ultrasound module 52 (Block 348). If an AP is within range of the RX, the TX will attempt to connect to the network. Once the connection is verified ("Yes" branch of Block 350) by a network status (Block 352), the processor 92 may, optionally, disable the communication module 94 via a command (Block 353) to conserve power during ultrasound data acquisition (Block 354).

The processor 92 transmits a logic signal to operate the pulse generator (not shown) for generating an excitation pulse for the ultrasound transducer 40 (Block 356). The logic control unit of the processor 92 may then transmit the logic signals to the high voltage multiplexer 84 to couple the pulse generator excitation signal to one of the ultrasound transducers 40 on the knee brace 32 (Block 358). After the ultrasound pulse is transmitted, the processor 92 proceeds to block 360 and causes the ultrasound module 52 to enter a receiving mode. While in the receiving mode, the ultrasound module 52 observes or receives the ultrasound echo signal over a receiving period of time. During the receiving period, the VGA 88 amplifies signals generated by the ultrasound transducers 40 and provides the amplified signals to the input of the ADC 90. The ADC 90 receives and converts these amplified signals into digital data for transmission to the processor 92 (Block 360). In an embodiment of the invention, the ADC 90 receives and converts the signals continuously.

When the transmission is complete, a notification signal is sent to the processor 92 to indicate the data is ready at the ADC buffer ("Yes" branch of Block 362); otherwise ("No" branch of Block 362) the transmission, conversion, and amplification continues. The processor 92 collects the amplified data from the ADC 90 (Block 364).

When the data from all data channels has been received ("Yes" branch of decision block 366), the processor 92 uses the received data to calculate the distance between each ultrasound transducer 40 and the bone (Block 368). The processor 92 places the received data into a message array and converts the message array into packets for transmission to the transmitter (Block 370). For transmitting the packets, a command (Block 372) is transmitted to wake and enable the TX (Block 374). Once awakened (Block 376), a command (Block 378) is sent to seek and join the AP network (Block 380). Based on the network status (Block 382), the TX continues seeking the AP network ("No" branch of Block 384) or the process continues ("Yes" branch of Block 384) and the packets are sent (Block 388).

When there are no packets awaiting transmission ("No" branch of Block 390), a command (Block 392) is sent to clear the memory stacks (Block 394). The TX waits for notification of another acquisition ("Yes" branch of block 396), otherwise ("No" branch of block 396), the process ends.

In an embodiment of the invention, the following method may be used in processing the orientation estimation and optimization problem. The fundamental problem with the traditional Kalman estimation family for quaternion is the construction of the error covariance matrix. The components of the quaternion vary with each other as a function to maintain the unit norm constraint. Many implementations and variations optimize the error covariance via projections or various ad hoc techniques such as modifying and restoring the quaternion to maintain the unit norm property.

Consider the IMU is a discrete non-linear non-Gaussian stochastic system that has the following process and measurement models:

$$x_k = f_k(x_{k-1}, w_{k-1}) \quad (40)$$

$$z_k = h_k(x_k, v_k) \quad (41)$$

where $f_k$ is a function of unknown properties that ties the previous state and the current state, and $h_k$ is a function with unknown properties that links the state $x_k$ to $z_k$.

As the statistical properties of these processes are unknown, the Bayesian approach to this problem is to construct a posterior probability density function of the predicting estimate given all previous observations, $$p(x_k|z_{1:k}), z_{1:k} \triangleq \{z_1, z_2 \ldots z_k\} \quad (42)$$

The prior probability density function at time k can be expressed by the Chapman-Kolmogorov equation, $$p(x_k|z_{1:k-1}) = \int p(x_k|x_{k-1}, z_{1:k-1}) p(x_{k-1}|z_{1:k-1}) dx_{k-1} \quad (43)$$

where $p(x_k|x_{k-1}, z_{1:k-1})$ is the predictive conditional density of the process model, and $p(x_{k-1}|z_{1:k-1})$ is the posterior probability density function from previous interval. The posterior probability density function at time k is determined by, $$p(x_k|z_{1:k}) = \frac{p(z_k|x_k)p(x_k|z_{1:k-1})}{p(z_k|z_{k-1})} \quad (44)$$

where $$p(z_k|z_{k-1}) = \int p(z_k|x_k)p(x_k|z_{1:k-1}) dx_k \quad (45)$$

In equation (44), $p(z_k|x_k)$ is the likelihood function described by the measurement model, and $p(z_k|z_{k-1})$ is the normalizing constant. Equation (43) is regarded as the prediction stage of the estimation algorithm, while equation (44) is the update stage. This recursion forms the basis of the recursive estimation algorithm. However, the posterior density is an intractable inference problem that cannot be determined analytically as the size of the dataset is sequentially expanding.

The Sequential Monte Carlo (SMC) method, or particle filter (PF), is a technique to tackle the intractable integral in the posterior density approximation of the sequential Bayesian estimation with the Monte Carlo method. The particle filter can be considered a brute force approach to approximate the posterior density with a large sum of independent and identically distributed random variables or particles from the same probability density space.

Consider a set of N independent random samples that are drawn from a probability density $p(x_k|z_k)$, $$x_k(i) \sim p(x_k|z_{1:k}), \quad i=1:N \quad (46)$$

The Monte Carlo representation of the probability density can then be approximated as, $$p(x_k|z_{1:k}) \approx \frac{1}{N} \sum_{i=1}^{N} \delta_{x_k(i)}(x_k) \quad (47)$$

where $\delta_{x(i)}$ is the Dirac delta function of the points mass. Using this interpretation, the expectation of the any testing function h(x) is given by:

$$\mathbb{E}(h(x_k)) = \int h(x_k) p(x_k|z_{1:k}) dx_k \quad (48)$$

$$\approx \int h(x_k) \frac{1}{N} \sum_{i=1}^{N} \delta_{x_k(i)}(x_k) dx_k$$

$$= \frac{1}{N} \sum_{i=1}^{N} h(x_k(i)),$$

$$i = 1:N$$

In practice, sampling from p(x) directly is usually not possible due to latent hidden variables in the estimation. Alternatively, samples may be drawn from a different probability density $q(x_k|z_{1:k})$, $$x_k(i) \sim q(x_k|z_{1:k}), \quad i=1:N \quad (49)$$

which is generally known as the importance function or the importance density. A correction step is then used to ensure the expectation estimation from the probability density $q(x_k|z_{1:k})$ remains valid. The correction factor, which is generally regarded as the importance weights of the samples ($w_k(i)$), is proportional to the ratio between the target probability density and the proposed probability density, $$w_k(i) \propto \frac{p(x_k | z_{1:k})}{q(x_k | z_{1:k})} \quad (50)$$
$$i = 1 : N$$

The importance weights are normalized:

$$\sum_{i=1}^{N} w_k(i) = 1 \quad (51)$$

Based on the sample drawn from equation (49), the posterior probability density becomes:

$$p(x_k | z_{1:k}) = \frac{p(z_k | x_k, z_{k-1}) p(x_k | z_{k-1})}{p(z_k | z_{k-1})} \quad (52)$$

$$= \frac{p(z_k | x_k) p(x_k | x_{k-1})}{p(z_k | z_{k-1})} p(x_k | z_{1:k-1}) \quad (53)$$

$$\propto p(z_k | x_k) p(x_k | x_{k-1}) p(x_k | z_{1:k-1}) \quad (54)$$

And the importance weight from equation (50) becomes:

$$w_k(i) \propto \frac{p(z_k | x_k(i)) p(x_k(i) | x_{k-1}(i)) p(x_{1:k-1}(i) | z_{1:k-1})}{q(x_k(i) | x_{1:k-1}(i)) q(x_{i:k-1}(i) | z_{1:k-1})}, \quad (55)$$
$$i = 1 : N$$

$$= w_{k-1}(i) \frac{p(z_k | x_k(i)) p(x_k(i) | x_{k-1}(i))}{q(x_k(i) | x_{1:k-1}(i))} \quad (56)$$

$$\propto w_{k-1}(i) \frac{p(z_k | x_k(i)) p(x_k(i) | x_{k-1}(i))}{q(x_k(i) | x_{k-1}(i))} \quad (57)$$

The posterior probability density can then be approximated empirically by:

$$p(x_k|z_{1:k}) \approx \sum_{i=1}^{N} w_k(i) \delta_{x_k(i)}(x_k) \quad (58)$$

The expectation of the estimation from equation (48) can be expressed as:

$$\mathbb{E}(h(x_k)) = \int h(x_k) p(x_k | z_{1:k}) dx_k \quad (59)$$
$$\approx \int h(x_k) \sum_{i=1}^{N} w_k(i) \delta_{x_k(i)}(x_k)$$
$$= \sum_{i=1}^{N} w_k(i) h(x_k(i)),$$
$$i = 1 : N$$

The technique demonstrated by equations (52-59) is regarded as the sequential importance sampling (SIS) procedure. However, the issue with SIS is that the importance weights will be concentrated on a few samples while the rest of them become negligible after a few recursions. This is known as the degeneracy problem with particle filter. A frequent approach to counter this problem is resampling the samples such that they are all equally weighted based on the posterior density. However, since resampling the samples introduces Monte Carlo error, resampling should not be performed in every recursion. It should only be executed when the distribution of the importance weight of the sample has been degraded. The state of the samples is determined by the effective sample size, which is defined by, $$N_{eff} = \frac{N}{1 + \text{var}(w_k^*(i))}, \quad i = 1 : N \quad (60)$$

where $w_k^*(i)$ is the true weight of the sample, $$w_k^*(i) = \frac{p(x_k | z_{1:k})}{q(x_k(i) | x_{k-1}(i))}, \quad i = 1 : N \quad (61)$$

However, as the true weight of the sample cannot be determined directly, the following method is used to approximate the effective sample size empirically with the normalized weights.

$$N_{eff} = \frac{1}{\sum_{i}^{N} w_i^2}, \quad i = 1 : N \quad (62)$$

Resampling is performed when $N_{eff}$ drops below a predetermined threshold $N_{th}$, which is done by relocating the samples with small weight to the samples with higher weights, hence, redistributing the weights of the particles.

The major challenge to apply PF to IMU orientation estimation is to generate a statistical geometry for the quaternion. The current PF implementation utilizes hyper dimensional directional statistical method to generate and examine the quaternions. Directional statistics is a special subset of statistics that primarily deals with directions, axes and rotations. The topological space of a collection of p-dimensional orthonormal vectors in N-dimensional space is considered to be the Stiefel Manifold ($V_p$), which is defined as, $$V_p(\mathbb{R}^N) = \{A \in \mathbb{R}^{N \times p} : A^*A = 1\} \quad (63)$$

where can be any inner product space.

For quaternion, where p=4 and N=3, satisfies such condition and forms a unique case on the manifold, $$V_p(\mathbb{R}^N) = \{q \in \mathbb{R}^{N \times p} : q^* \otimes q = I_p\} \quad (64)$$

where $I_p$=[1 0 0 0].

Statistical distributions residing on the Stiefel manifold generally includes any arbitrary dimensional objects in any dimensional space. Any distribution satisfying the condition of p<N can be used as a quaternionic distribution. Two of these distributions include the von Mises-Fisher distribution and the Bingham distribution.

The von Mises Fisher (vMF) distribution is a generalized spherical distribution of a p-dimensional object in p−1 dimensional space. The probability density function of a generalized von Mises Fisher distribution of p-dimensional object is given as, $$f_{vMF}(X; F) = \frac{1}{a(F)} e^{tr(FX^T)} \quad (65)$$

where X is a p×N matrix of orthogonal unit vectors, F is a p×N parameters matrix, and 1/a(F) is the normalizing constant, which can be expressed by a confluent hypergeometric limit function, $$a(F) = {}_0F_1\left(\frac{N}{2}, \frac{FF^T}{4}\right) \quad (66)$$

$$= I_\nu(F)\frac{\Gamma\left(\frac{-N}{2}+1\right)}{\left(\frac{F}{2}\right)^{-\frac{N}{2}}} \quad (67)$$

where $I_\nu$ is the Bessel function of the first kind, $\Gamma$ is the gamma function.

The distribution applied to quaternion with p=4 becomes, $$f_{vMF}(x; \mu, \kappa) = C_4(\kappa)e^{(\kappa\mu^T x)} \quad (68)$$

$$C_4 = \frac{\kappa}{2\pi^2 I_\nu(\kappa)} \quad (69)$$

where x is a random quaternion, μ is the mean vector, and κ is the dispersion factor.

Direct statistical inference with the von Mises-Fisher distribution can be approximated with Wood's algorithm, which is based on Ulrich's simulation proposal for m-sphere. Instead of trying to generate samples from the distribution, the algorithm simulates random samples that have the statistical properties of the real distribution. Ulrichs's theorem postulated that a unit p-vector X has a von Mises-Fisher distribution with mean direction at $X_0$=[1 0 0 0] if and only if $$X^T = (V\sqrt{1-W^2}, W) \quad (70)$$

where V is a uniformly distributed unit (p−1) vector and W is the scalar random variable ranging from −1 to 1. The von Mises-Fisher simulation comes down to determining an efficient method to simulate W, which is calculated with Ulrich's proposal by using an envelope proportional to the density along with beta random variables.

$$e(x, b) = d_{m,b}^{-1}(1-x^2)^{\frac{(m-3)}{2}}(1+b-(1-b)x)^{-(m-1)} \quad (71)$$

$$d_{m,b}^{-1} = \left(\Gamma\left(\frac{(m-1)}{2}\right)\right)^2 b^{-\frac{m-1}{2}} / 2\Gamma(m-1) \quad (72)$$

$$b = \frac{-2F + \sqrt{4F^2 + (m-1)^2}}{m-1} \quad (73)$$

$$Z \sim \beta[-(m-1)/2, (m-1)/2] \quad (74)$$

$$W = 1 - (1+b)Z/1 - (1-b)Z \quad (75)$$

Figure 11:
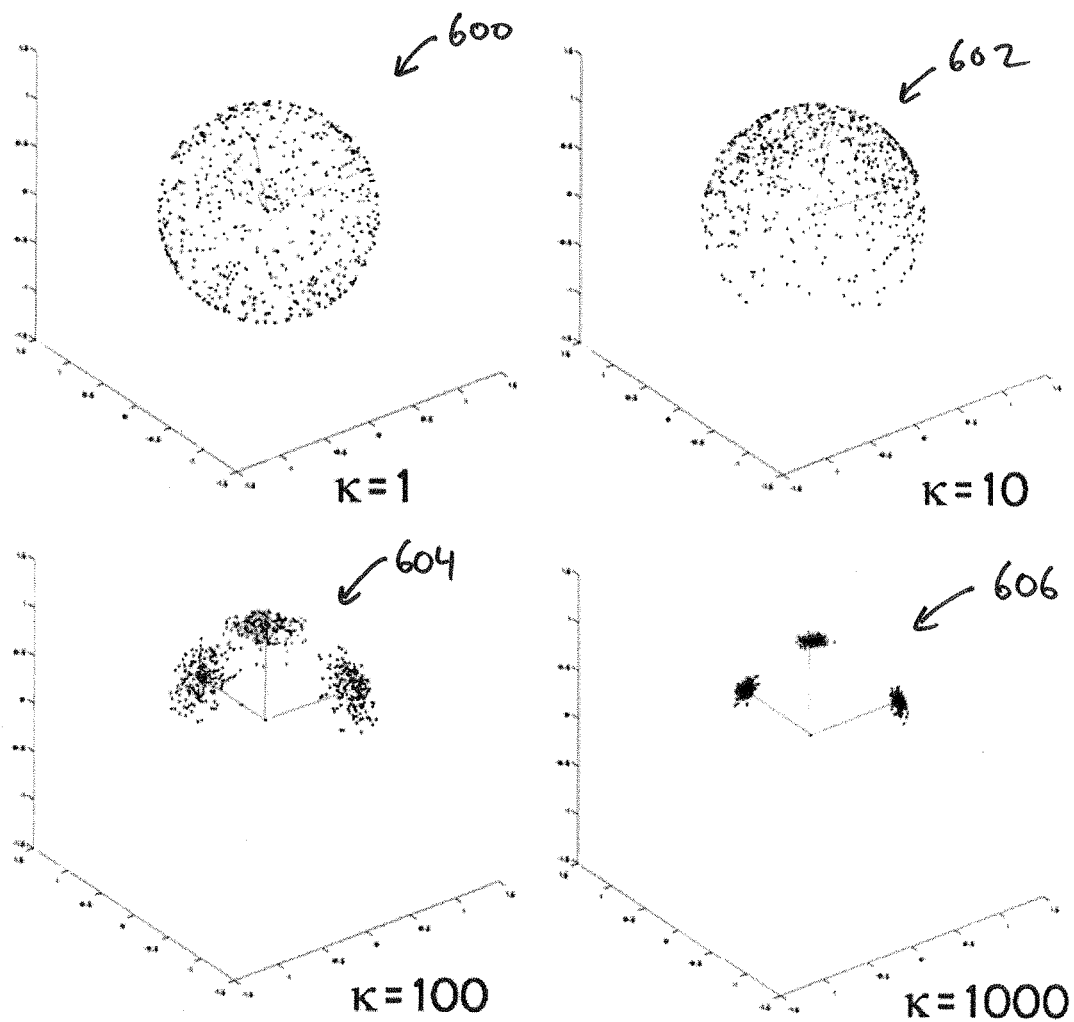
FIG. 11 is a diagrammatic view illustrating randomly sampled quaternions.

FIG. 11 illustrates randomly sampled quaternions 600, 602, 604, 606 with von Mises-Fisher distributions having different dispersion factors, and shows the output from the von Mises-Fisher simulation with different level of dispersion parameters at the mean direction of [1 0 0 0]. As the dispersion factor increases, the concentration of the sample increases. Since the distributions below is projected to the 3-sphere with an identity matrix, the figures do not represent the full distribution but an instance of it. The von Mises-Fisher distribution is a subclass of a generic higher dimensional distribution known as Bingham distribution. The von Mises-Fisher assumes the samples are uniformly distributed around the mean direction of the rotation manifold. Bingham distribution is a statistical distribution for hyper-dimensional object that does not assume rotational symmetry and uniformity. The distribution is extremely flexible and can represent even elliptic or girdle distribution geometry. The probability density for the Bingham distribution is defined as $$f_B(\pm q; K) = {}_1F_1\left(\frac{1}{2}, \frac{p}{2}, K\right)^{-1} e^{q^T U K U^T q} \quad (76)$$

$${}_1F_1\left(\frac{1}{2}, \frac{p}{2}, K\right) = \sum_{n=0}^{\infty} \frac{1/2^{(n)} K^n}{p/2^{(n)} n!} \quad (77)$$

where q is the quaternion describing the orientation, $${}_1F_1\left(\frac{1}{2}, \frac{p}{2}, K\right)^{-1}$$

is Kummer's function of the first kind as normalizing constant, U is an orthogonal matrix describing the orientation of the distribution, and K is diagonal matrix that describes the dispersion axes of the distribution defined as, $$K = \begin{bmatrix} \kappa_s & 0 & 0 & 0 \\ 0 & \kappa_1 & 0 & 0 \\ 0 & 0 & \kappa_2 & 0 \\ 0 & 0 & 0 & \kappa_3 \end{bmatrix} \quad (78)$$

Similar to the von Mises-Fisher distributions, Bingham distribution cannot be sampled directly, and indirect simulation method is used. A rejection sampling algorithm was designed to create a set of random simulation samples from the Bingham density. Rejection criterion is based on the maximum and minimum acceptance densities. There are two methods to initialize the samples for the rejection algorithm, which are random hypersphere simulation, and the von Mises-Fisher simulation method. According to equation (76), Bingham density models an antipodal symmetric distribution. Hence, rejection sampling using random hyperspheres will result with bimodally distributed samples as the equation accepts the quaternions and its complex conjugates that fall within the acceptance range. This can adversely affect the expectation's direction of the random samples as it becomes unpredictable when projecting back to 3D. This is highly undesirable for tracking applications.

Figure 12:
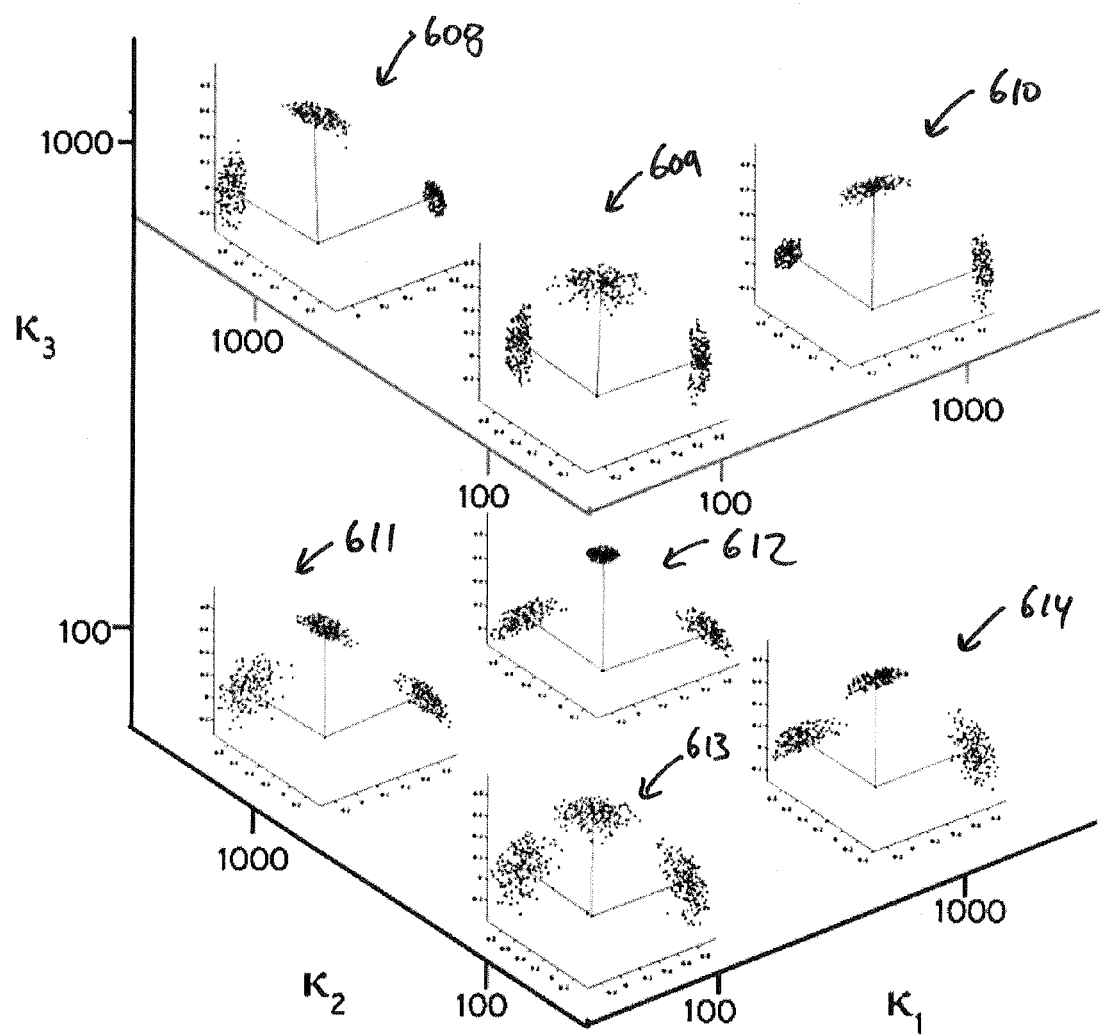
FIG. 12 is a diagrammatic view illustrating randomly sampled quaternions with non-uniform distributions with different density proportion in K.

A secondary proposal is to use the samples created from the von Mises-Fisher simulation with small dispersion factor to initialize the sampling with a large particles spread. This will remove the possibility of sampling the complex conjugate of the quaternion. In addition, initializing with von Mises-Fisher density reduces the time to generate samples significantly as it restricts the seeking space of the samples. However, since the samples generated from this method eliminate the antipodal properties of the distribution, it cannot be considered as the Bingham distribution. This is referred as the non-uniform (NU) distribution and density in the following sections. FIG. 12 illustrates randomly sampled quaternions 608-614 with non-uniform distributions with different density proportion in K. The samples are projected to 3-sphere with identity matrix, and show the output from the simulation with different dispersion matrix (κ) at the mean direction of [1 0 0 0].

Figure 13:
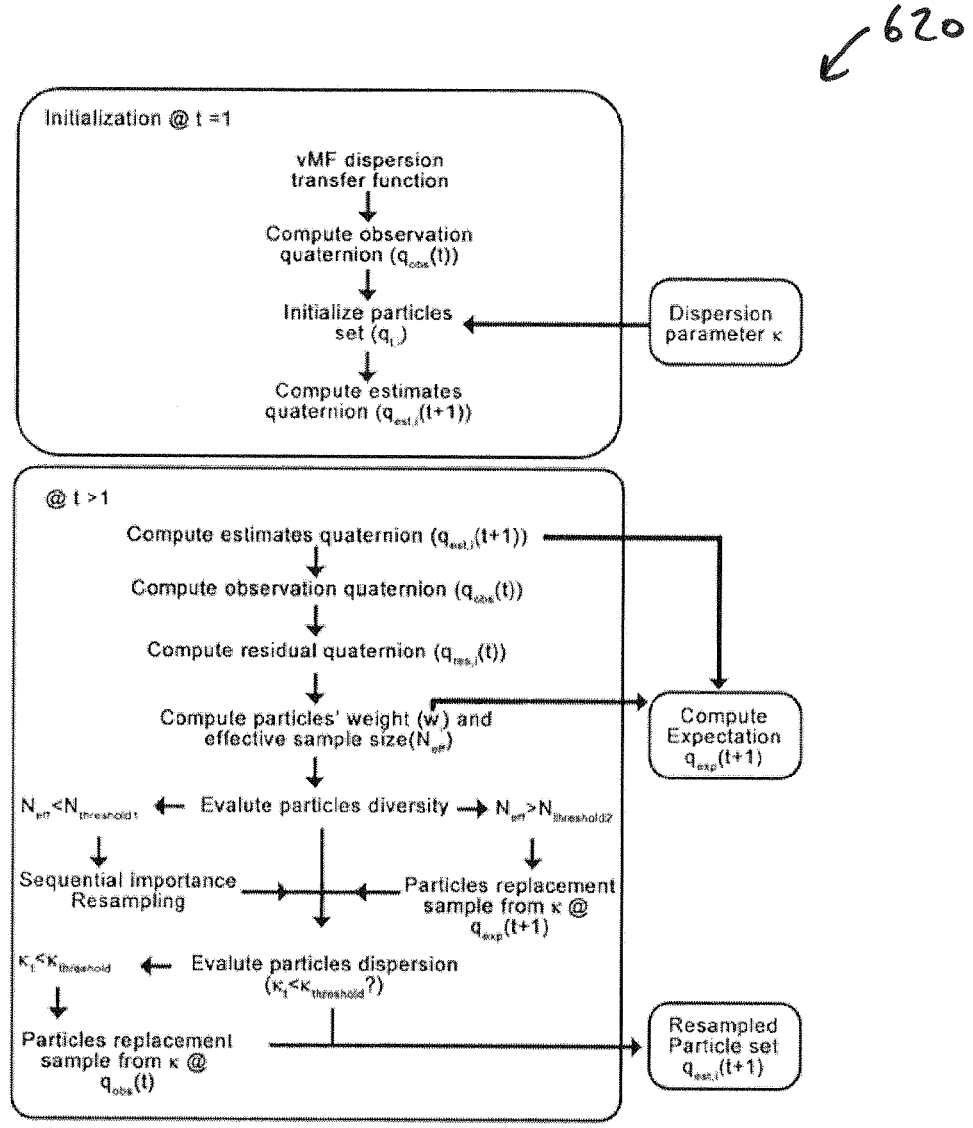
FIG. 13 is a block diagram view of a PF algorithm with von Mises-Fisher density.

One of the challenges in formulating PF is to tie the particles generation, particles evaluation and particles maintenance together such that the particles can be weighed correctly, and to produce the optimal importance density that reflects the state of the estimation. The following method establishes a correlation between the uncertainties of the random particles and the dispersion factors such that particles can be generated and evaluated based on the posterior density. The implementation of PF for tracking application based on the von Mises-Fisher density is shown in FIG. 13, which illustrates a functional block diagram 620 of the PF algorithm with von Mises-Fisher density. A set of N particles samples is simulated at a different dispersion factor at the mean direction [1 0 0 0]. The rotational uncertainty of these particles is determined by the root sum squared of the minimum angle between two hyper-complex vectors:

$$\delta_i = \sqrt{\Sigma_i^N (2 * acos(|q_{x,i}^\kappa \cdot q_0|))^2} \tag{79}$$

Figure 14:
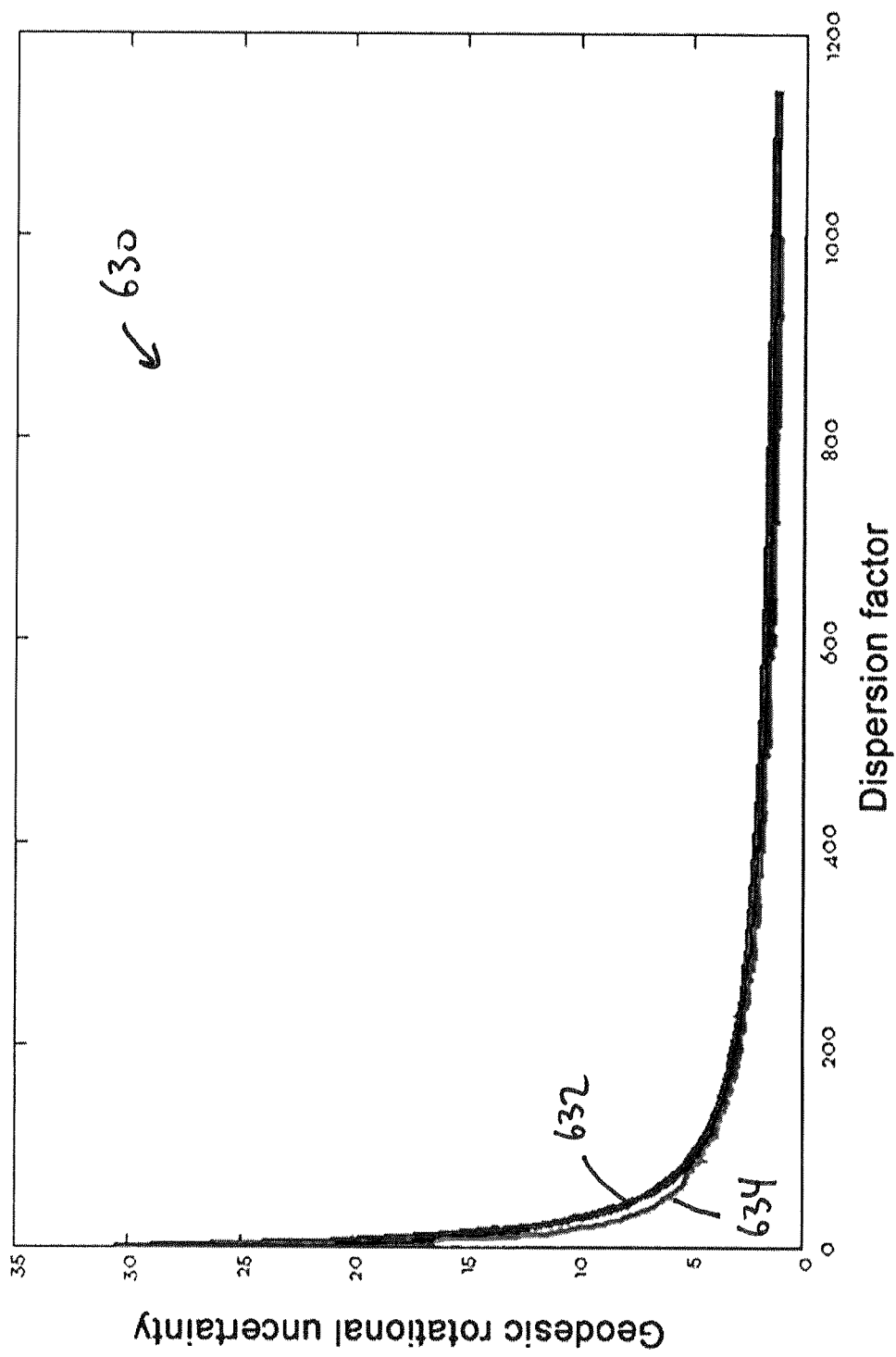
FIG. 14 is a graph which includes plots of the transfer function and the simulation.

$q_0 = [1\ 0\ 0\ 0]$, $q_{x,i}^\kappa \sim vMF(\kappa)$, $i=1 \to N, \kappa=\kappa_{min} \to \kappa_{max}$ The relationship between $\delta_i$ and κ is realized with least squared approximation of the two datasets with the function in equation (80), and FIG. 14, which illustrates a graph 630 which includes plots of the transfer function 632 and the simulation 634:

$$\kappa(\delta, x) = ae^{-b(\delta)} + ce^{-d(\delta)}, x = [a\ b\ c\ d] \tag{80}$$

During the initialization procedure, the observation quaternion is initialized with the Gauss Newton method. A set of N particles is computed based on the Wood's simulation with an arbitrary dispersion factor. The initial particles estimates ($q_{est,i}(t)$) become:

$$q_{est,i}(t) \sim vMF(\kappa) \otimes q_{obs}(t), i=1 \ldots N \tag{81}$$

All the particles are assigned with equal weights during the initialization period. The weights and dispersion factor are updated accordingly in the subsequent cycle by the posterior filtering density. The algorithm then computes the particles estimates for the next cycle at time=t+1, $$q_{est,i}(t+1) = q_{est,i}^\kappa(t) + 0.5(q_{est,i}^\kappa(t) \otimes [0\omega_x \omega_y \omega_z])\Delta t, \\ i=1 \ldots N \tag{82}$$

where ω is the angular rate measured at time t, and Δt is the sampling period.

After the initialization, the recursive portion of the algorithm begins by first determining the observation quaternion $q_{obs}(t)$ at the current time, and the estimates of the next cycle are computed with equation (82). Particles evaluation depends on the hypothesis of the optimal importance density. Since there are two parameters in the von Mises-Fisher density, the ideal choice for the orientation tracking is the residual density defined in equation (83). This is because the optimal mean direction of the residual particles is always [1 0 0 0] instead of an arbitrary quaternion.

$$q_{res,i}(t) = q_{est,i}(t) \otimes conj(q_{obs}(t)), i=1 \ldots N \tag{83}$$

The second parameter, the dispersion factor, is approximated sequentially with following method. The weight of the particles must first be determined. The rotational disparity between the optimal residual quaternion and the residual particles is given by:

$$\theta_{res,i} = 2\cos(q_{res,i}(t) \cdot q_0), i=1 \ldots N \tag{84}$$

The rotational difference is then used to determine the importance weights of the particles estimates, where less rotational discrepancy receives higher weight and vice versa.

$$w_i = \frac{1/\delta_{res,i}}{\sum_i^N (1/\delta_{res,i})}, i=1 \ldots N \tag{85}$$

The posterior dispersion parameter is updated with, $$\kappa\left(\sqrt{\sum_i^N \delta_{res,i}^2}, x\right) = ae^{-b\left(\sqrt{\sum_i^N \delta_{res,i}^2}\right)} + ce^{-d\left(\sqrt{\sum_i^N \delta_{res,i}^2}\right)}, \tag{86}$$

$x = [abcd], i = 1 \ldots N$

The expectation of the filtered quaternion is computed with the particles estimates and their weights. This is accomplished by computing the weighted spherical averages of the particles. There are various techniques to compute spherical averaging. The presented algorithm uses spherical linear interpolation (SLERP) to interpolate the rotation between two quaternions. SLERP computes the intermediate rotation of two orientation inputs and the weight parameter ranging from 0 to 1. The weight parameter determines the influence of each of the rotational inputs to the output. A weight of 0.5 is equal to calculating the mean rotation of the two inputs. Since all the particles are weighted differently, the weights are first normalized between two examining particles. The weight of the output is computed by the ratio of the normalized weight. In each iteration, the algorithm interpolates a new generation of particles and weights that is half the size of the input until there is only one particle left. This algorithm is limited to sample size of $2^n$. Zero padding is necessary for this algorithm if another sample size is used.

Particle maintenance is to ensure the effectiveness of the particle estimates for statistical inference and to avoid degeneracy. The first step is to determine the effective sample size $N_{eff}$ described in equation (62). In the current implementation of the PF, the particle maintenance is accomplished by two scenarios.

In the first scenario, two thresholds are set by the user. The first threshold ($N_{th1}$) determines whether the particle samples require importance resampling. If the $N_{eff}$ is smaller than $N_{th1}$, importance resampling is performed. The second threshold ($N_{th2}$) is used to enrich the particles' diversity. This threshold is added in addition to the original because instead of the importance weights' degeneracy; the importance density becomes highly concentrated from the resampling where a large population of the particles estimates becomes identical. If $N_{eff}$ is larger than $N_{th2}$, the particles are replaced by the new particles that are sampled from the posterior density in equation (86) and the expectation quaternion.

$$q_{rs,i}(t) \sim vMF\left(\kappa\left(\sqrt{\sum_i^N \delta_{res,i}^2}, x\right)\right) \otimes (q_{exp}(t+1)) \tag{87}$$

$i = 1 \ldots N$

The weight is also updated based on the re-sampled particles. This step increases the diversity of the particles while maintaining the statistical properties of the particles.

Figure 15:
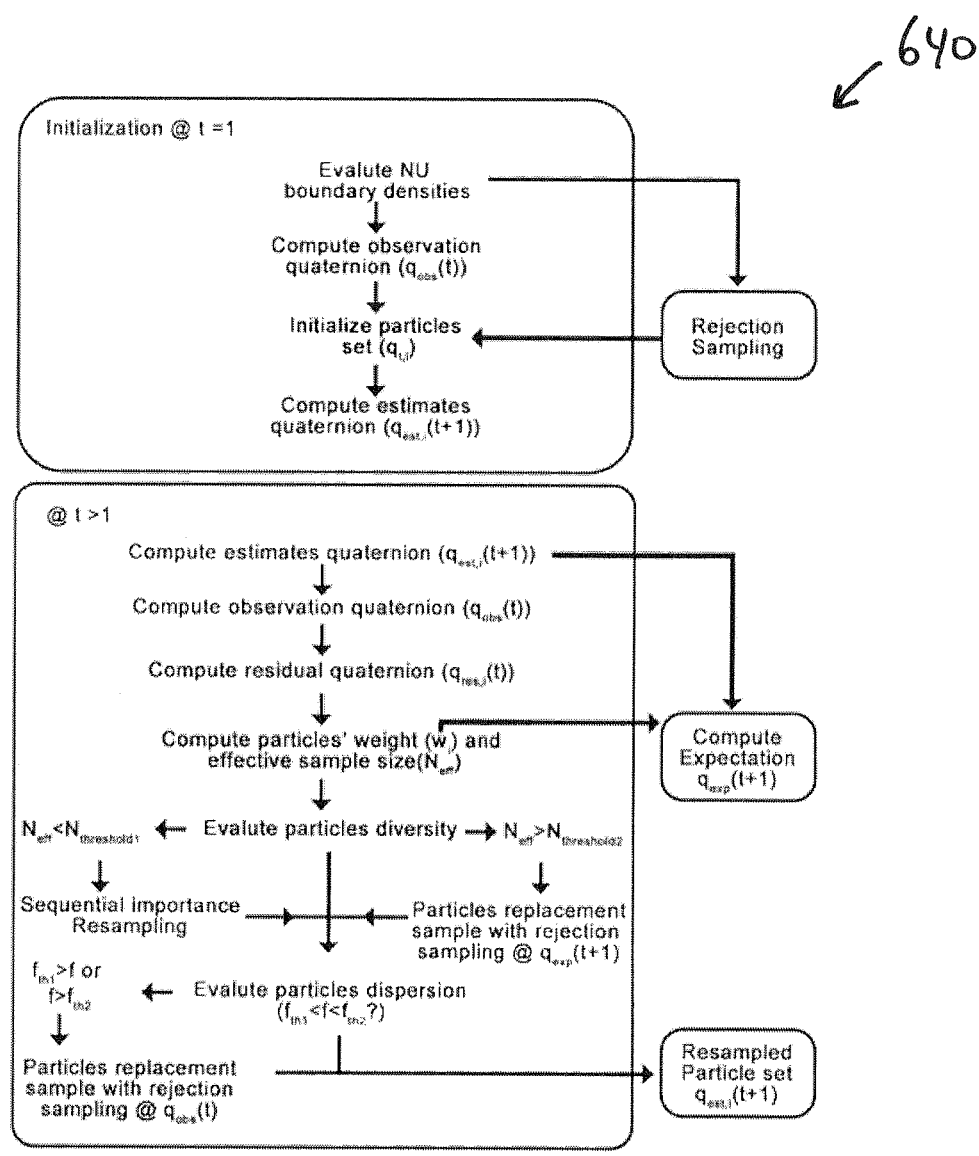
FIG. 15 is function block diagram view which illustrates a functional block diagram of a PF algorithm with non-uniform density.

The second scenario takes into account of the hardware system of the inertial monitoring unit 48. Cases have been identified that can cause temporary interruption or interference to inertial monitoring unit 48. For instance, external magnetic fields may be generated or distorted by laptop batteries or speakers. This may disturb the signals produced by the magnetometers 60. Motion that causes temporary sensing signal saturation in the inertial monitoring sensors 36 can also lead to incorrect position estimations. In addition, antennas in the communication modules 70, 80, 94 may obscured by the user. Signal obstruction by the user may cause a transmission lag, which is highly undesirable for rate-dependent estimation. These events may lead to a significant error in the posterior density approximation as the prediction and observation are misrepresented. The dispersion factor, which is based on the state of the residual particles, will decrease to increase the spread of the particles. It is possible for the filter to destabilize if the dispersion factor is low enough that the particles become completely random hyperspheres. Since the effectiveness of the particles is monitored by normalized importance weight, the effectiveness cannot be directly observed if the residual particles are drifting away from the optimal direction. The most direct method is to monitor the posterior density, which infers the uncertainty state of the residual particles. Therefore, a dispersion threshold ($\kappa_{TH}$) is set up to prevent excessive dispersion. If the dispersion calculated in (47) drops below $\kappa_{TH}$, the particles are reset by sampling a new set particles at ($q_{obs}(t)$) with the initial dispersion factor used at time=1. Since the sampling methods between von Mises-Fisher and non-uniform densities are substantially different from one another, the set up for the PF, and the particles maintenance procedures need to be re-designed. In non-uniform sampling methods, the shape of the density is governed by the dispersion shape matrix K, defined in equation (78), and the amount of dispersion is controlled by the maximum and minimum acceptance boundaries ($f_{max}$ and $f_{min}$). The overall function block for PF with NU density is shown in FIG. 15, which illustrates a functional block diagram 640 of the PF algorithm with non-uniform density. The particles may be initialized by sampling with a rejection sampling method. The initial particles estimates ($q_{est,i}(t)$) become, $$q_{est,i}(t) \sim NU([f_{max}, f_{min}], K) \otimes q_{obs}(t), i=1 \ldots N \quad (88)$$

These particles are weighted equally. The particles estimates are computed with equation (82). The uncertainty states of the particles are determined with equation (82-84). The effective sample size is calculated with equation (62). Sequential importance resampling is performed in the same manner as the PF with von Mises-Fisher density method. However, to enrich the particle diversity after the effective particle size $N_{eff}$ exceeds $N_{th2}$, replacement particles must be sampled from the density that describes the current particle state. This is achieved by first determining the density of the residual quaternions, $$f_{res,i} = {}_1F_1\left(\frac{1}{2}, \frac{p}{2}, q_{res,i}(t)\right)^{-1} e^{q_{res,i}(t)^T UK U q_{res,i}(t)}, i = 1:N \quad (89)$$

$$\propto e^{q_{res,i}(t)^T UK U q_{res,i}(t)}$$

The maximum and minimum residual densities are used as the new acceptances boundaries, where the replacement particles are drawn from:

$$q_{res,i}(t) \sim Nu([f_{max}, f_{min}], K) \otimes (q_{exp}(t+1))\ i=1 \ldots N \quad (90)$$

The state of the residual particles direction is monitored by two pre-determined densities boundaries ($f_1$ & $f_2, f_1 < f_2$) to prevent particles divergence from fault inputs. If $[f_{max}, f_{min}]$ is not within the density bounds defined by $f_1$ & $f_2$, the particles are reset by sampling a new set particles at ($q_{obs}(t)$) with the initial boundaries at time=1.

Gyroscopes drifting bias is one of the major causes in attitude estimation error. The PF discussed in previous sections can only observe and correct drifting error via monitoring the direction of the residual density and correct the particles only if they jeopardize the stability of the filter. Bias correction can be used in conjunction to produce the particle estimates. This can enhance the stability and accuracy of the filter as it reduces the occurrence of particles replacement caused by large prediction and update error; where the particles are reset.

Figure 16:
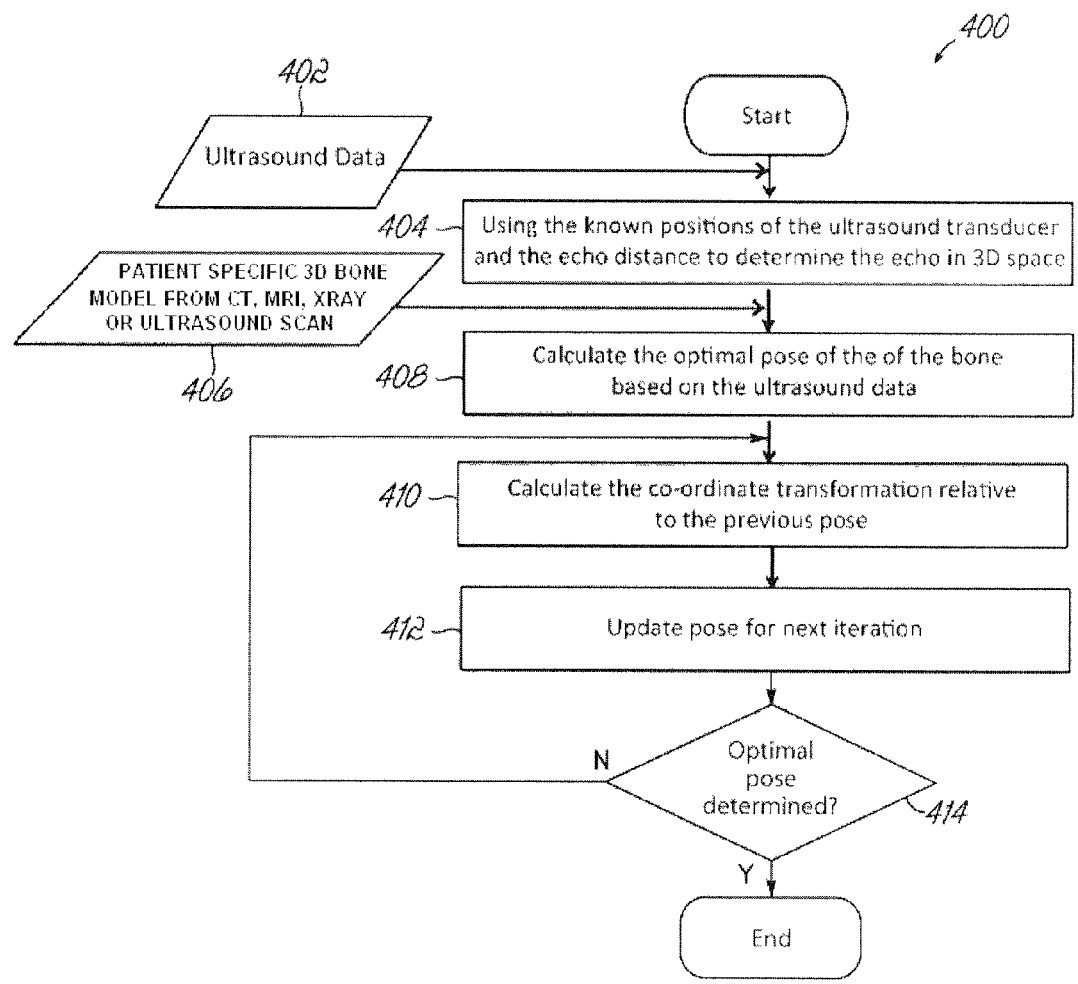
FIG. 16 is a flowchart illustrating a sequence of instructions for calculating a patient's 3D bone pose from the data received from the ultrasound module of FIG. 2.

With reference to FIG. 16, a flowchart 400 illustrating an instruction flow for a software bone pose tracking algorithm is described in accordance with an embodiment of the invention. With the ultrasound data received (Block 402) and in view of the known positions of the ultrasound transducers 40 with respect to the echo distance, the echo may be determined in three-dimensional space (Block 404). A patient-based model may be input (Block 406) and used in calculating the optimal pose of the bone based on the ultrasound data (Block 408). The patient-based model may be derived from the prior segmentation of data from another imaging modality, including, for example, computed tomography, magnetic resonance imaging, radiograph, or ultrasound bone scans. The segmented data of the patient-based model may be registered into a space with the three-dimensional points from the ultrasound transducers 40 as the boundary conditions for the bone pose optimization. The optimal pose may be used to calculate a transformation for relating the differences in the coordinate systems between the brace and the bone during activities (Block 410). Therefore, each iteration of the determined pose is registered and saved for calculating next iteration in the algorithm (Block 412). If all iterations are complete ("Yes" branch of decision block 414), then the process ends; otherwise ("No" branch of decision block 414) the process returns to calculate the transformation.

Figure 17:
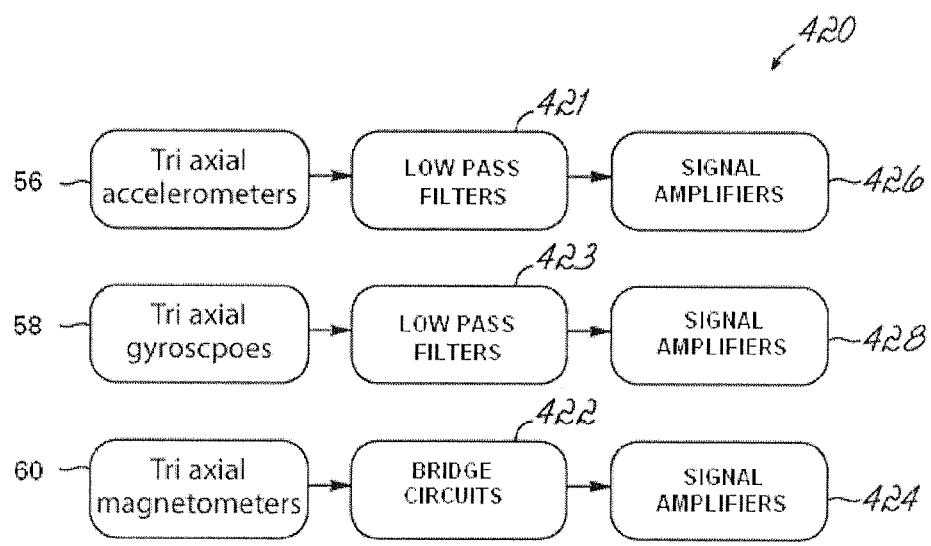
FIG. 17 is a schematic view of a plurality of exemplary signal conditioning circuits for use with the inertial monitoring units of the motion tracking system of FIG. 2.

FIG. 17 is a schematic illustrating a signal processing module 420 suitable for use with the inertial monitoring unit 48 in accordance with an embodiment of the invention. The output signals of the accelerometers 56 and the gyroscopes 58 are separately filtered by low pass filters 421, 423. The filtered signals are then separately amplified by signal amplifiers 426, 428. Each sensing axis of the magnetometers 60 is processed by a bridge circuit 422, which generates a differential output on each axis. The differential outputs are processed by differential amplifiers 424 to cancel noise that is common to both inputs of the amplifier 424. The differential signal is then amplified to produce a highly accurate signal for the ADC 64 of inertial monitoring unit 48. Because the differential outputs may be either positive or negative, and the ADC 62 may be configured for receiving only positive input signals, and a DC bias may be introduced to the positive input of the differential amplifier to ensure that the signal remains positive.

Figure 18:
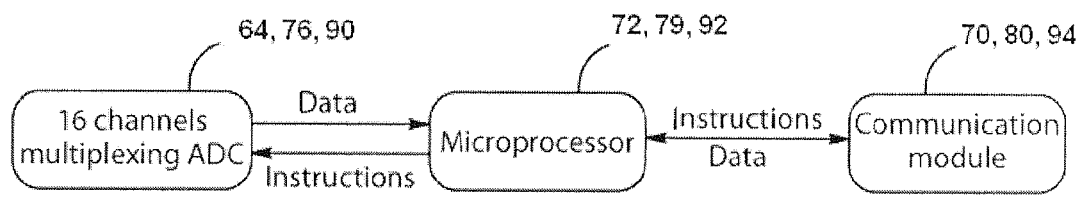
FIG. 18 is a schematic view of an multi-channel analog-to-digital converter, processor, and communication module for use with the modules of FIG. 2.

Turning now to FIG. 18, the flow of data between the ADCs 64, 78, 90 and the communication modules 70, 80, 94 is shown in accordance with an embodiment of the invention in which the processors 72, 79, 92 control the transfer of data. In an alternative embodiment, the ADCs 64, 78, 90 may be coupled directly to their respective communication modules 70, 80, 94.

Figure 19:
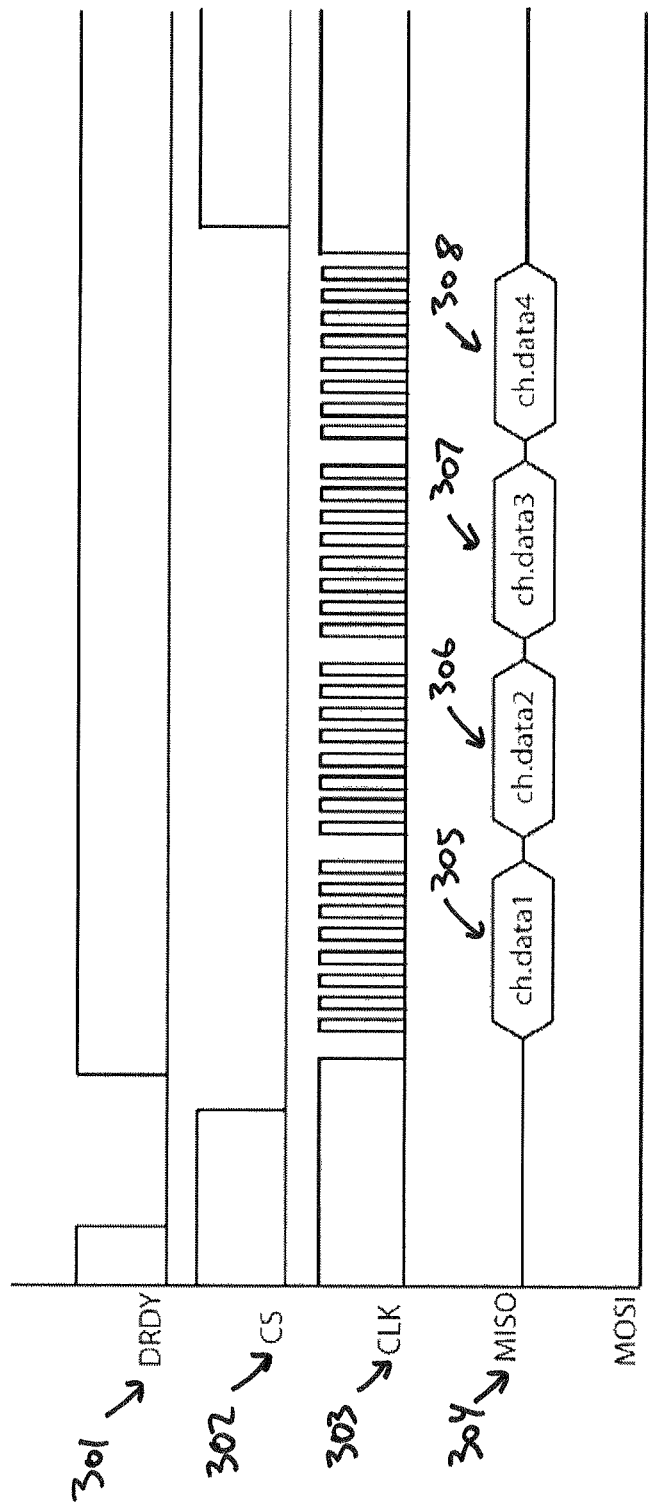
FIG. 19 is a diagrammatic view of an exemplary digital signal protocol for a communication interface.

FIG. 19 illustrates an exemplary sequence of communications signals between the processor 72, 79, 92 and the ADCs 64, 78, 90 during data transfer. The data ready (DRDY) signal 301 is at a logic level zero while the ADC 64, 78, 90 completes the conversion of the signal in one of its 16-channels. When the conversion is complete (i.e., the data is ready in the buffer) the ADC 64, 78, 90 may set a conversion complete flag. In response to the conversion complete flag being set, the ADC 64, 78, 90 may output the DRDY signal 301 at a logic high level, indicating that the ADC 64, 78, 90 is ready to transmit data. When the processor 72, 79, 92 is ready to receive data from one of the ADCs 64, 78, 90, the processor 72, 79, 92 outputs a chip select (CS) signal 302 to the selected ADC 64, 78, 90 to a logic low value, thereby activating the selected ADC 64, 78, 90. In response to the conversion complete flag being set and the CS signal 302 being at a logic low level, the ADC 64, 78, 90 may transmit the data in the buffer to the processor 72, 79, 92. The data may be transmitted by a data signal 304 on a Master Input, Slave Output (MISO) serial data line connecting an output port of the ADC 64, 78, 90 to an input port of the processor 72, 79, 92. A clock signal 303 is be transmitted on the clock (CLK) line from the ADC 64, 78, 90 to the processor 72, 79, 92 along with the data to latch the data signal 304 into the processor 72, 79, 92 in a controlled manner. The data signal 304 from the ADC 64, 78, 90 may contain digitized samples from multiple inertial monitoring sensors 36, vibration sensors 38, and/or ultrasound transducers 40. In the illustrated embodiment, the data includes data from a first channel 305 (Ch.data1), a second channel 306 (Ch.data2), a third channel 307 (Ch.data3), and a fourth channel 308 (Ch.data4). Each channel may represent, for example, a single digitized 24 bit resolution signal sample from one of the aforementioned sensors 38, 36 and/or transducers 40. In another embodiment, the data output from the ADC module 64, 78, 90 may be organized with <Ch.data1> 305 including one or more bytes (8 bits) of data containing the channel ID and the update status of the corresponding channel, and with <Ch.data2> 306, <Ch.data3> 307, and <Ch.data4> 308 including data words including one or more bytes of data. In a preferred embodiment, 306, 307, and 308 include 3 bytes (24 bits) of data. There may also be a message terminating word comprised of one or more bytes (not shown) following the last data word as is known in the art.

The following non-limiting examples illustrate some results of the use of the various embodiment of the present invention for particular applications.

EXAMPLE 1

Figure 20:
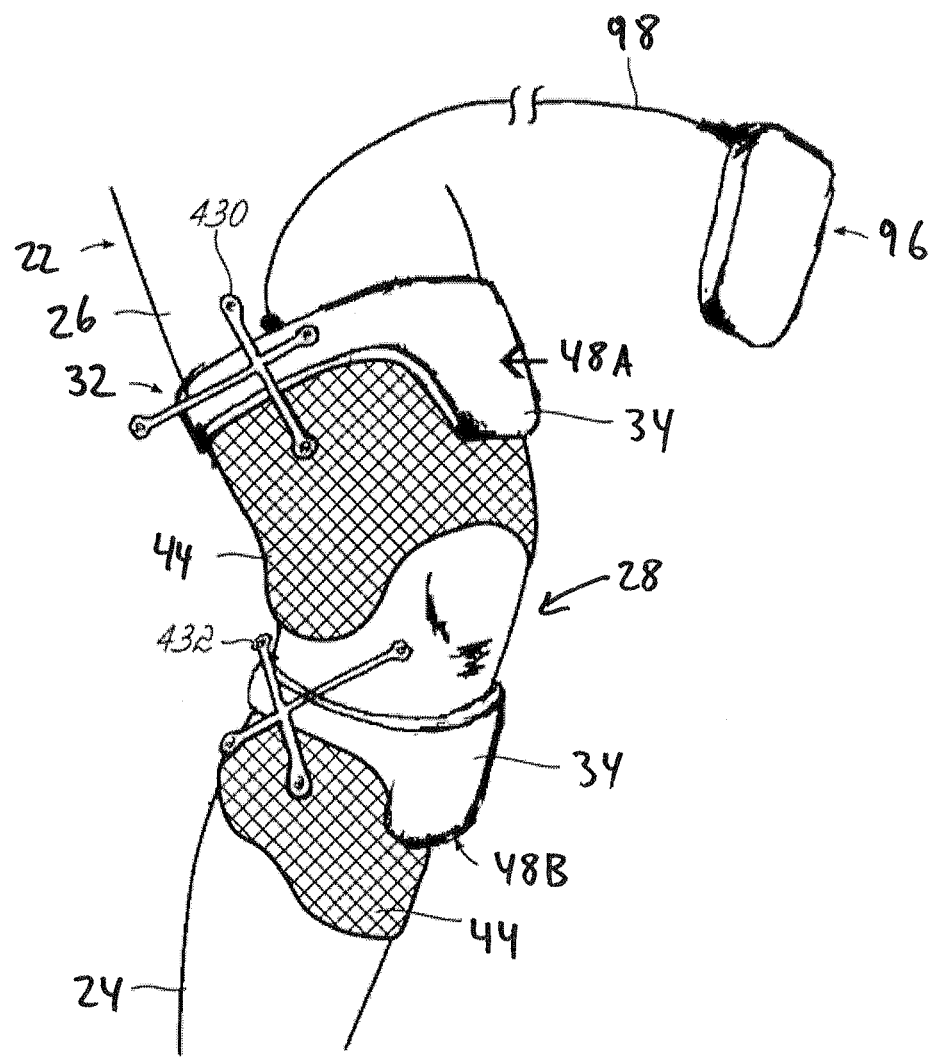
FIG. 20 is a perspective view of a knee brace on a patient's knee that includes optical location tracking devices.

FIG. 20 illustrates the knee brace 32 of FIG. 1 including two optical trackers 430, 432 for comparison with data acquired by the inertial monitoring units 48A, 48B while tracking human motion. For simplification, the knee brace 32 is not illustrated with the ultrasound transducers 40 or the vibration sensors 38. The optical trackers may be any suitable commercially-available optical tracker, such a Polaris Spectra optical tracker, available from Northern Digital Inc. of Waterloo, Ontario, Canada.

Figure 21A:
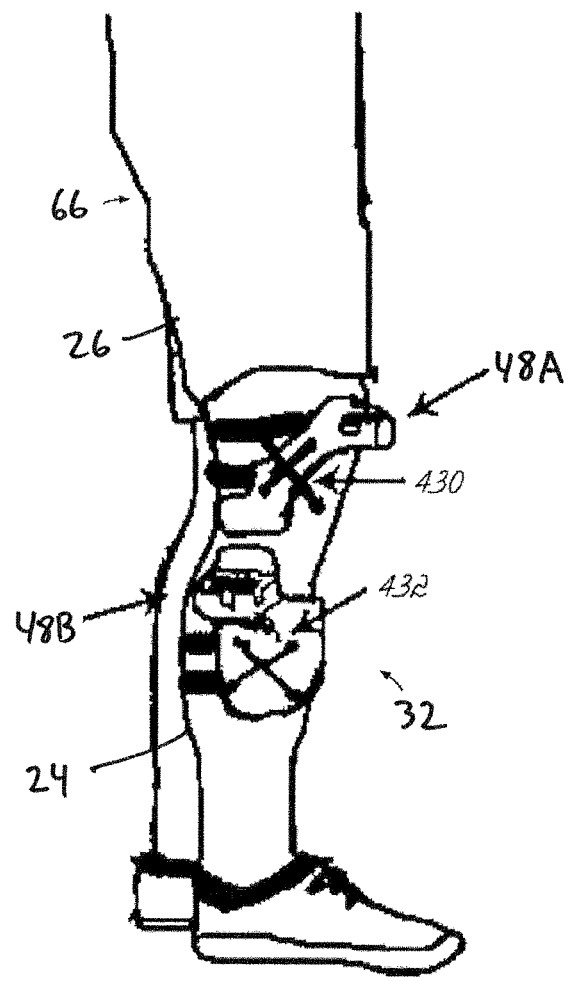
FIGS. 21A and 22A are perspective views of the knee brace of FIG. 20 with the patient in a static standing position and in a static sitting position.
Figure 21B:
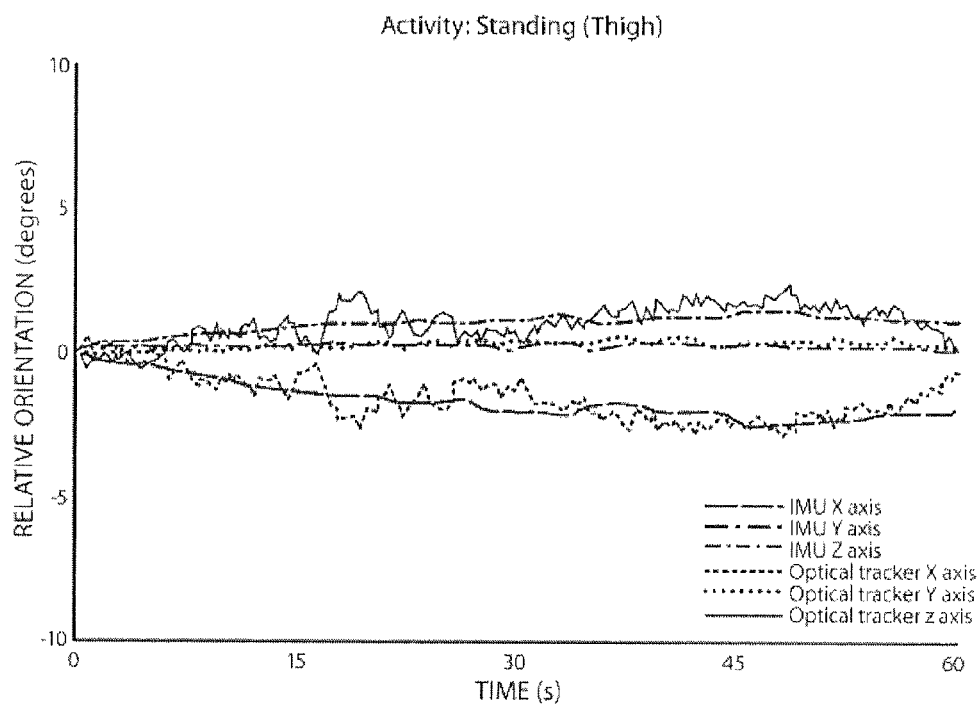
FIGS. 21B and 22B are graphical views representing the motion of the distal femur in the static standing position of FIG. 21A and in the static sitting position of FIG. 22A, respectively.
Figure 21C:
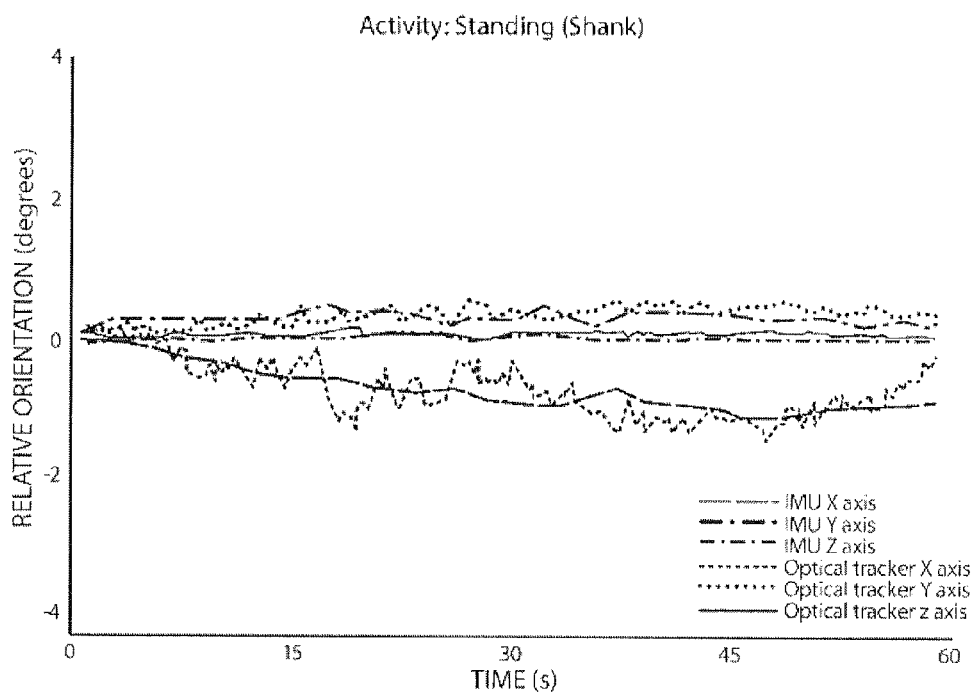
FIGS. 21C and 22C are graphical views representing motion of the proximal tibia in the static standing position of FIG. 21A and in the static sitting position of FIG. 22A, respectively.
Figure 22A:
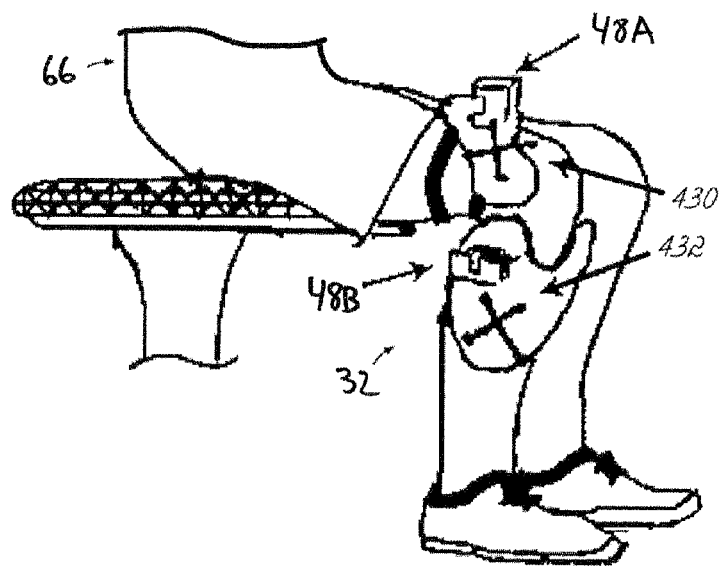
Figure 22B:
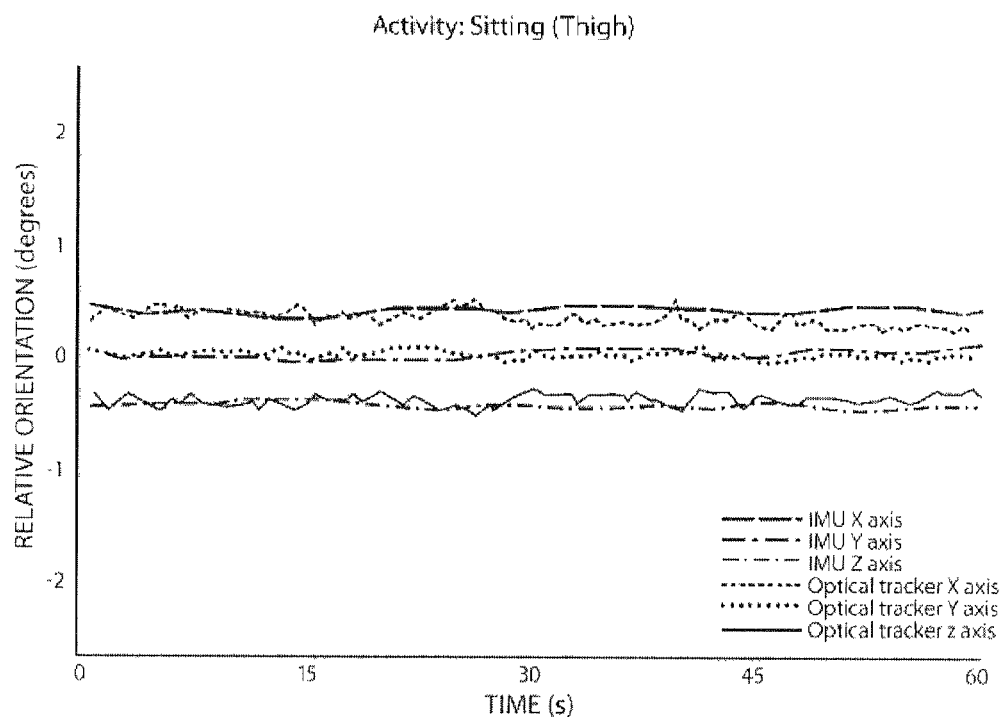
Figure 22C:
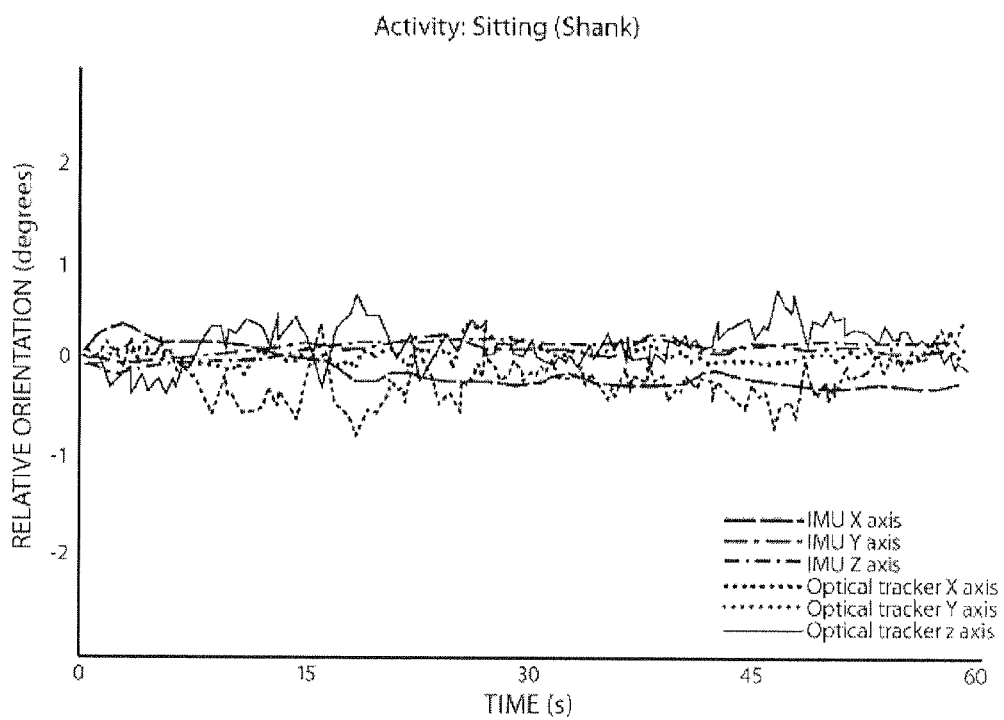

FIGS. 21A and 22A illustrate two of four activities performed by a patient 429 wearing the knee brace 32 and include a static standing position (FIG. 21A) and a static sitting position (FIG. 22A). That is, the patient 429 was asked to stand or remain seated, each for a selected period of time (for example, about 60 sec.), and during which positional signals from both the inertial monitoring units 48A, 48B and the optical trackers 430, 432 were acquired. The signals from each position, standing and sitting, are shown for the thigh 26 and the shank 24 in FIGS. 21B-21C and 22B-22C, respectively.

With continued reference to FIGS. 4A and 4B, for each position the data is zeroed at the initial pose to null orientations and a value of zero degrees on all three sensing axes X1, X2, X3, is assumed. The "X" axes of the graphs depicted in FIGS. 21B, 21C, 22B, and 22C represent the F3 and T3 axes for the inertial monitoring unit 48 and the optical tracker 430, 432 and are indicative of the flexion/extension angle of the knee joint. Similarly, the "Y" axes represent the F1 and T1 axes and are indicative of the abduction/adduction angle of the knee joint, and the "Z" axes represent the F2 and T2 axes and are indicative of an axial rotation of the knee joint.

Figure 23A:
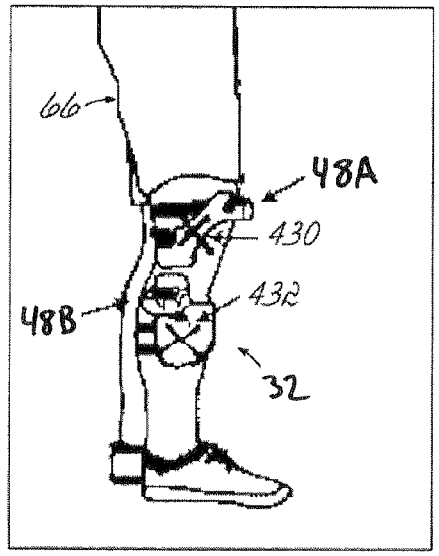
FIGS. 23A-23D are diagrammatic views illustrating a sequence of positions representing repeated dynamic motion of a patient wearing the knee brace of FIG. 20 and moving from a standing position to a deep knee bend position.
Figure 23B:
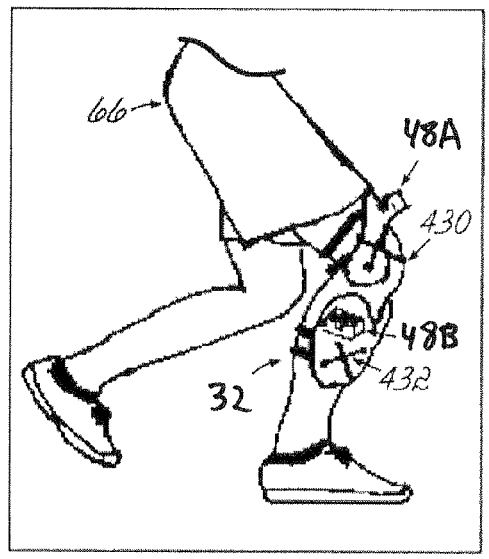
Figure 23C:
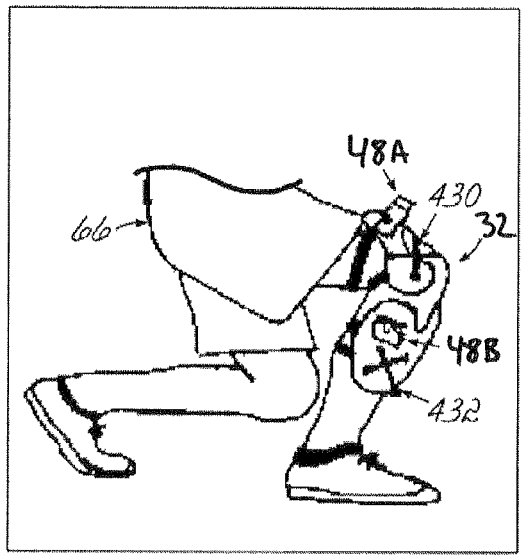
Figure 23D:
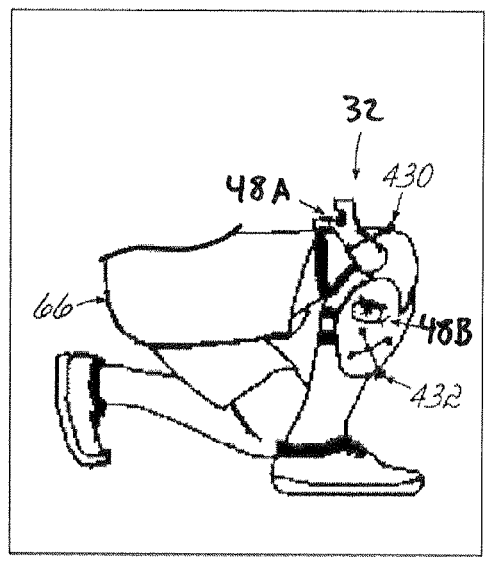
Figure 23E:
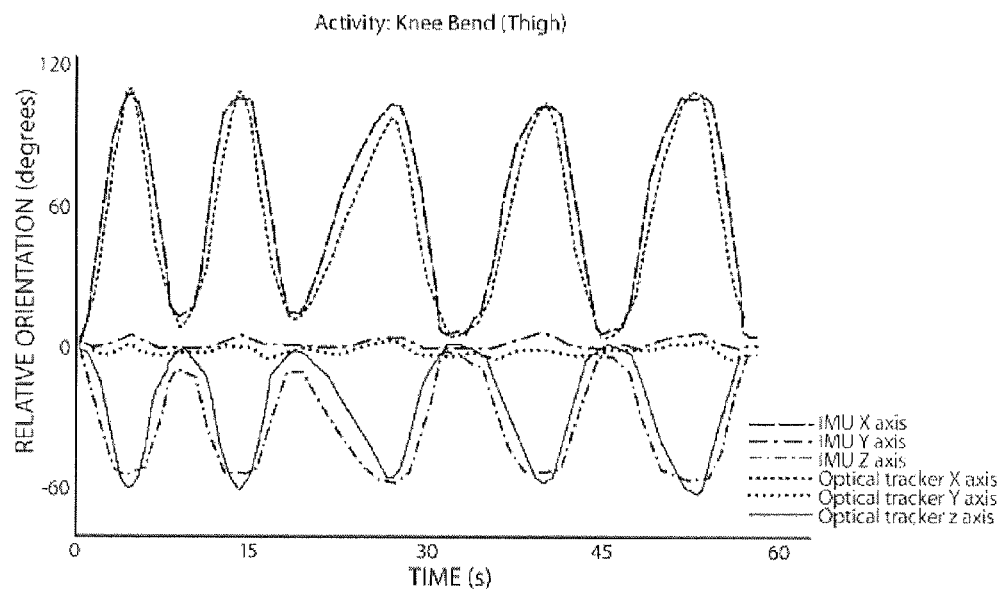
FIGS. 23E and 23F are graphical views representing motion of the femur and the tibia during repeated motion as shown in FIGS. 18A-18D for comparing the IMU motion tracking with the optical tracking device.
Figure 23F:
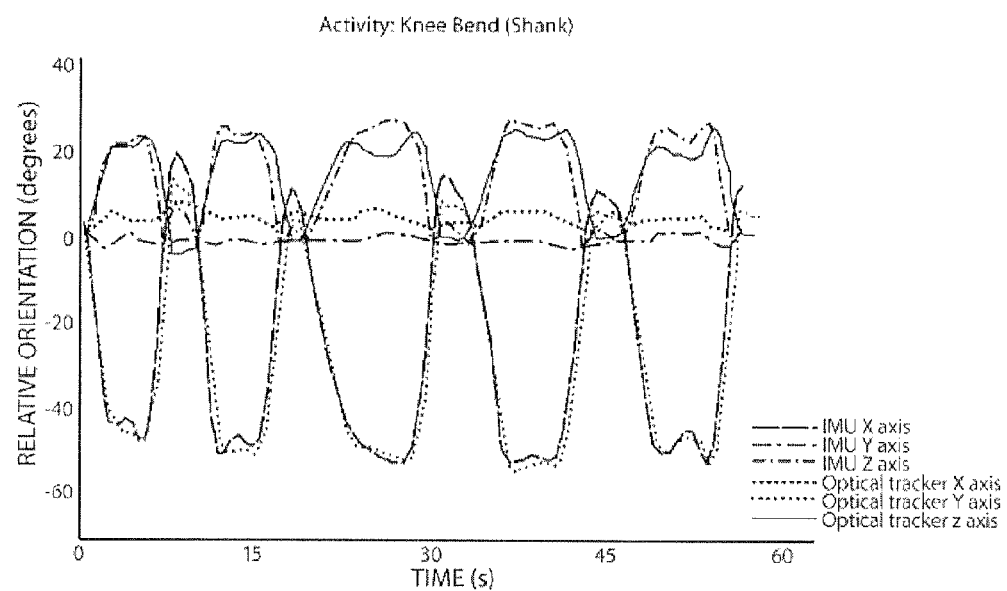

FIGS. 23A-23D illustrate a third of the four activities performed by the patient 66 wearing the knee brace 32 and includes a dynamic, deep knee bend. The patient 66 was asked to perform multiple knee bends over a selected period of time. During the knee bends, data was generated by the inertial monitoring units 48A, 48B and the optical trackers 430, 432. This data was captured and used to produce the results shown in FIGS. 23E and 23F. Similarly as described above with respect to FIGS. 21A-21C and 22A-22C, the position data was zeroed at the initial pose to nullify orientations.

Figure 24C:
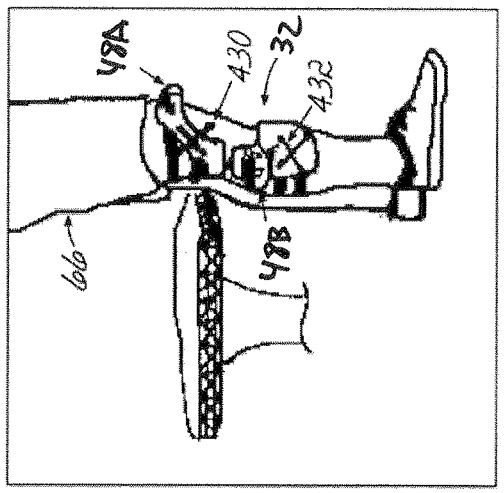
FIGS. 24A-24C are diagrammatic views illustrating a sequence of a positions representing repeated dynamic motion of a patient wearing the knee brace of FIG. 20 and moving from a seated position to a standing position.
Figure 24B:
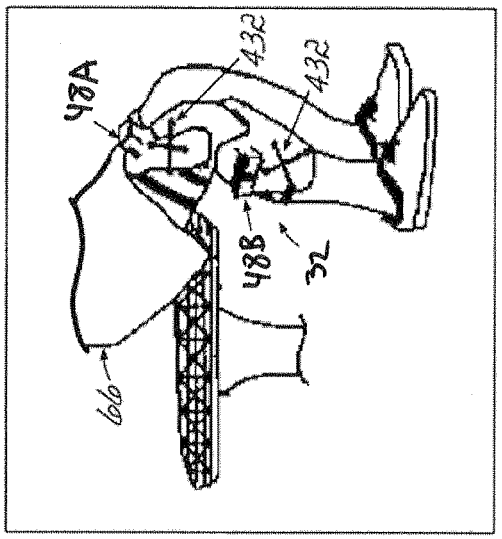
Figure 24A:
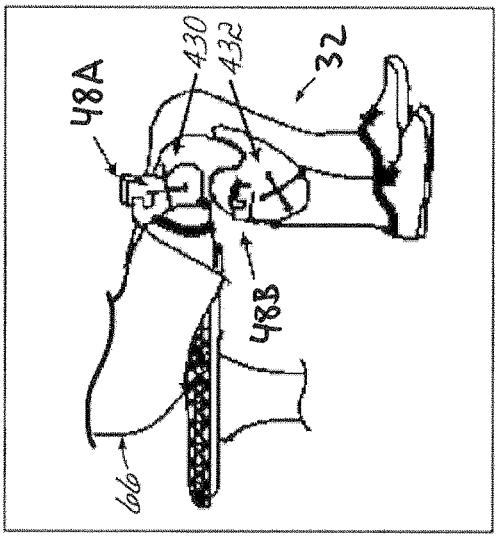
Figure 24D:
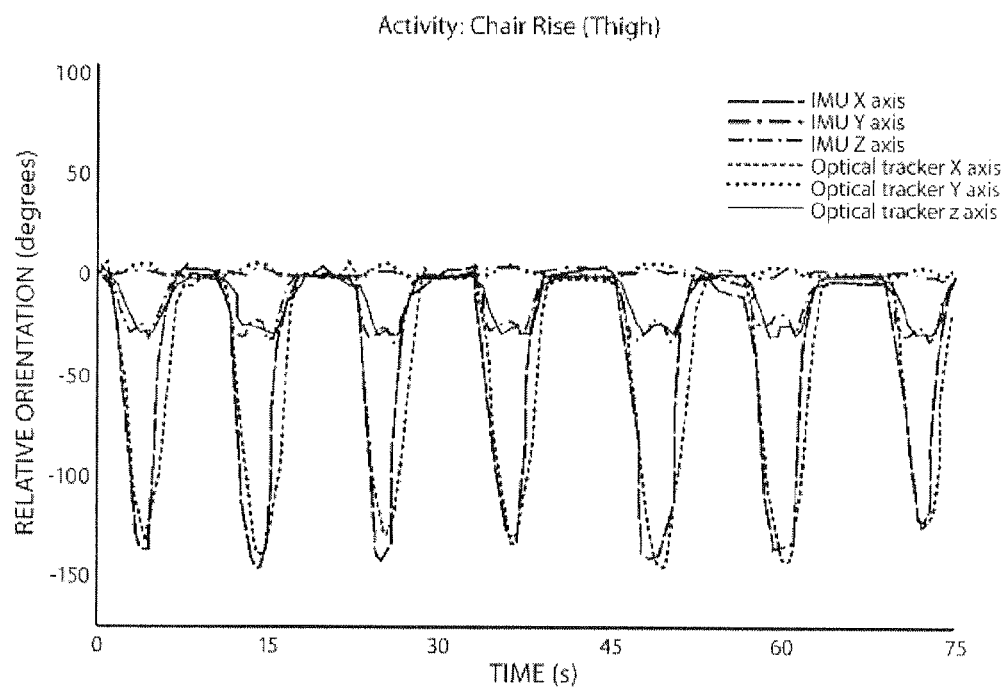
FIGS. 24D and 24E are graphical views representing motion of the distal femur and the proximal tibia during repeated motion, as shown in FIGS. 19A-19C, comparing IMU motion tracking with tracking by an optical tracking device.
Figure 24E:
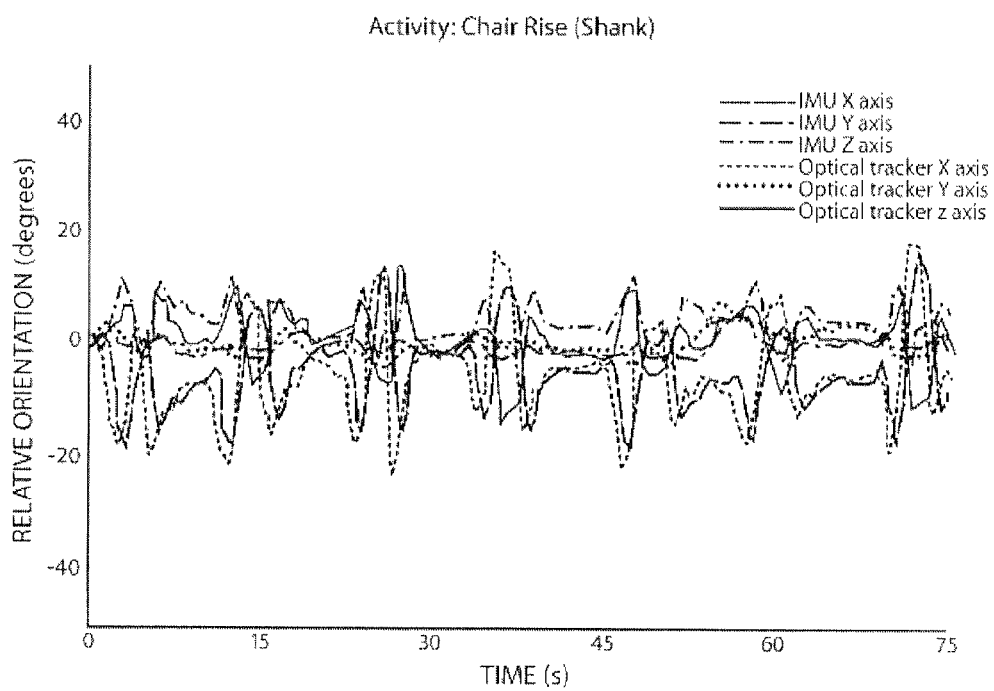

FIGS. 24A-24C illustrate a fourth activity performed by the patient 66 wearing the knee brace 32 and includes a dynamic rising from a chair motion. The patient 66 was asked to perform multiple chair raise actions over a selected period of time. While the patient 66 performed the activities, data was generated by the inertial monitoring units 48A, 48B and the optical trackers 430, 432. This data was captured and used to produce the results shown in FIGS. 24D and 24E. Similarly as described above with respect to FIGS. 23A-23F, the position data was zeroed at the initial pose to nullify orientations.

EXAMPLE 2

Embodiments of the invention may be configured to allow the user to select the inertial monitoring sensors 36 of the inertial monitoring unit 48A, 48B. That is, the number of accelerometers 56, gyroscopes 58, and magnetometers 60 used to capture position data may be selected by the user. The user may also set the measureable range of values detected by the selected sensors. Thus, the inertial tracking units 48A, 48B are customizable by the user for both the type of sensors used (e.g., accelerometer, gyroscope, or magnetometer), and the output range of the sensors used. For example, in measuring a fast dynamic motion, at least one gyroscope 58 may be used having a dynamic range (a range of measured values) of ±500 degrees per second (DPS). In contrast, for measuring a slow dynamic motion, at least one gyroscope 58 having a dynamic range of ±110 DPS may be included.

As another example, gait generally includes two distinct phases: (1) a stance phase in which changes in the orientation of the leg are relatively small; and (2) a swing phase in which the changes in orientation of the leg are relatively large. Therefore, when evaluating the stance phase of gait, the gyroscope 58 having the dynamic range of about ±110 DPS may generate more fine and accurate measurements than the gyroscope 58 having the dynamic range of ±500 DPS. In contrast, when evaluating the swing phase, the gyroscope 58 having a dynamic range of about ±500 DPS may be preferred to capture more position data samples to track the faster rate of motion (i.e., capturing data at a higher sample rate), but with each position sample having a lower resolution.

Persons having ordinary skill in the art will understand that the selection of the inertial monitoring sensor 36 in the above example does not necessarily include a physical replacement of the ±500 DPS dynamic range gyroscope 58 with the ±110 DPS dynamic range gyroscope 58. Instead, the inertial monitoring unit 48 may include a plurality of different types of inertial monitoring sensors 36, as well as sensors 36 of the same type having different dynamic ranges. The processor 72 of inertial monitoring unit 48 may be configured to switch between sensors having different dynamic range or sensitivities based on sensed motion. The processor 72 may also be configured to allow the user to manually select the sensors 36 from which data is to be collected. So, for the above example, the inertial monitoring unit 48 may be configured to automatically switch between the gyroscope 58 with the dynamic range of ±110 DPS and the gyroscope with the dynamic range of ±500 DPS based on the sensed motion.

EXAMPLE 3

Figure 25:
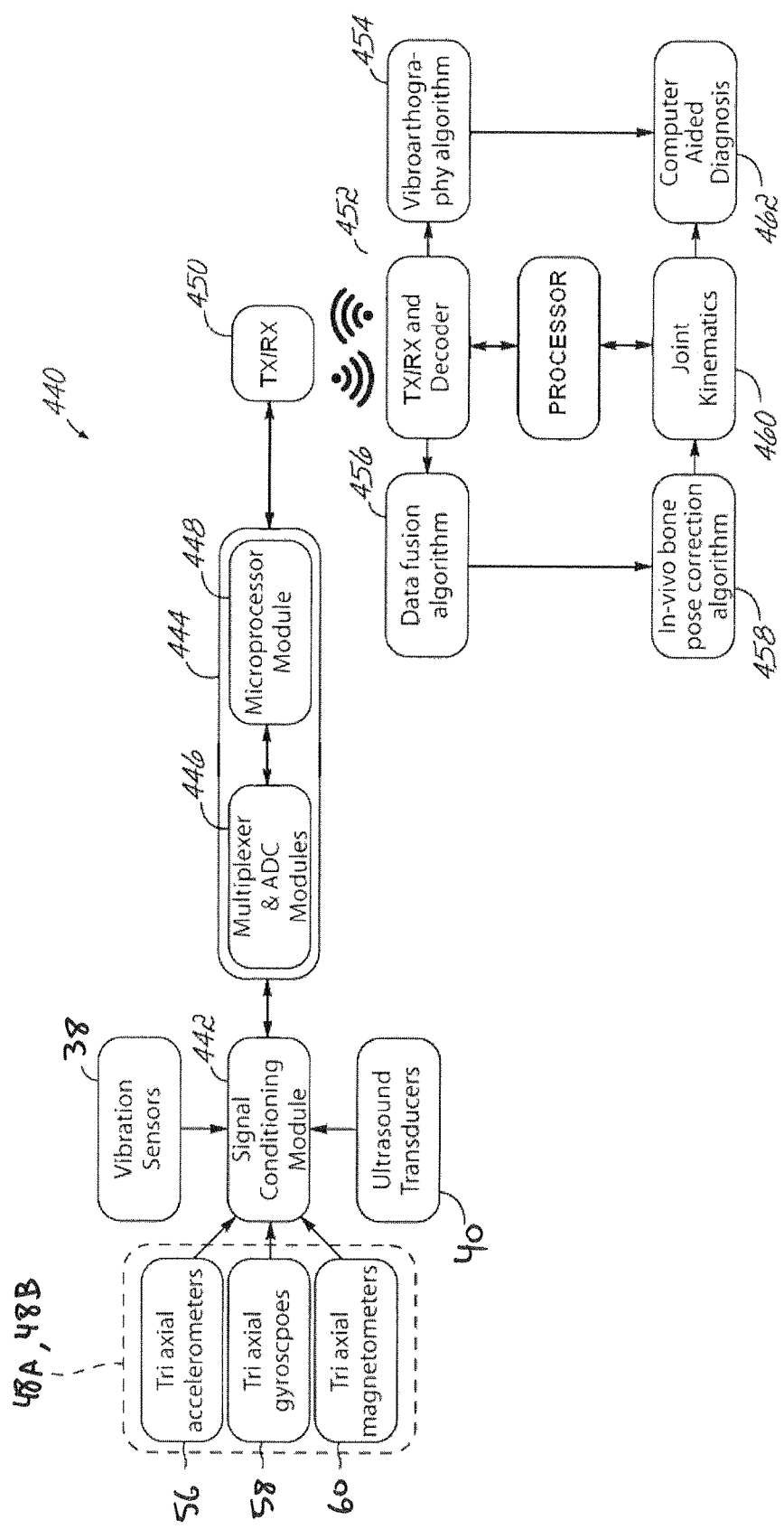
FIG. 25 is a schematic of the joint monitoring apparatus electronic and signal processing functions in accordance with an embodiment of the invention.

FIG. 25 illustrates a motion tracking apparatus, or system 440 for use in diagnosing a joint injury in accordance with an embodiment of the invention. In a specific embodiment, the system 440 may be configured for diagnosing a joint injury in an animal, such as an equine or a canine. To this end, the motion tracking system 440 may include a modified version of the knee brace 32 of FIG. 1 that includes inertial monitoring units 48A, 48B, with each of the modules 48A, 48B including a plurality of tri-axial accelerometers 56, a plurality of tri-axial gyroscopes 58, and a plurality of tri-axial magnetometers 60. The knee brace 32 may further include vibration sensors 38 and ultrasound transducers 40 as was described previously. These vibration sensors 38 and ultrasound transducers 40 may be part of one or more vibration detection modules 50 and/or ultrasound modules 52. Moreover, the inertial monitoring units 48A, 48B, vibration detection modules 50, and/or ultrasound modules 52 may operate as previously described.

Signals acquired by inertial monitoring units 48A, 48B, vibration detection modules 50, and/or ultrasound modules 52 may be transferred to a signal conditioning module 442, which may include filtering and amplification circuits. The conditioned signals are then coupled to a signal processing module 444. The signal processing module 444 includes multiplexers and ADCs 446 that select and convert the conditioned signals into a digital signal that is provided to the processor module 448, which may include one or more processors that provide the processors 72, 79, 92 of inertial monitoring unit 48, vibration detection module 50, and ultrasound module 52. The processing module 444 is coupled to a transceiver module 450 configured to receive the processed signals and transmit the processed signals to a transceiver/decoder module 452.

The received and decoded signals are provided to a data fusion algorithm 456 and a vibroarthrography algorithm 454, which may be executed by a processor 455. In an embodiment of the invention, the processor 455 may be the processor 110 of computer 54. In any case, the vibroarthrography and data fusion algorithms 454, 456 may be separately applied to the received and decoded signal. The data fusion algorithm 456 is configured to combine the signals from the various modules 48, 50, 52 prior to applying an in-vivo bone pose correction algorithm 458. The corrected fused signals are then provided to a joint kinematics module 460, which may generate models of the visual movement of the joint. The visual movement of the joint may be displayed to the user (e.g., on a monitor included in the user interface 118 of computer 54) to allow the user to evaluate the relative motions of the bones and tissues comprising the joint. Systems and methods of displaying kinematics are described in more detail in U.S. patent application Ser. No. 13/758, 151, entitled "METHOD AND APPARATUS FOR THREE DIMENSIONAL RECONSTRUCTION OF A JOINT USING ULTRASOUND", filed on Feb. 4, 2013, the disclosure of which is incorporated herein by reference in its entirety.

The vibroarthrography algorithm 454 is configured to identify and evaluate various vibrational patterns associated with the movement and/or articulations of the bones and tissues comprising the joint being evaluated. In an embodiment of the invention, the output of the vibroarthrography algorithm 454 and the joint kinematics module 460 may be provided to a trainable neural network that provides a computer aided diagnosis module 462 that generates a diagnosis for the joint. Systems and methods of diagnosing joint conditions based on vibrations are described in more detail in concurrently filed U.S. patent application entitled "DETERMINATION OF JOINT CONDITION BASED ON VIBRATION AND ACCOUSTIC ANALYSIS", the disclosure of which is incorporated herein by reference in its entirety.

EXAMPLE 4

It is common in veterinary medicine to encounter animals whose gait or ability to walk normally is impaired by a joint injury. For example, traumatic joint disease in horses includes synovitis (inflammation of the fluid-producing membrane), capsulitis (inflammation of the fibrous joint capsule), articular cartilage and bone fragmentation, ligamentous tearing, and eventually osteoarthritis. In many cases, the disease process primarily involves soft tissue overuse and microtrauma to the bone surfaces, and therefore can be challenging to diagnose without diagnostic anesthesia. In addition to localizing pain to a certain joint with aide of diagnostic anesthesia, radiographs, ultrasound, computed tomography (CT), magnetic resonance imaging (MRI) techniques and diagnostic arthroscopy have all be used to confirm causes of joint lameness. Often the specific nature of the injury is only apparent after multiple imaging studies and gait analysis.

Aggressive treatment in joint disease is indicated to immediately decrease soft tissue swelling and inflammation, as well as to postpone the onset of permanent osteoarthritic changes. There is inherent difficulty in objectively identifying joint pathology. Thus, joint pathologies are normally identified by subjective examination and reports of lameness or "shortness of stride" from trainers. The goal of any systemic or intraarticular (medications put directly into the joint) therapy is to stop problems before they occur rather than wait for abnormal radiographs and then start aggressive therapy.

Inflammatory and degradative enzymes that destroy normal joint environments can be altered by use of hyaluronic acid (HA) and corticosteroids injected into the joint. The combination of the two has been scientifically proven to have a more thorough and lasting effect than HA or corticosteroids alone. Select corticosteroids have been evaluated in the equine research model proving their efficacy and have shown certain corticosteroids to be protective to the joint environment, while others have been shown to the degradative or damaging to the joint.

Typically, when there is mild soreness (joint capsulitis or synovitis) in a joint, and joint therapy is instituted 2 to 3 times per year, the environment inside the joint becomes more hospitable to cartilage, and is not destructive to the cartilage. However, damage may occur from excess corticosteroid injections, or when there is cartilage fragmentation and bone alterations in a joint, which is usually associated with lameness.

The motion tracking system described in Example 3 may be particularly useful for diagnosing the aforementioned joint problems, documenting the gait, tracking treatment progress, and following joint treatment in animals. As would be understood by one skilled in the art, the knee brace 32 would need to fit the dimensions of the joint of interest. For example the when adapted for an equine hock, the knee brace would need to be lengthened relative one used for a human patient. Other system changes may include different calibration or selection of sensors/modules 38, 56, 58, 60 adapted to the expected movements or vibrations associated with an equine patient.

Figure 26:
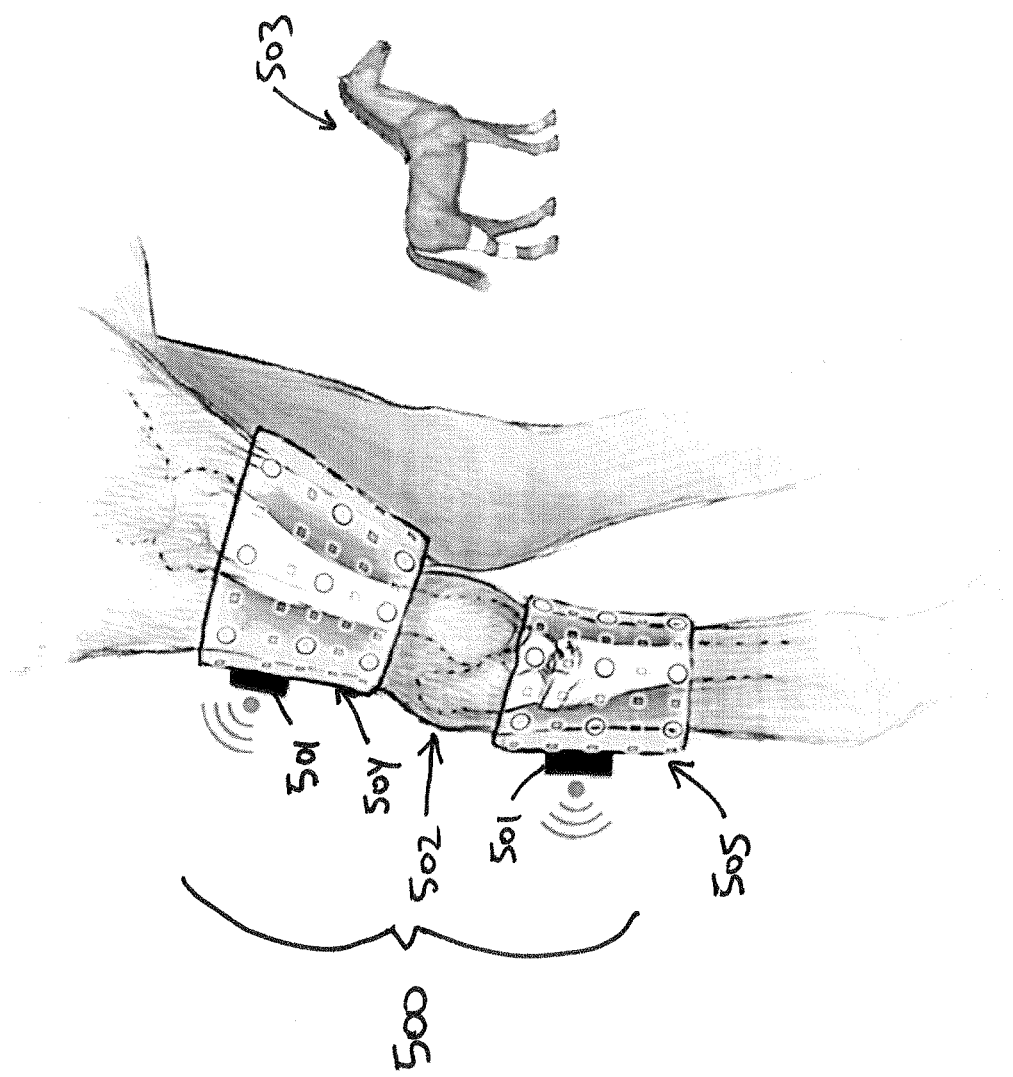
FIG. 26 is a perspective view of a brace on a horse's hock joint in accordance with an embodiment of the invention.

FIG. 26 illustrates a "brace" 500 including an upper section 504 and a lower section 505. Thus, in the illustrated embodiment, the there is no physical connection shown between the upper and lower sections 504, 505 of the brace 500. However, alternative embodiments of the brace 500 may include a one piece brace in which the upper and lower sections 504, 505 are connected. In any case, the upper and lower sections 504, 505 of the brace 500 may each include an inertial monitoring unit 501 to track the relative motion of the joint as described in detail above with respect to the knee brace 32 of FIGS. 1 and 20. Although not shown in FIG. 26, the brace 500 may also include one or more vibration detection modules 50 and/or ultrasound modules 52.

EXAMPLE 5

In an embodiment of the invention, the inertial monitoring unit 48 and various adaptations of the motion tracking system 440 may also be used with a modified knee brace 32 to track the positions of objects used in medicine and surgery relative to locations in the body. In these tracking applications, the vibration sensors 38 and vibroarthrography algorithm 454 may be omitted from the motion tracking system 440.

For example, the use of special drapes to aid in the imaging and guided injection of joints is described in pending PCT Application No. US13/25131, entitled "THREE-DIMENSIONAL GUIDED INJECTION DEVICE AND METHODS", filed on Feb. 7, 2013, the disclosure of which is incorporated herein by reference in its entirety. The drape described in the aforementioned PCT application may be made from the Alpha® Liner material described above, and may be adapted to include ultrasound transducers 40 and one or more inertial monitoring units 48. The ultrasound transducers 40 may be operated as described above to obtain images of the bones and structures comprising a joint. An inertial monitoring unit 48 located on or in the drape may be used to track the location of the drape relative to the anatomy of interest using the data fusion algorithm 456, in-vivo bone pose correction algorithm 458, and joint kinematics module 460. An inertial monitoring unit 48 located on the injection device may be used to track the location of the injection device. The computer aided diagnosis module 462 of the motion tracking system 440 may be replaced with a function implementing computer aided navigation that integrates the image of the joint structure along with the locations of one or more inertial monitoring units 48 to display a vector to the target for the medical professional.

EXAMPLE 6

In an embodiment of the invention, the inertial monitoring unit 48 and various adaptations of the motion tracking system 440 may be used separate from the knee brace 32 to track the positions of objects used in medicine and surgery relative to anatomical features. That is, embodiments of the invention may be used as a surgical navigation system for tracking medical devices in space. To this end, the vibration sensors 38, ultrasound transducers 40, vibroarthography algorithm 454, in-vivo bone pose correction algorithm 458, joint kinematics module 460, and computer aided diagnosis module 462 may be omitted from the motion tracking system 440 and the inertial monitoring units 48 attached to the object to be tracked.

For example, use of a "sensor" to track the location of prosthetic joint implant during surgery as part of a process and device for orienting the implant is described in U.S. Patent Application Publication No. 2009/0289806, filed Mar. 13, 2009 and entitled "COMPUTER-GUIDED SYSTEM FOR ORIENTING THE ACETABULAR CUP IN THE PELVIS DURING TOTAL HIP REPLACEMENT SURGERY", the disclosure of which incorporated herein by reference in its entirety.

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. The various features of the invention may be used alone or in any combination depending on the needs and preferences of the user. For example, one skilled in the art will understand that the terms inertial monitoring sensor 36, vibration sensor 38, ultrasound transducer 40, inertial monitoring unit 48, vibration detection module 50, and ultrasound module 52 may at times be used interchangeably depending on the context of the embodiment being described, and are not intended to be limiting.

Therefore, the present invention in its broader aspects is not limited to the specific details representative apparatus and method, and illustrative examples shown and described. Accordingly, departures may be made from such details without departure from the spirit or scope of applicant's general inventive concept. However, the invention itself should only be defined by the appended claims.

What is claimed is:

1. A joint monitoring apparatus comprising:
    a first brace including a first inertial measurement unit configured to be coupled to and detect motion of a first portion of a patient, and to collect and transmit data indicative of the detected motion, the first brace also including a first ultrasound transducer module located in a fixed position with respect to the first inertial measurement unit, the first brace further including a first microprocessor communicatively coupled to the first inertial measurement unit and the first ultrasound transducer module;

a second brace including a second inertial measurement unit configured to be attached to and detect motion of a second portion of the patient, and to collect and transmit data indicative of the detected motion, the second brace also including a second ultrasound transducer module located in a fixed position with respect to the second inertial measurement unit, the second brace further including a second microprocessor communicatively coupled to the second inertial measurement unit and the second ultrasound transducer module; and a processor communicatively coupled to the first and second microprocessors, the processor communicatively coupled to a memory including program code that, when executed by the processor, causes the processor to: (a) generate a virtual dynamic model of an in-vivo patient specific bone joint representative of movement of a first bone, wherein the first bone is associated with the first portion of the patient, with respect to a second bone, wherein the second bone is associated with the second portion of the patient, and (b) generate instructions to visually display the virtual dynamic model.

2. The apparatus of claim 1 wherein each of the first and the second ultrasound transducer modules includes:
an ultrasound transducer that generates a signal in response to receiving an ultrasound echo within a receiving period, and
a variable gain amplifier coupled to the ultrasound transducer, the variable gain amplifier being configured to dynamically adjust a gain applied to the signal generated by the ultrasound transducer based on a time the ultrasound echo is received within the receiving period.

3. The apparatus of claim 2 wherein the gain applied to the signal generated by the ultrasound transducer is dynamically increased over the receiving period so that the gain is greater at the end of the receiving period than at the beginning of the receiving period.

4. The apparatus of claim 1 wherein each of the first and second ultrasound transducers modules includes an ultrasound transducer which is configured to emit an ultrasound pulse and receive a received echo of the ultrasound pulse, the received echo of the ultrasound pulse being utilized to determine a distance between the ultrasound transducer and a surface of tissue responsible for the received echo.

5. The apparatus of claim 1 wherein:
the first ultrasound transducer module includes a first ultrasound transducer which is configured to transmit a first ultrasound pulse and receive an echo of the first ultrasound pulse;
the second ultrasound transducer module includes a second ultrasound transducer which is configured to transmit a second ultrasound pulse and receive an echo of the second ultrasound pulse; and
the program code stored in the memory is configured to further cause the processor to:
determine a first distance between the first bone and the first ultrasound transducer based on the echo of the first ultrasound pulse; and
determine a second distance between the second bone and the second ultrasound transducer based on the echo of the second ultrasound pulse, and
determine an orientation of the first bone with respect to the second bone based on the first and second distances.

6. The apparatus of claim 5 wherein:
the virtual dynamic model is generated from a 3-D patient-specific model of the bone joint stored in the memory; and
the program code stored in the memory is further configured to cause the processor to manipulate the 3-D patient specific model based on the determined orientation of the first bone with respect to the second bone to generate the virtual dynamic model.

7. The apparatus of claim 1, wherein:
the first brace further includes a first vibration detector configured to detect vibrations and to collect and transmit data indicative of the detected vibrations;
the first microprocessor is communicatively coupled to the first vibration detector;
the second brace further includes a second vibration detector configured to detect vibrations and to collect and transmit data indicative of the detected vibrations; and,
the second microprocessor is communicatively coupled to the second vibration detector.

8. The apparatus of claim 7 wherein the program code is further configured to cause the processor to generate a vibroarthrogram correlating detected vibrations with the data indicative of the detected motion.

9. The apparatus of claim 7 wherein the program code is further configured to cause the processor to identify a vibration pattern in the detected vibrations.

10. The apparatus of claim 9 wherein the program code is further configured to cause the processor to diagnose a condition based on the identified vibration pattern.

11. The apparatus of claim 1 further comprising:
a segment coupling the first brace to the second brace, the segment being configured to allow pivotal motion of the first inertial measurement unit with respect to the second inertial measurement unit.

12. The apparatus of claim 1 further comprising:
a first optical tracker located in a fixed position with respect to the first inertial measurement unit; and
a second optical tracker located in a fixed position with respect to the second inertial measurement unit.

13. The apparatus of claim 1 wherein the first and second inertial measurement units each include at least one of:
a first sensor configured to generate a signal indicative of an acceleration of the respective inertial measurement unit;
a second sensor configured to generate a signal indicative of a rotation of the respective inertial measurement unit; and
a third sensor configured to generate a signal indicative of a tilt of the respective inertial measurement unit.

14. The apparatus of claim 1 wherein at least one of the first and second inertial measurement units includes:
a first inertial measurement unit sensor having a first sensitivity; and
a second inertial measurement unit sensor having a second sensitivity,
wherein the at least one of the first and second inertial measurement units is configured to select one of the first or second inertial measurement sensors from which to collect and transmit data based on a rate of motion of the at least one of the first and second inertial measurement units.

15. The apparatus of claim 14 wherein the first and second inertial measurement unit sensors are selected from a group consisting of accelerometers, gyroscopes, and magnetometers.

16. A method of monitoring multiple bones, the method comprising:
mounting a first brace on a first portion of a joint of a subject, the first brace including a first inertial measurement unit, a first ultrasound transducer, and a first microprocessor;
detecting motion of a first bone of a joint of a subject using data output from the first inertial measurement unit and the first ultrasound transducer;
mounting a second brace on a second portion of a joint of a subject, the second brace including a second inertial measurement unit, a second ultrasound transducer, and a second microprocessor;
detecting motion of a second bone of the joint of the subject using data output from the second inertial measurement unit and the second ultrasound transducer;
processing, using the first microprocessor and the second microprocessor, the data from the first and second inertial measurement units and the first and second ultrasound transducers to generate kinematic data indicative of the dynamic position of the first bone with respect to the second bone during motion; and
at least one of displaying a kinematic representation of the first bone with respect to the second bone across a range of the motion, and diagnosing a condition of the joint based upon the kinematic data.

17. The method of claim 16 further comprising:
transmitting a first ultrasound pulse from the first ultrasound transducer toward the first bone of the joint of the subject, the first ultrasound transducer having a known position with respect to the first inertial measurement unit;
receiving an echo of the first ultrasound pulse with the first ultrasound transducer;
determining a first distance between the first ultrasound transducer and the first bone based on the received echo;
transmitting a second ultrasound pulse from the second ultrasound transducer toward the second bone of the joint of the subject, the second ultrasound transducer having a known position with respect to the second inertial measurement unit;
receiving an echo of the second ultrasound pulse with the second ultrasound transducer; and
determining a second distance between the second ultrasound transducer and the second bone based on the received echo.

18. The method of claim 17 further comprising:
generating a signal with the first ultrasound transducer in response to receiving the first echo;
amplifying the generated signal with a variable gain amplifier; and
adjusting a gain of the variable gain amplifier based on an amount of time between the transmission of the first ultrasound pulse and the reception of the echo received by the first ultrasound transducer.

19. The method of claim 16 wherein processing the data from the first and second inertial measurement units and the first and second ultrasound transducers to generate kinematic data comprises:
processing data output from the first inertial measurement unit and the first ultrasound unit using the first microprocessor;
processing data output from the second inertial measurement unit and the second ultrasound unit using the second microprocessor; and
transmitting the processed data from the first microprocessor and the second microprocessor to a central processor to generate the kinematic data, wherein the kinematic data includes orientation data indicating the relative orientation of the first bone with respect to the second bone across the range of motion.

20. The method of claim 19 wherein:
the data output from the first ultrasound transducer is indicative of a first distance between the first ultrasound transducer and the first bone, the first ultrasound transducer having a known position relative to the first inertial measurement unit;
the data output from the second ultrasound transducer is indicative of a second distance between the second ultrasound transducer and the second bone, the second ultrasound transducer having a known position relative to the second inertial measurement unit;
and wherein the method further comprises:
determining, using the first microprocessor, the first distance between the first ultrasound transducer and the first bone based on the data output from the first ultrasound transducer;
determining, using the second microprocessor, the second distance between the second ultrasound transducer and the second bone based on the data output from the second ultrasound transducer; and
determining an orientation of the joint based on the first and second distances.

21. The method of claim 20 further comprising:
receiving data indicative of a vibration generated by the joint;
correlating the received data indicative of the vibration with the determined orientation of the joint to have common times; and
generating a vibroarthrogram based on the correlation of the received data indicative of the vibration with the determined orientation of the joint.

22. The method of claim 20 further comprising:
receiving data indicative of a vibration generated by the joint;
identifying a vibration pattern in the received data indicative of the vibration; and
diagnosing the condition of the joint using the vibration pattern.

* * * * *